(12) United States Patent
Aebi et al.

(10) Patent No.: US 8,471,004 B2
(45) Date of Patent: Jun. 25, 2013

(54) BICYCLIC COMPOUNDS

(75) Inventors: Johannes Aebi, Binningen (CH); Alfred Binggeli, Binningen (CH); Luke Green, Basel (CH); Guido Hartmann, Loerrach (DE); Hans P. Maerki, Basel (CH); Patrizio Mattei, Richen (CH)

(73) Assignee: Hoffman-La Roche Inc., Nutley, NJ (US)

( * ) Notice: Subject to any disclaimer, the term of this patent is extended or adjusted under 35 U.S.C. 154(b) by 20 days.

(21) Appl. No.: 12/892,968

(22) Filed: Sep. 29, 2010

(65) Prior Publication Data

US 2011/0082294 A1    Apr. 7, 2011

(30) Foreign Application Priority Data

Oct. 7, 2009 (EP) .................................... 09172408

(51) Int. Cl.
*C07D 498/00* (2006.01)
(52) U.S. Cl.
USPC .......................................... 544/105; 540/552
(58) Field of Classification Search
USPC .......................................... 540/552; 544/105
See application file for complete search history.

(56) References Cited

FOREIGN PATENT DOCUMENTS

| EP | 0290902 | 11/1988 |
|---|---|---|
| WO | 2009/010429 | 1/2009 |
| WO | 2009/043747 | 4/2009 |

OTHER PUBLICATIONS

Fontanella et al. Farmaco, Edizione Scientifica (1973), 28(6), 463-77.*
Kundu et al , Indian Journal of Chemistry, 1988, vol. 27B, pp. 1124-1127.
Sakamoto et al., Journal of Organic Chemistry, 1996, vol. 61, pp. 8496-8499.
Velazquez et al , Organic Letters, 2007, vol. 9, pp. 3061-3054.
Aggarwal, et al., Organic Letters, 2004, vol. 6, pp.1469-1471.
English language Abstract corresponding to Foreign Document EP0290902, (2008).

* cited by examiner

*Primary Examiner* — Kahsay T Habte

(57) ABSTRACT

The invention is concerned with novel bicyclic compounds of formula (I),

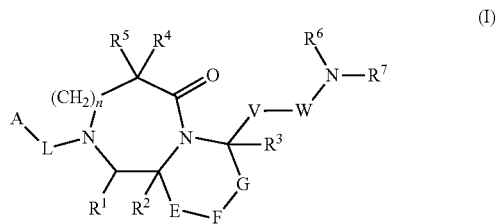

(I)

wherein A, L, E, F, G, $R^1$, $R^2$, $R^3$, $R^4$, $R^5$, $R^6$, $R^7$, V, W and n are as defined in the description and in the claims, as well as physiologically acceptable salts thereof. These compounds are antagonists of CCR2 receptor, CCR5 receptor and/or CCR3 receptor and can be used as medicaments.

20 Claims, No Drawings

BICYCLIC COMPOUNDS

PRIORITY TO RELATED APPLICATION(S)

This application claims the benefit of European Patent Application No. 09172408.8, filed Oct. 7, 2009, which is hereby incorporated by reference in its entirety.

FIELD OF THE INVENTION

The compounds of formula (I) are CCR2 receptor (Chemokine Receptor 2/Monocyte chemotactic protein 1 receptor) antagonists and/or also CCR5 receptor (Chemokine Receptor 5) and/or CCR3 receptor (Chemokine Receptor 3) antagonists.

BACKGROUND OF THE INVENTION

Chemokines are a family of small, secreted proinflammatory cytokines functioning as chemoattractants for leukocytes. They promote trafficking of leukocytes from vascular beds into surrounding tissues in response to inflammatory signals. Chemotaxis starts upon chemokine binding to receptors (GPCRs) by initiating signaling pathways involving increased Ca-flux, inhibition of cAMP production, rearrangements of the cytoskeleton, activation of integrins and of cell motility processes and an increase in the expression of adhesion proteins.

Proinflammatory chemokines are considered to be involved in the development of atherosclerosis and other important diseases with inflammatory components like rheumatoid arthritis, asthma, multiple sclerosis, transplant rejection and ischemia reperfusion injury with specific prominent effects in nephropathy and peripheral vascular diseases. Monocyte Chemotactic protein 1 is considered to be the major stimulated chemokine mediating inflammatory processes in these diseases through the CCR2 receptor on monocytes and on some T lymphocytes. In addition MCP-1/CCR2 are in discussion to be related to the progression of the metabolic syndrome to more severe stages of obese and diabetic diseases.

CCR2 has also been linked to HIV infection, and consequently the course of autoimmune diseases, through its heterodimerization with CCR5 which has a role as coreceptor for viral entry into host cells.

Thus, CCR2 can be a target of a new medicine for treatment of peripheral vascular diseases, and more specifically for treatment of patients with critical limb ischemia. Furthermore, study results and experiences from the development of a new CCR2 medicine for this indication may facilitate a follow-up development for treatment of atherosclerosis. There is a large body of information from animal models of MCP-1 and CCR2 ko mice in wt or apoE−/− or LDL-R−/− backgrounds showing that the MCP-1/CCR2 pathway is essential for monocyte/macrophage recruitment, and also for internal hyperplasia and the formation and stability of atherosclerotic lesions. In addition, numerous reports describe involvement of the MCP-1/CCR2 pathway in man post injury and in various inflammatory processes, including such in vascular beds.

SUMMARY OF THE INVENTION

The present invention relates to a compound according to formula (I)

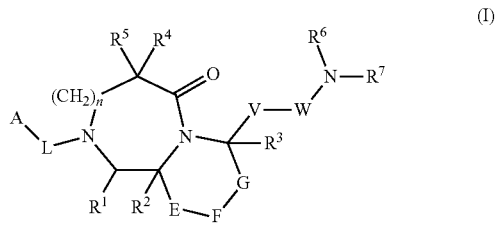

(I)

wherein
A is selected from the group consisting of: aryl, heteroaryl, arylmethyl and heteroarylmethyl, wherein the said aryl, heteroaryl and the aryl of arylmethyl are optionally substituted by one to three substituents independently selected from the group consisting of halogen, aryl, heteroaryl, $C_{1-6}$ alkyl, halo$C_{1-6}$ alkyl, $C_{1-6}$ alkoxy and halo $C_{1-6}$ alkoxy;
E is $CH_2$ or O;
F is selected from the group consisting of: $CH_2$, O, $N(R^8)$, S, SO and $SO_2$;
G is selected from the group consisting of: a single bond, $CH_2$, and $CH_2CH_2$, with the proviso that, when E is O, then F is not O, S, SO or $SO_2$;
L is selected from the group consisting of: a bond, NH—C(=O), NH—C(=S), and CH=CH—C(=O);
$R^1$, $R^2$ and $R^3$ are independently of each other selected from the group consisting of:
hydrogen,
$C_{1-6}$ alkyl, which is optionally substituted by one to three substituents independently selected from the group consisting of hydroxy, $C_{1-6}$ alkoxy, carboxyl, carbamoyl, mono or di-$C_{1-6}$ alkyl substituted aminocarbonyl and $C_{1-6}$ alkoxycarbonyl, aryl and heteroaryl, wherein said heteroaryl and aryl are optionally substituted by one to three substituents independently selected from the group consisting of halogen, $C_{1-6}$ alkyl, halo $C_{1-6}$ alkyl, $C_{1-6}$ alkoxy and halo $C_{1-6}$ alkoxy,
$C_{3-7}$ cycloalkyl, and
aryl;
$R^4$ and $R^5$ are independently of each other selected from the group consisting of:
hydrogen,
$C_{1-6}$ alkyl, which is optionally substituted by one to three substituents independently selected from the group consisting of amino, hydroxy, carboxyl, carbamoyl, mono or di-$C_{1-6}$ alkyl substituted aminocarbonyl and $C_{1-6}$ alkoxycarbonyl, and
$C_{3-7}$ cycloalkyl, which is optionally substituted by one to three substituents independently selected from the group consisting of amino, hydroxy, carboxyl, carbamoyl, mono or di-$C_{1-6}$ alkyl substituted aminocarbonyl and $C_{1-6}$ alkoxycarbonyl; or
$R^4$ and $R^5$, together with the carbon atom to which they are attached, form $C_{3-7}$ cycloalkyl or heterocyclyl which is optionally substituted by one to three substituents independently selected from the group consisting of $C_{1-4}$ alkyl, halo $C_{1-4}$ alkyl and halogen;
$R^6$ and $R^7$ are, independently of each other selected from the group consisting of:
$C_{1-6}$ alkyl,
$C_{3-6}$ alkenyl, $C_{3-6}$ alkynyl,
hydroxy $C_{2-6}$ alkyl,
$C_{1-6}$ alkoxy $C_{2-6}$ alkyl,
$C_{3-7}$ cycloalkyl, which is optionally substituted by one to three $R^d$ groups,
$C_{3-7}$ cycloalkyl $C_{1-6}$ alkyl, wherein the cycloalkyl is optionally substituted by one to three $R^d$ groups,
$C_{7-10}$ bicycloalkyl,
phenyl $C_{1-3}$ alkyl, wherein the phenyl is optionally substituted by one to three $R^d$ groups,
heteroaryl $C_{1-3}$ alkyl, wherein the heteroaryl is optionally substituted by one to three $R^d$ groups,
Heterocyclyl which is optionally substituted by one to three $R^d$ groups, and
heterocyclyl $C_{1-6}$ alkyl, wherein the heterocyclyl is optionally substituted by one to three $R^d$ groups; or
$R^6$ and $R^7$, together with the nitrogen atom to which they are attached, form heterocyclyl optionally substituted by one to three $R^d$ groups, and wherein one of the ring carbon atoms of said heterocyclyl formed by $R^6$ and $R^7$ is optionally replaced with a carbonyl group or $SO_2$;
and/or one of the ring carbon atoms of the heterocyclyl formed by $R^6$ and $R^7$ is also a ring carbon atom of a second ring which is $C_{3-7}$ cycloalkyl or heterocyclyl, which is optionally substituted by $C_{1-6}$ alkyl and wherein one or two ring carbon atoms of said second ring is optionally replaced by a carbonyl group;
$R^8$ is selected from the group consisting of: hydrogen, $C_{1-6}$ alkyl, $C(=O)R^9$, and $S(O_2)R^9$;
$R^9$ is $C_{1-6}$ alkyl or $C_{3-7}$ cycloalkyl;
V is a $C_{1-4}$ alkylene, wherein each carbon atom is optionally substituted by one or two substituents independently selected from the group consisting of:
hydroxy,
$C_{1-6}$ alkyl,
$C_{1-6}$ alkoxy,
hydroxy-$C_{1-6}$ alkyl,
$C_{1-6}$ alkoxy-$C_{1-6}$ alkyl,
halogen, and
halo $C_{1-6}$ alkyl;
W is selected from the group consisting of: a bond, $CH_2$ and $C(=O)$;
n is 0 or 1;
each $R^d$ is independently selected from the group consisting of: hydroxy, cyano, $NR^aR^b$, halogen, $C_{1-6}$ alkyl, halo $C_{1-6}$ alkyl, hydroxy $C_{1-6}$ alkyl, $C_{1-6}$ alkoxy, $C_{1-6}$ alkoxy $C_{1-6}$ alkyl, $C_{3-7}$ cycloalkyl, $C_{1-6}$ alkoxycarbonyl, acyl, —C(O)$NR^aR^b$, —$NR^a$—C(O)—$R^b$, —$NR^a$—C(O)—$OR^b$, —$NR^a$—C(O)—$NR^b$, —$NR^a$—$SO_2$—$R^b$, —$NR^a$—$SO_2$—$NR^bR^c$, —OC(O)$NR^aR^b$, —OC(O)$OR^a$, $C_{1-6}$ alkylsulfonyl, $C_{1-6}$ alkylsulfinyl, $C_{1-6}$ alkylthio, phenyl, phenyl $C_{1-3}$ alkyl, heteroaryl, heteroaryl $C_{1-3}$ alkyl and heterocyclyl, and said phenyl, the phenyl of said phenyl $C_{1-3}$ alkyl, said heteroaryl, the heteroaryl of heteroaryl $C_{1-3}$ alkyl, and said heterocyclyl are optionally substituted by one to three substituents independently selected from the group consisting of hydroxy, cyano, $NR^aR^b$, halogen, $C_{1-6}$ alkyl, halo $C_{1-6}$ alkyl, hydroxy $C_{1-6}$ alkyl, $C_{1-6}$ alkoxycarbonyl, acyl, —C(O)$NR^aR^b$, —$NR^a$—C(O)—$R^b$, —$NR^a$—C(O)—$OR^b$, —$NR^a$—C(O)—$NR^b$, —$NR^a$—$SO_2$—$R^b$, —$NR^a$—$SO_2$—$NR^bR^c$, —OC(O)$NR^aR^b$, —OC(O)$OR^a$, $C_{1-6}$ alkylsulfonyl, $C_{1-6}$ alkylsulfinyl and $C_{1-6}$ alkylthio, and one or two ring carbon atoms of said heterocyclyl is optionally replaced with a carbonyl group; and
$R^a$, $R^b$ and $R^c$ are independently hydrogen or $C_{1-6}$ alkyl;
or a prodrug or pharmaceutically acceptable salt thereof.

Further, the invention is concerned with a process and an intermediate for the manufacture of the above compounds, pharmaceutical preparations which contain such compounds, the use of these compounds for the production of pharmaceutical preparations.

DETAILED DESCRIPTION OF THE INVENTION

Unless otherwise indicated, the following definitions are set forth to illustrate and define the meaning and scope of the various terms used to describe the invention herein.

The term "halogen", "halogen atom" or "halo" refers to fluoro, chloro, bromo or iodo. Preferred "halogen" groups are fluoro or chloro.

The term "$C_{1-6}$ alkyl", alone or in combination with other groups, means a branched or straight-chain monovalent alkyl radical, having one to six carbon atoms. This term is further exemplified by such radicals as methyl, ethyl, n-propyl, isopropyl, n-butyl, s-butyl, t-butyl. $C_{1-4}$ alkyl or $C_{1-3}$ alkyl is more preferred. The term "$C_{2-6}$ alkyl" means the same as a "$C_{1-6}$ alkyl", except that the $C_{2-6}$ alkyl has two to six carbon atoms; and the term "$C_{3-6}$ alkyl" means the same as a "$C_{1-6}$ alkyl", except that the $C_{3-6}$ alkyl has three to six carbon atoms; etc. The term "$C_{1-20}$ alkyl" means the same as a "$C_{1-6}$ alkyl", except that the $C_{1-20}$ alkyl has one to 20 carbon atoms.

The term "$C_{1-20}$ alkylcarbonyloxy-$C_{1-6}$ alkyl" refers to the group $R^{b1}$—C(O)—O—$R^{b2}$—, wherein $R^{b2}$ is a $C_{1-6}$ alkylene and $R^{b1}$ is a $C_{1-20}$ alkyl, as defined above.

The term "$C_{1-20}$ alkoxycarbonyloxy-$C_{1-6}$ alkyl" refers to the group $R^{a3}$—C(O)—O—$R^{b3}$—, wherein $R^{b3}$ is a $C_{1-6}$ alkylene and $R^{a3}$ is a $C_{1-20}$ alkoxy, as defined above.

The term "$C_{1-6}$ alkoxy," alone or in combination with other groups, means the group R'—O—, wherein R' is a $C_{1-6}$ alkyl.

The term "$C_{1-6}$ alkoxy-carbonyl" refers to the group $R^{a1}$—C(O)—, wherein $R^{a1}$ is a $C_{1-6}$ alkoxy as defined above.

The term "$C_{1-6}$ alkoxy-$C_{1-6}$ alkyl" means a $C_{1-6}$ alkyl substituted by a $C_{1-6}$ alkoxy group, as defined herein.

The term "$C_{1-6}$ alkoxy-carbonyloxy" refers to the group $R^{a1}$—C(O)—O—, wherein $R^{a1}$ is a $C_{1-6}$ alkoxy as defined above.

The term "aryl", alone or combination with other groups, means cyclic aromatic hydrocarbon radical consisting of one or more fused rings containing 6-14 carbon atoms, for example phenyl or naphthyl. The term "arylmethyl" preferably means a phenyl-$CH_2$— or a naphthyl-$CH_2$ radical.

The term "phenyl-$C_{1-3}$ alkyl" means a $C_{1-3}$ alkyl, as defined herein, substituted by phenyl.

The term "arylcarbonyloxy-$C_{1-6}$ alkyl" refers to the group $R^{c1}$—C(O)—O—$R^{c2}$—, wherein $R^{c2}$ is a $C_{1-6}$ alkylene and $R^{c1}$ is an aryl, as defined above The term "$C_{3-6}$ alkenyl", alone or in combination with other groups, means a straight-chain or branched hydrocarbon residue comprising a carbon-carbon double bond, having three to six carbon atoms, provided that the carbon atom of the attachment point of the $C_{3-6}$ alkenyl to the rest of the molecule is not bonded to another carbon atom of the $C_{3-6}$ alkenyl by a carbon-carbon double bond. An example of a $C_{3-6}$ alkenyl is 2-propenyl.

The term "$C_{1-6}$ alkylene", alone or in combination with other groups, means a branched or straight-chain saturated divalent hydrocarbon radical of one to six carbon atoms, such as methylene, ethylene, tetramethylethylene.

The term "$C_{3-6}$-alkynyl", alone or in combination with other groups, means a straight-chain or branched hydrocarbon residue comprising a carbon-carbon triple bond, having three to six carbon atoms, provided that the carbon atom of the attachment point of the $C_{3-6}$ alkynyl to the rest of the molecule is not bonded to another carbon atom of the $C_{3-6}$ alkynyl by a carbon-carbon triple bond. An example of a $C_{3-6}$ alkynyl is 2-propynyl.

The term "carboxyl" refers to a group —C(O)OH.

The term "carbamoyl" refers to a group —C(O)NH$_2$.

The term "$C_{3-7}$ cycloalkyl," alone or in combination with other groups, means a saturated monovalent mono-cyclic hydrocarbon radical of three to seven ring carbons (e.g., cyclopropyl, cyclobutyl, or cyclohexyl).

The term "$C_{3-7}$ cycloalkyl $C_{1-6}$ alkyl" means a $C_{1-6}$ alkyl substituted by one or more, preferably one or two, $C_{3-7}$ cycloalkyl groups, as defined herein.

The term "$C_{7-10}$ bicycloalkyl," alone or in combination with other groups, means a saturated monovalent cyclic hydrocarbon radical of seven to ten ring carbons, having two rings, in which two or more ring carbon atoms of one ring are ring carbon atoms of the other ring (e.g., bicyclo[2.2.1]heptyl).

The term "halo $C_{1-6}$ alkoxy," alone or in combination with other groups, means a $C_{1-6}$ alkoxy substituted by one or more halogens. In particular embodiments the $C_{1-6}$ alkoxy is substituted by one to three halogens.

The term "halo $C_{1-6}$ alkyl" means a $C_{1-6}$ alkyl substituted by one or more of the same or different halogen atoms. Examples are 1-fluoromethyl, difluoromethyl, trifluoromethyl, 1-fluoroethyl, 2-fluoroethyl and 2,2,2-trifluoroethyl. The most preferred "halo $C_{1-6}$ alkyl" is trifluoromethyl.

The term "heteroaryl," alone or combination with other groups, means an aromatic monocyclic- or bicyclic-aromatic radical of 5 to 10 ring atoms having one to three ring heteroatoms independently selected from N, O, and S, with the remaining ring atoms being C. More specifically the term "heteroaryl" includes, but is not limited to, pyridyl, furanyl, thienyl, thiazolyl, isothiazolyl, triazolyl, imidazolyl, isoxazolyl, pyrrolyl, pyrimidinyl, pyrazolyl, pyrazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]-pyridinyl, imidazo[2,1-b]thiazolyl, and the derivatives thereof. The most preferred heteroaryl are isoquinolyl, pyridyl, and quinolyl. The term "heteroarylmethyl"means a heteroaryl-CH$_2$-radical.

The term "heteroaryl-$C_{1-3}$ alkyl" means a $C_{1-3}$ alkyl substituted by a heteroaryl, as defined herein.

The term "heterocyclyl", alone or combination with other groups, means a non-aromatic mono- or bi-cyclic radical of four to nine ring atoms in which one to three ring atoms are heteroatoms independently selected from N, O and S(O)$_n$ (where n is an integer from 0 to 2), with the remaining ring atoms being C. The more preferred heterocyclyl is piperidyl or 6-aza-spiro[2,5]oct-6yl.

The term "heterocyclyl-$C_{1-3}$ alkyl" means a $C_{1-3}$ alkyl, substituted by one heterocyclyl, as defined herein.

The term "hydroxy $C_{1-6}$ alkyl" means $C_{1-6}$ alkyl substituted by one or more, preferably one hydroxy group(s).

The term "mono or di-$C_{1-6}$ alkyl substituted aminocarbonyl" refers to a group —OC(O)NR$^{b1}$R$^{c1}$ wherein at least one of R$^{b1}$ and R$^{c1}$ is $C_{1-6}$ alkyl and the other is hydrogen or $C_{1-6}$ alkyl.

The term "mono or di-$C_{1-6}$ alkyl substituted aminocarbonyloxy" refers to a group —OC(O)NR$^{v1}$R$^{v2}$ wherein at least one of R$^{v1}$ and R$^{v2}$ is $C_{1-6}$ alkyl and the other is hydrogen or $C_{1-6}$ alkyl.

The term "acyl" means R—C(O)—, in which R is a $C_{1-6}$ alkyl, halo $C_{1-6}$ alkyl, $C_{3-7}$ cycloalkyl or $C_{3-7}$ cycloalkyl $C_{1-6}$ alkyl.

The term "mono or di-$C_{1-6}$ alkyl substituted aminocarbonyloxy-$C_{1-6}$ alkyl" means $C_{1-6}$ alkyl substituted by a mono or di-$C_{1-6}$ alkyl substituted aminocarbonyloxy, as defined above.

The term, "$C_{1-6}$ alkylsulfonyl", "$C_{1-6}$ alkylsulfinyl" and "$C_{1-6}$ alkylthio" means a $C_{1-6}$ alkyl-SO$_2$—, $C_{1-6}$ alkyl-SO— and $C_{1-6}$ alkyl-S—, respectively.

Preferred radicals for the chemical groups whose definitions are given above are those specifically exemplified in the Examples.

"Optional" or "optionally" means that the subsequently described event or circumstance may but need not occur, and that the description includes instances where the event or circumstance occurs and instances in which it does not. For example, an "aryl group optionally substituted with an alkyl group" means that the alkyl may but need not be present, and the description includes situations where the aryl group is substituted with an alkyl group and situations where the aryl group is not substituted with the alkyl group.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 kg, a daily dosage of about 0.1 mg to about 5,000 mg, preferably from about 0.1 mg to about 1,000 mg, more preferably from about 0.5 to 500 mg, and more preferably from about 1 mg to 100 mg, should be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

Unless otherwise indicated, the term "a compound of the formula" or "a compound of formula" or "compounds of the formula" or "compounds of formula" refers to any compound selected from the genus of compounds as defined by the formula.

Compounds of formula (I) can form pharmaceutically acceptable acid addition salts.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^2$) occurs more than one time in any moiety or formula depicting and describing compounds employed or claimed in the present invention, its definition on each occurrence is independent of its definition at every other occurrence. Also, combinations of substituents and/or variables are permissible only if such compounds result in chemically stable compounds.

The present invention relates to a compound according to formula (I)

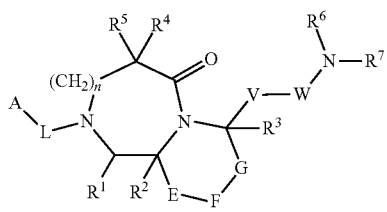

(I)

wherein

A is selected from the group consisting of: aryl, heteroaryl, arylmethyl and heteroarylmethyl, wherein the said aryl, heteroaryl and the aryl of arylmethyl are optionally substituted by one to three substituents independently selected from the group consisting of halogen, aryl, heteroaryl, $C_{1-6}$ alkyl, halo$C_{1-6}$ alkyl, $C_{1-6}$ alkoxy and halo $C_{1-6}$ alkoxy;

E is $CH_2$ or O;

F is selected from the group consisting of: $CH_2$, O, $N(R^8)$, S, SO and $SO_2$;

G is selected from the group consisting of: a single bond, $CH_2$, and $CH_2CH_2$, with the proviso that, when E is O, then F is not O, S, SO or $SO_2$;

L is selected from the group consisting of: a bond, NH—C(=O), NH—C(=S), and CH=CH—C(=O);

$R^1$, $R^2$ and $R^3$ are independently of each other selected from the group consisting of:
hydrogen,
$C_{1-6}$ alkyl, which is optionally substituted by one to three substituents independently selected from the group consisting of hydroxy, $C_{1-6}$ alkoxy, carboxyl, carbamoyl, mono or di-$C_{1-6}$ alkyl substituted aminocarbonyl and $C_{1-6}$ alkoxycarbonyl, aryl and heteroaryl, wherein said heteroaryl and aryl are optionally substituted by one to three substituents independently selected from the group consisting of halogen, $C_{1-6}$ alkyl, halo $C_{1-6}$ alkyl, $C_{1-6}$ alkoxy and halo $C_{1-6}$ alkoxy,
$C_{3-7}$ cycloalkyl, and
aryl;

$R^4$ and $R^5$ are independently of each other selected from the group consisting of:
hydrogen,
$C_{1-6}$ alkyl, which is optionally substituted by one to three substituents independently selected from the group consisting of amino, hydroxy, carboxyl, carbamoyl, mono or di-$C_{1-6}$ alkyl substituted aminocarbonyl and $C_{1-6}$ alkoxycarbonyl, and
$C_{3-7}$ cycloalkyl, which is optionally substituted by one to three substituents independently selected from the group consisting of amino, hydroxy, carboxyl, carbamoyl, mono or di-$C_{1-6}$ alkyl substituted aminocarbonyl and $C_{1-6}$ alkoxycarbonyl; or $R^4$ and $R^5$, together with the carbon atom to which they are attached, form $C_{3-7}$ cycloalkyl or heterocyclyl which is optionally substituted by one to three substituents independently selected from the group consisting of $C_{1-4}$ alkyl, halo $C_{1-4}$ alkyl and halogen;

$R^6$ and $R^7$ are, independently of each other selected from the group consisting of:
$C_{1-6}$ alkyl,
$C_{3-6}$ alkenyl,
$C_{3-6}$ alkynyl,
hydroxy $C_{2-6}$ alkyl,
$C_{1-6}$ alkoxy $C_{2-6}$ alkyl,
$C_{3-7}$ cycloalkyl, which is optionally substituted by one to three $R^d$ groups,
$C_{3-7}$ cycloalkyl $C_{1-6}$ alkyl, wherein the cycloalkyl is optionally substituted by one to three $R^d$ groups,
$C_{7-10}$ bicycloalkyl,
phenyl $C_{1-3}$ alkyl, wherein the phenyl is optionally substituted by one to three $R^d$ groups,
heteroaryl $C_{1-3}$ alkyl, wherein the heteroaryl is optionally substituted by one to three $R^d$ groups,
Heterocyclyl which is optionally substituted by one to three $R^d$ groups, and
heterocyclyl $C_{1-6}$ alkyl, wherein the heterocyclyl is optionally substituted by one to three $R^d$ groups; or $R^6$ and $R^7$, together with the nitrogen atom to which they are attached, form heterocyclyl optionally substituted by one to three $R^d$ groups, and wherein one of the ring carbon atoms of said heterocyclyl formed by $R^6$ and $R^7$ is optionally replaced with a carbonyl group or $SO_2$;

and/or one of the ring carbon atoms of the heterocyclyl formed by $R^6$ and $R^7$ is also a ring carbon atom of a second ring which is $C_{3-7}$ cycloalkyl or heterocyclyl, which is optionally substituted by $C_{1-6}$ alkyl and wherein one or two ring carbon atoms of said second ring is optionally replaced by a carbonyl group;

$R^8$ is selected from the group consisting of: hydrogen, $C_{1-6}$ alkyl, $C(=O)R^9$, and $S(O_2)R^9$;

$R^9$ is $C_{1-6}$ alkyl or $C_{3-7}$ cycloalkyl;

V is a $C_{1-4}$ alkylene, wherein each carbon atom is optionally substituted by one or two substituents independently selected from the group consisting of:
hydroxy, $C_{1-6}$ alkyl,
$C_{1-6}$ alkoxy,
hydroxy-$C_{1-6}$ alkyl,
$C_{1-6}$ alkoxy-$C_{1-6}$ alkyl,
halogen, and
halo $C_{1-6}$ alkyl;

W is selected from the group consisting of: a bond, $CH_2$ and C(=O);

n is 0 or 1;

each $R^d$ is independently selected from the group consisting of: hydroxy, cyano, $NR^aR^b$, halogen, $C_{1-6}$ alkyl, halo $C_{1-6}$ alkyl, hydroxy $C_{1-6}$ alkyl, $C_{1-6}$ alkoxy, $C_{1-6}$ alkoxy $C_{1-6}$ alkyl, $C_{3-7}$ cycloalkyl, $C_{1-6}$ alkoxycarbonyl, acyl, —C(O)$NR^aR^b$, —$NR^a$—C(O)—$R^b$, —$NR^a$—C(O)—$OR^b$, —$NR^a$—C(O)—$NR^b$, —$NR^a$—$SO_2$—$R^b$, —$NR^a$—$SO_2$—$NR^bR^c$, —OC(O)$NR^aR^b$, —OC(O)$OR^a$, $C_{1-6}$ alkylsulfonyl, $C_{1-6}$ alkylsulfinyl, $C_{1-6}$ alkylthio, phenyl, phenyl $C_{1-3}$ alkyl, heteroaryl, heteroaryl $C_{1-3}$ alkyl and heterocyclyl, and said phenyl, the phenyl of said phenyl $C_{1-3}$ alkyl, said heteroaryl, the heteroaryl of heteroaryl $C_{1-3}$ alkyl, and said heterocyclyl are optionally substituted by one to three substituents independently selected from the group consisting of hydroxy, cyano, $NR^aR^b$, halogen, $C_{1-6}$ alkyl, halo $C_{1-6}$ alkyl, hydroxy $C_{1-6}$ alkyl, $C_{1-6}$ alkoxycarbonyl, acyl, —C(O)$NR^aR^b$, —$NR^a$—C(O)—$R^b$, —$NR^a$—C(O)—$OR^b$, —$NR^a$—C(O)—$NR^b$, —$NR^a$—$SO_2$—$R^b$, —$NR^a$—$SO_2$—$NR^bR^c$, —OC(O)$NR^aR^b$, —OC(O)$OR^a$, $C_{1-6}$ alkylsulfonyl, $C_{1-6}$ alkylsulfinyl and $C_{1-6}$ alkylthio, and one or two ring carbon atoms of said heterocyclyl is optionally replaced with a carbonyl group; and $R^a$, $R^b$ and $R^c$ are independently hydrogen or $C_{1-6}$ alkyl;

or a prodrug or pharmaceutically acceptable salt thereof.

The compounds of formula (I) are CCR2 receptor antagonists, with some antagonist activity also at CCR3 and CCR5.

Certain compounds of formula (I) may exist in more than one tautomeric form. The present invention encompasses all such tautomers, as well as mixtures thereof. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers.

The compounds of formula (I) possess two or more asymmetric centers. Unless indicated otherwise, the description or naming of a particular compound in the specification and claims is intended to include both individual enantiomers and mixtures, racemic or otherwise, thereof, as well as individual epimers and mixture thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

While the broadest definition of this invention is described before, certain compounds of formula (I) are preferred.

i) In the compounds of formula (I), A is phenyl or naphthyl, wherein said phenyl and said naphthyl are optionally substituted by one to three substituents selected from the group consisting of halogen, halo $C_{1-6}$ alkyl, halo $C_{1-6}$ alkoxy and aryl. Preferably, A is phenyl substituted by one or two substituents selected from the group consisting of halogen atoms and trifluoromethyl, more preferably the substituents are independently selected from the group consisting of chlorine, fluorine and trifluoromethyl. A is especially 3-fluoro-phenyl, 3-chloro-4-trifluoromethyl-phenyl and 3,4-dichlorophenyl. A is in particular 3-chloro-4-trifluoromethyl-phenyl or 3,4-dichlorophenyl ii) In the compounds of formula (I), $R^6$ and $R^7$, together with the nitrogen atom to which they are attached, form heterocyclyl optionally substituted by one to three substituents independently selected from the group consisting of halogen, hydroxy, $C_{1-6}$ alkyl and hydroxy $C_{1-6}$ alkyl; and/or one of the ring carbon atoms of the heterocyclyl formed by $R^6$ and $R^7$ is also a ring carbon atom of another ring which is $C_{3-7}$ cycloalkyl or cycloheteroalkyl.

The heterocyclyl formed by $R^6$ and $R^7$, together with the nitrogen atom to which it is attached, is preferably piperidyl or pyrrolidinyl, and said piperidyl and pyrrolidinyl being optionally substituted by one or two substituents independently selected from the group consisting of hydroxy, $C_{1-6}$ alkyl and hydroxy $C_{1-6}$ alkyl, and/or one of the ring carbon atoms of said piperidyl and pyrrolidinyl formed by $R^6$ and $R^7$ is also shared by a $C_{3-7}$ cycloalkyl ring.

More preferably, in the compounds of formula (I), $R^6$ and $R^7$ together with the nitrogen atom to which they are attached form a mono spiro-heterocyclyl such as 6-aza-spiro[2,5]oct-6-yl, 5-azaspiro[2.5]oct-5-yl, 7-aza-spiro[3.5]non-7-yl, 8-aza-spiro[4.5]dec-8-yl, 1,8-diaza-spiro[4.5]dec-8-yl, 1,3,8-triaza-spiro[4.5]dec-8-yl, 2,8-diaza-spiro[4.5]dec-8-yl, 1-oxa-3,8-diaza-spiro[4.5]dec-8-yl, 1-oxa-8-aza-spiro[4.5]dec-8-yl, 2-oxa-8-aza-spiro[4.5]dec-8-yl, 2-oxa-7-aza-spiro[3.5]non-7-yl, 1-oxa-7-aza-spiro[3.5]non-7-yl, 9-aza-spiro[5.5]undec-9-yl, 1-oxa-4,9-diaza-spiro[5.5]undec-9-yl, wherein the spiro-heterocyclyl ring is optionally substituted by one to three substituents independently selected from the group consisting of hydroxy, oxo, alkoxy, fluorine and $C_{1-6}$ alkyl. In particular, the spiro heterocyclyl is 6-aza-spiro[2,5]oct-6-yl wherein the spiro-heterocyclyl ring is optionally substituted by one to two substituents independently selected from the group consisting of fluoro, hydroxy and $C_{1-6}$ alkyl.

Most preferably the spiro heterocyclyl is 6-aza-spiro[2,5]oct-6-yl wherein the spiro-heterocyclyl ring is optionally substituted by one to two substituents independently selected from the group consisting of hydroxy or $C_{1-6}$ alkyl.

In the compounds of formula (I), $R^6$ and $R^7$ together with the nitrogen atom to which they are attached form especially (S)-4-hydroxy-6-aza-spiro[2,5]oct-6-yl.

iii) In the compounds of formula (I), n is preferably 0.

iv) The compounds of formula (I), wherein V is $C_{1-2}$ alkylene.

v) In the compounds of formula (I), wherein $R^1$, $R^2$, $R^3$, $R^4$ and $R^5$ are independently hydrogen or $C_{1-6}$ alkyl. Preferably, one of $R^4$ and $R^5$ is hydrogen or $C_{1-6}$ alkyl, the other is hydrogen, $R^1$ and $R^3$ are hydrogen and $R^2$ is hydrogen or $C_{1-6}$ alkyl. More preferably, one of $R^4$ or $R^5$ is methyl and the other is hydrogen, and $R^1$, $R^2$ and $R^3$ are hydrogen.

vi) In the compounds of formula (I), L is preferably NH—C(=O) or CH=CH—C(=O). Most preferably L is NH—C(=O).

vii) In the compounds of formula (I), preferably E and F are independently O or $CH_2$ with the proviso that when E is O then F is not O.

viii) In the compounds of formula (I), G is preferably single bond or CH₂.

ix) the compounds of formula (I), wherein $R^4$ is methyl, $R^1$, $R^2$, $R^3$ and $R^5$ are hydrogen, L is NHC(=O), V is $C_{1-2}$ alkylene and $R^6$ and $R^7$ together with the nitrogen atom to which they are attached form (S)-4-hydroxy-6-aza-spiro[2,5]oct-6-yl.

x) Preferred compound of the invention is a compound of formula (I), which is selected from the group consisting of:

(3S,6S,8aS)-3-[2-((S)-4-Hydroxy-6-aza-spiro[2.5]oct-6-yl)-ethyl]-6-methyl-5-oxo-hexahydro-oxazolo[3,2-a]pyrazine-7-carboxylic acid (3,4-dichloro-phenyl)-amide, (3S,6S,8aR)-3-[2-((S)-4-Hydroxy-6-aza-spiro[2.5]oct-6-yl)-ethyl]-6-methyl-5-oxo-hexahydro-oxazolo[3,2-a]pyrazine-7-carboxylic acid (3,4-dichloro-phenyl)-amide, (3S,6S,8aR)-3-[3-((S)-4-Hydroxy-6-aza-spiro[2.5]oct-6-yl)-3-oxo-propyl]-6-methyl-5-oxo-hexahydro-oxazolo[3,2-a]pyrazine-7-carboxylic acid (3-chloro-4-trifluoromethyl-phenyl)-amide, (4S,7S)-4-((S)-4-Hydroxy-6-aza-spiro[2.5]oct-6-ylmethyl)-7-methyl-6-oxo-hexahydro-pyrazino[2,1-b][1,3]oxazine-8-carboxylic acid (3,4-dichloro-phenyl)-amide, (4S,7S,9aR)-4-[2-((S)-4-Hydroxy-6-aza-spiro[2.5]oct-6-yl)-ethyl]-7-methyl-6-oxo-hexahydro-pyrazino[2,1-c][1,4]oxazine-8-carboxylic acid (3,4-dichloro-phenyl)-amide, (4S,7S,9aR)-4-[2-((S)-4-Hydroxy-6-aza-spiro[2.5]oct-6-yl)-ethyl]-7-methyl-6-oxo-hexahydro-pyrazino[2,1-c][1,4]oxazine-8-carboxylic acid (3-chloro-4-trifluoromethyl-phenyl)-amide, (3S,6R,8aS)-6-[2-((S)-4-Hydroxy-6-aza-spiro[2.5]oct-6-yl)-ethyl]-3-methyl-4-oxo-hexahydro-pyrrolo[1,2-a]pyrazine-2-carboxylic acid (3,4-dichloro-phenyl)-amide, (3S,6S,8aR)-3-[3-((S)-4-Hydroxy-6-aza-spiro[2.5]oct-6-yl)-3-oxo-propyl]-6-methyl-5-oxo-hexahydro-oxazolo[3,2-a]pyrazine-7-carboxylic acid (3,4-dichloro-phenyl)-amide, (3S,6R,8aS)-6-[3-((S)-4-Hydroxy-6-aza-spiro[2.5]oct-6-yl)-3-oxo-propyl]-3-methyl-4-oxo-hexahydro-pyrrolo[1,2-a]pyrazine-2-carboxylic acid (3-chloro-4-trifluoromethyl-phenyl)-amide, (4S,7S,9aR)-4-[3-((S)-4-Hydroxy-6-aza-spiro[2.5]oct-6-yl)-3-oxo-propyl]-7-methyl-6-oxo-hexahydro-pyrazino[2,1-c][1,4]oxazine-8-carboxylic acid (3,4-dichloro-phenyl)-amide, (4S,7S,9aR)—N-(3-chloro-4-(trifluoromethyl)phenyl)-4-(3-((S)-4-hydroxy-6-azaspiro[2.5]octan-6-yl)-3-oxopropyl)-7-methyl-6-oxohexahydropyrazino[2,1-c][1,4]oxazine-8(1H)-carboxamide, (4S,7S,9aR)—N-(3,4-dichlorophenyl)-4-(2-(4,4-difluoro-6-azaspiro[2.5]octan-6-yl)ethyl)-7-methyl-6-oxohexahydropyrazino[2,1-c][1,4]oxazine-8(1H)-carboxamide, (3S,6R,9aS)-6-[3-((S)-4-Hydroxy-6-aza-spiro[2.5]oct-6-yl)-3-oxo-propyl]-3-methyl-4-oxo-octahydro-pyrido[1,2-a]pyrazine-2-carboxylic acid (3,4-dichloro-phenyl)-amide, (3S,6R,9aS)-6-[3-((S)-4-Hydroxy-6-aza-spiro[2.5]oct-6-yl)-3-oxo-propyl]-3-methyl-4-oxo-octahydro-pyrido[1,2-a]pyrazine-2-carboxylic acid (3-chloro-4-trifluoromethyl-phenyl)-amide, (3S,6R,9aS)-6-[2-((S)-4-Hydroxy-6-aza-spiro[2.5]oct-6-yl)-ethyl]-3-methyl-4-oxo-octahydro-pyrido[1,2-a]pyrazine-2-carboxylic acid (3,4-dichloro-phenyl)-amide, (3S,6R,9aS)-6-[2-((S)-4-Hydroxy-6-aza-spiro[2.5]oct-6-yl)-ethyl]-3-methyl-4-oxo-octahydro-pyrido[1,2-a]pyrazine-2-carboxylic acid (3-chloro-phenyl)-amide, and (3S,6R,9aS)-6-[2-((S)-4-Hydroxy-6-aza-spiro[2.5]oct-6-yl)-ethyl]-3-methyl-4-oxo-octahydro-pyrido[1,2-a]pyrazine-2-carboxylic acid (3-fluoro-phenyl)-amide.

In another embodiment the invention provides a compound of formula (I'):

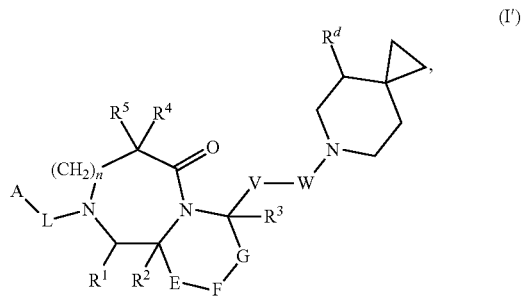

wherein A, L, E, F, G, V, W, n, $R^1$, $R^2$, $R^3$, $R^4$, $R^5$, $R^d$ are as defined above.

In another embodiment the invention provides a compound of formula (I"):

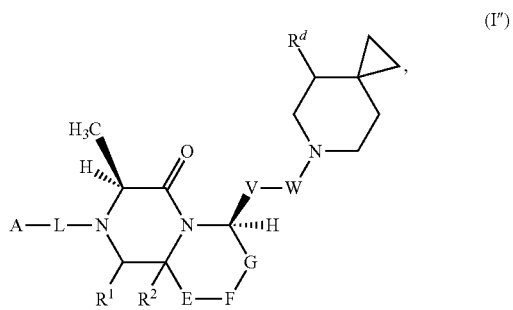

wherein A, L, E, F, G, V, W, $R^1$, $R^2$, $R^d$ are as defined above.

General Synthetic Procedures

Compounds of formula (I) in which L is NH—C(=O) are represented by formula (Ia). A, E, F, G, $R^1$, $R^2$, $R^3$, $R^4$, $R^5$, $R^6$, $R^7$, V, W and n are as defined before.

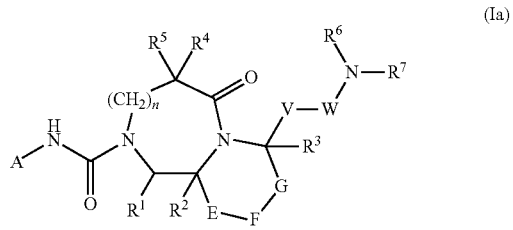

Compounds of formula (Ia) can be from secondary amine 1 by reaction with an isocyanate of the general formula A-N=C=O or a phenyl carbamate of the general formula A-NH—C(=O)—O-Ph. A, E, F, G, $R^1$, $R^2$, $R^3$, $R^4$, $R^5$, $R^6$, $R^7$, V, W and n are as defined before.

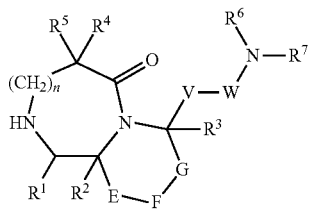

(1)

The reaction is typically carried out in aprotic solvents such as dichloromethane, tetrahydrofuran, N,N-dimethylformamide, N-methylpyrrolidinone, dimethyl sulfoxide, acetonitrile and mixtures thereof at temperatures between 0° C. and 120° C. in the presence or absence of a base such as triethylamine, diisopropylethylamine, 4-methylmorpholine, and/or 4-(dimethylamino)pyridine. Isocyanates of the general formula A-N=C=O or phenyl carbamates A-NH—C(=O)—O-Ph are commercially available or can be synthesized by methods known in the art. For instance, isocyanates A-N=C=O can be synthesized from the corresponding arylamines A-NH$_2$ by reaction with phosgene, diphosgene, or triphosgene, in the presence of a base such as pyridine, in a solvent like tetrahydrofuran at temperatures between 0° C. and 70° C. Phenyl carbamates A-NH—C(=O)—O-Ph can be prepared from the corresponding arylamines A-NH$_2$ by reaction with phenyl chloroformate, in a solvent such as tetrahydrofuran, at temperatures between −20° C. and 20° C.

Compounds of formula (I) in which L is NH—C(=S) are represented by formula (Ib). A, E, F, G, R$^1$, R$^2$, R$^3$, R$^4$, R$^5$, R$^6$, R$^7$, V, W and n are as defined before.

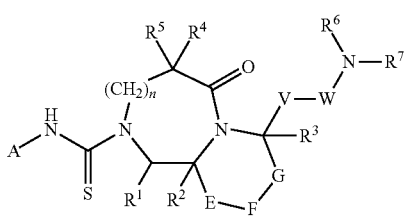

(Ib)

Compounds of formula (Ib) can be from secondary amine 1 by reaction with a isothiocyanate of the general formula A-N=C=S. The reaction is typically carried out in aprotic solvents such as dichloromethane, tetrahydrofuran, N,N-dimethylformamide, N-methylpyrrolidinone, dimethyl sulfoxide, acetonitrile and mixtures thereof at temperatures between 0° C. and 120° C. in the presence or absence of a base such as triethylamine, diisopropylethylamine, 4-methylmorpholine, and/or 4-(dimethylamino)pyridine. Isothiocyanates of the general formula A-N=C=S can be synthesized from the corresponding arylamines A-NH$_2$ by reaction with thiophosgene in the presence of a base such as pyridine, in a solvent like tetrahydrofuran at temperatures between 0° C. and 70° C.

Compounds of formula (I) in which L is CH=CH—C(=O) are represented by formula (Ic). A, E, F, G, R$^1$, R$^2$, R$^3$, R$^4$, R$^5$, R$^6$, R$^7$, V, W and n are as defined before.

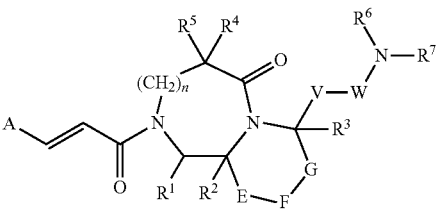

(Ic)

Compounds of formula (Ic) can be from secondary amine 1 by reaction with a cinnamic acid derivative, A-CH=CH—COOH. For instance, the reaction is typically carried out in aprotic solvents such as dichloromethane, tetrahydrofuran, N,N-dimethylformamide, N-methyl-pyrrolidinone and mixtures thereof at temperatures between 0° C. and 80° C. in the presence or absence of a base such as triethylamine, diisopropylethylamine, 4-methylmorpholine, and/or 4-(dimethylamino)pyridine, and in the presence of a coupling agent such as N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate.

Alternatively, this reaction can be performed in two steps involving first formation of the cinnamyl chloride A-CH=CH—COCl, and subsequent coupling reaction with amine 1 in the presence of a base. Typically employed reagents for the formation of the acyl chloride are thionyl chloride, phosphorous pentachloride, oxalyl chloride or cyanuric chloride, and the reaction is generally conducted in the absence of a solvent or in the presence of an aprotic solvent like dichloromethane, toluene or acetone. A base can optionally be added, like for example pyridine, triethylamine, diisopropylethylamine or 4-methylmorpholine, and catalytic amounts of N,N-dimethylformamide may be used. The obtained cinnamylchloride can be isolated or reacted as such with amine 1 in an aprotic solvent, like dichloromethane, tetrahydrofuran or acetone, in the presence of a base. Typical bases are triethylamine, 4-methylmorpholine, pyridine, diisopropylethylamine or 4-(dimethylamino)pyridine or mixtures thereof.

Compounds of formula (I) in which L is a bond are represented by formula (Id). A, E, F, G, R$^1$, R$^2$, R$^3$, R$^4$, R$^5$, R$^6$, R$^7$, V, W and n are as defined before.

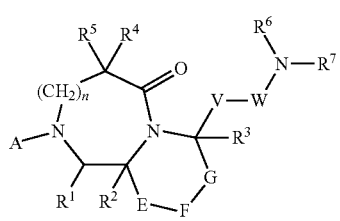

(Id)

Compounds of formula (Id) can be from secondary amine 1 by reaction with halide A-Hal (Hal is F, Cl, Br, or I) or boronic acid A-B(OH)$_2$, using methods and reagents known in the art.

For instance, the reaction can be performed with halide A-Hal at temperatures between 20° C. and 200° C., in the presence of a base, e. g., potassium carbonate, cesium carbonate or triethylamine, in a solvent such as acetonitrile, N,N-dimethylformamide or N-methylpyrrolidinone, optionally under microwave irradiation.

Alternatively, the reaction can be performed with halide A-Hal in the presence of a copper(I) salt, e. g., copper(I) iodide, or copper(I)oxide in the presence of a base, e. g., potassium phosphate, sodium tert-butylate or cesium carbonate, and optionally a diol ligand, e. g., 1,2-ethanediol, in a solvent such as 2-propanol or N-methylpyrrolidinone, at temperatures between 60° C. and 150° C.

Alternatively, the reaction may be performed with halide A-Hal in the presence of a palladium source, e. g., palladium (II)chloride or palladium(II)acetate, and a phosphine ligand, e. g., 2,2'-bis(diphenylphosphino)-1,1'-binaphthyl or 2',4',6'-triisopropyl-1,1'-biphenyl-2-yldicyclohexylphosphine, a base, e. g., potassium phosphate, sodium methylate, or cesium carbonate, in a solvent such as toluene or 1,4-dioxane, at temperatures between 20° C. and 110° C.

Alternatively, the reaction may be performed with boronic acid A-B(OH)$_2$ in the presence of anhydrous copper(II)acetate, in the presence of a base, e. g., triethylamine or pyridine, in a solvent such as dichloromethane, at temperatures between 0° C. and 40° C., optionally in the presence of molecular sieves.

Amines of formula 1 can be synthesised from compounds of formula 2. PG$^1$ is a suitable protective group, e. g., benzyl or benzyloxycarbonyl, E, F, G, R$^1$, R$^2$, R$^3$, R$^4$, R$^5$, R$^6$, R$^7$, V, W and n are as defined before.

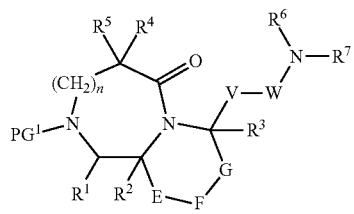

2

The deprotection from 2 to 1 is performed, e. g., by hydrogenation at pressures between 1 bar and 10 bar, in solvents such as methanol, ethanol, tetrahydrofuran, ethyl acetate, or mixtures thereof, in the presence of a suitable catalyst, e. g., palladium on activated charcoal.

Compounds of formula 2 in which W is CH$_2$ are represented by formula 2A. PG$^1$ is a suitable protective group, e. g., benzyl or benzyloxycarbonyl, E, F, G, R$^1$, R$^2$, R$^3$, R$^4$, R$^5$, R$^6$, R$^7$, V and n are as defined before.

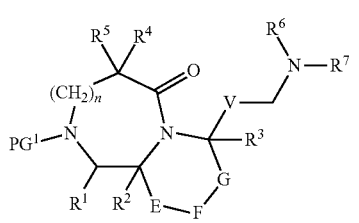

2A

Compounds of formula 2A can be synthesised as described in scheme 1. PG$^1$ is a suitable protective group, e. g., benzyl or benzyloxycarbonyl, E, F, G, V, R$^1$, R$^2$, R$^3$, R$^4$, R$^5$, R$^6$, R$^7$, and n are as defined before.

In scheme 1, step a, alkene 3 is converted to aldehyde 5 using methods and reagents known in the art. For instance, the reaction is performed in with sodium periodate in the presence of catalytic amounts of a suitable osmium source such as osmium(VIII) oxide or potassium osmate(VI) dihydrate, in solvents such as acetone, tert-butylalcohol, water, or mixtures thereof, at temperatures between 0° C. and 30° C.

Alternatively, aldehyde 5 is produced from alcohol 4 using methods and reagents known in the art. For instance, the oxidation is carried out with sodium hypochlorite, in a two-phase mixture of water and dichloromethane, in the presence of sodium hydrogencarbonate and catalytic amounts of sodium bromide or potassium bromide and 2,2,6,6-tetramethylpiperidine-1-oxyl radical, at temperatures between 0° C. and 25° C. Alternatively, the oxidation can be performed with trichloroisocyanuric acid in the presence of catalytic amounts of 2,2,6,6-tetramethylpiperidine-1-oxyl radical, in a solvent such as dichloromethane, at temperatures between 0° C. and 40° C. Alternatively, dimethyl sulfoxide-based reagents can be employed, such as dimethyl sulfoxide-oxalyl chloride, or dimethyl sulfoxide-trifluoroacetic anhydride, in the presence of an organic base such as triethylamine in a solvent such as dichloromethane, at temperatures below 0° C., typically between −78° C. and −60° C.

In scheme 1, step b, aldehyde 5 is converted to amine 2A by reductive amination reaction with amine HN(R$^6$)(R$^7$). The reaction is carried out using a suitable reducing agent, e. g., sodium borohydride, sodium triacetoxyborohydride, sodium cyanoborohydride, or borane pyridine complex, in solvents such as methanol, ethanol, acetic acid, 1,2-dichloroethane, or mixtures thereof, optionally in the presence of a dehydrating agent such as magnesium sulfate, at temperatures between 0° C. and 80° C.

Scheme 1

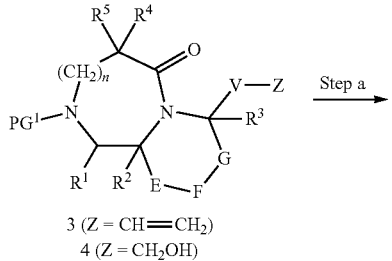

3 (Z = CH=CH$_2$)
4 (Z = CH$_2$OH)

↓ Step b

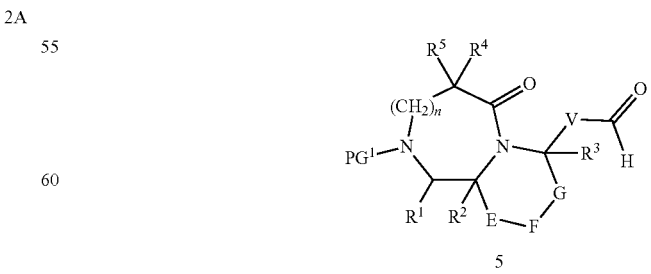

5

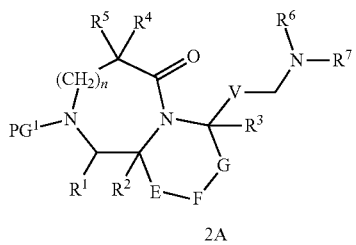

2A

In scheme 1, $PG^1$, E, F, G, V, $R^1$, $R^2$, $R^3$, $R^4$, $R^5$, $R^6$, $R^7$, and n are as defined before.

Compounds of formula 2 in which W is C(=O) are represented by formula 2B. $PG^1$ is a suitable protective group, e. g., benzyl or benzyloxycarbonyl, E, F, G, V, $R^1$, $R^2$, $R^3$, $R^4$, $R^5$, $R^6$, $R^7$, and n are as defined before.

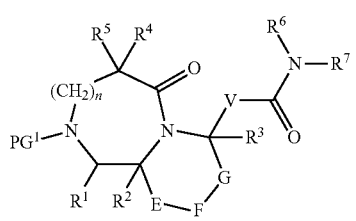

2B

Compounds of formula 2B can be synthesised as described in scheme 2. $PG^1$ is a suitable protective group, e. g., benzyl or benzyloxycarbonyl, E, F, G, $R^1$, $R^2$, $R^3$, $R^4$, $R^5$, $R^6$, $R^7$, V and n are as defined before.

In scheme 2, step a, alkene 3 is oxidised to carboxylic acid 6 using reagents and methods known in the art. For instance, the reaction is performed using sodium periodate in the presence of catalytic amounts of ruthenium(III) chloride, in a solvent mixture composed of carbon tetrachloride, acetonitrile, and water, at temperatures between 0° C. and 40° C.

Alternatively, carboxylic acid 6 is produced from alcohol 4 using reagents and methods known in the art. For instance, the reaction is performed using sodium chlorite in the presence of catalytic amounts of sodium hypochlorite and 2,2,6,6-tetramethylpiperidine-1-oxyl radical, in a buffered (preferably phosphate buffer at pH around 7) solvent mixture of water and acetonitrile, at temperatures between 30° C. and 70° C.

In scheme 2, step b, carboxylic acid 6 is converted to amide 2B by reaction with amine $HN(R^6)(R^7)$, using reagents and methods known in the art. For instance, the reaction is carried out in aprotic solvents such as dichloromethane, tetrahydrofuran, N,N-dimethylformamide, N-methylpyrrolidinone and mixtures thereof at temperatures between 0° C. and 80° C. in the presence or absence of a base such as triethylamine, diisopropylethylamine, or 4-methylmorpholine, and in the presence of a coupling agent such as N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate.

Scheme 2

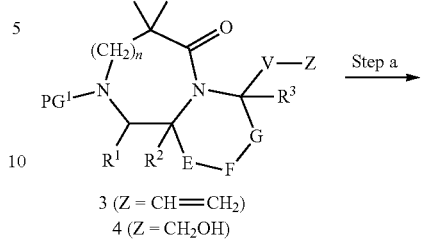

3 (Z = CH=CH$_2$)
4 (Z = CH$_2$OH)

Step a

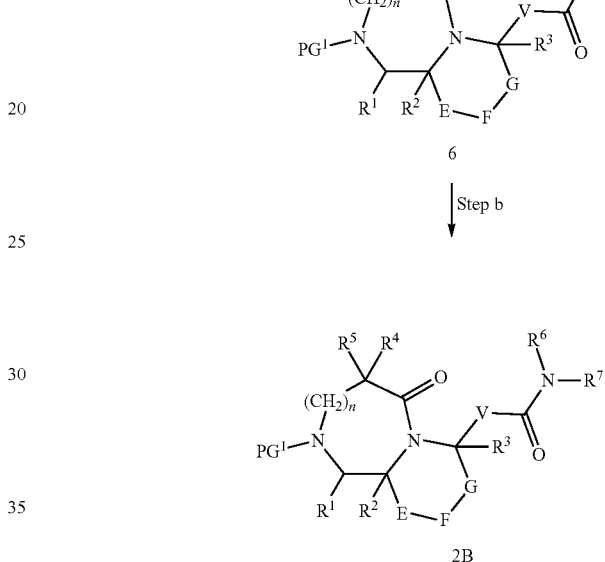

6

Step b

2B

In scheme 2, $PG^1$, E, F, G, V, $R^1$, $R^2$, $R^3$, $R^4$, $R^5$, $R^6$, $R^7$, and n are as defined before.

Compounds of formula 2 in which E is oxygen and F is $CH_2$ are represented by general formula 2C. $PG^1$ is a suitable protective group, e. g., benzyl or benzyloxycarbonyl, G, $R^1$, $R^2$, $R^3$, $R^4$, $R^5$, $R^6$, $R^7$ V, W, and n are as defined before.

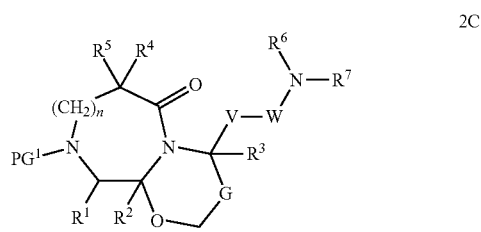

2C

Compounds of formula 2C can be prepared as described in scheme 3. $PG^1$ is a suitable protective group, e. g., benzyl or benzyloxycarbonyl, $R^e$ is lower alkyl, e. g., methyl or ethyl, G, $R^1$, $R^2$, $R^3$, $R^4$, $R^5$, $R^6$, $R^7$ V, W, and n are as defined before. Thus, carbonyl compound 7 reacts in a condensation reaction with amino alcohol 8, leading to amino ester 9, which spontaneously cyclises to bicyclic lactam 2C. The reaction is performed in a suitable solvent, e. g., toluene, at temperatures between 40° C. and the boiling point of the solvent.

Scheme 3

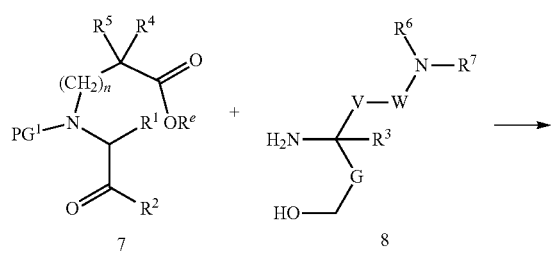

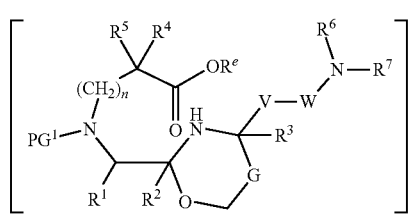

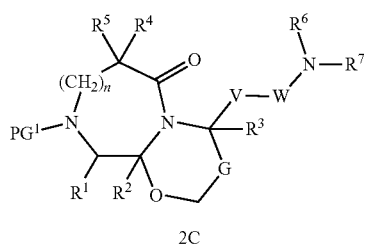

In scheme 3, $PG^1$, G, $R^e$, $R^1$, $R^2$, $R^3$, $R^4$, $R^5$, $R^6$, $R^7$ V, W, and n are as defined before.

Amino alcohols 8 can be prepared as described in the experimental section.

Carbonyl compounds 7 can be synthesised as described in scheme 4. $PG^1$ is a suitable protective group, e.g., benzyl or benzyloxycarbonyl, $R^e$ is methyl, ethyl, or tert-butyl, $R^f$ is lower alkyl, e. g., methyl or ethyl, Hal is chlorine, bromine or iodine, $R^1$, $R^2$, $R^4$ and $R^5$ are as defined before.

In step a, scheme 4, aldehyde or ketone 10 undergoes a reductive amination reaction with amine 11, leading to 12. Suitable reagents for this conversion are borohydride reagents, e. g., sodium borohydride, sodium triacetoxyborohydride, or sodium cyanoborohydride. The reaction is performed solvents such as methanol, dichloromethane, 1,2-dichloroethane, acetic acid, water, or mixtures thereof, at temperatures between −20° C. and 50° C., optionally in the presence of dehydrating agents such as magnesium sulfate or molecular sieves.

In step b, scheme 4, secondary amine 12 is converted to protected derivative 13 using methods and reagents known in the art. For instance, in the case where $PG^1$ is benzyloxycarbonyl, the reaction is performed using benzyl chloroformate in the presence of a base, e. g., sodium hydrogencarbonate, in solvents such as acetone, tetrahydrofuran, water, or mixtures thereof, at temperatures between 0° C. and 30° C.

In step c, scheme 4, the acetal group of 13 is cleaved, leading to carbonyl compound 7. The reaction is performed in the presence of an acidic catalyst, e. g., hydrochloric acid, formic acid, toluene 4-sulfonic acid, or pyridinium toluene 4-sulfonate, in a solvent such as water, methanol, acetone, 2-butanone or mixtures thereof, at temperatures between 0° C. and 100° C.

Scheme 4

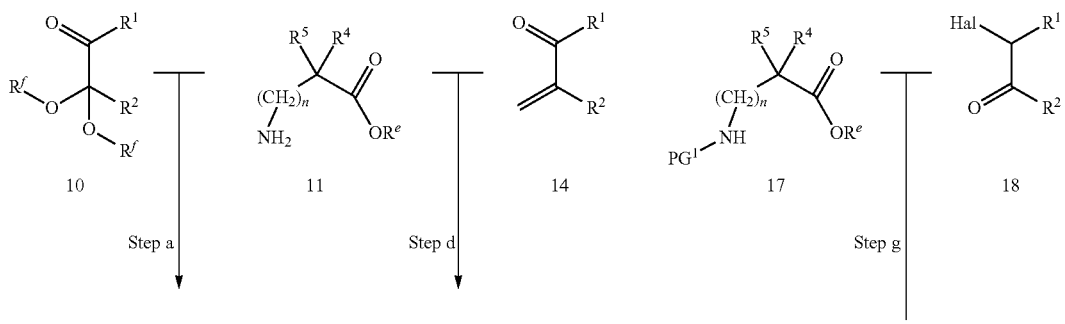

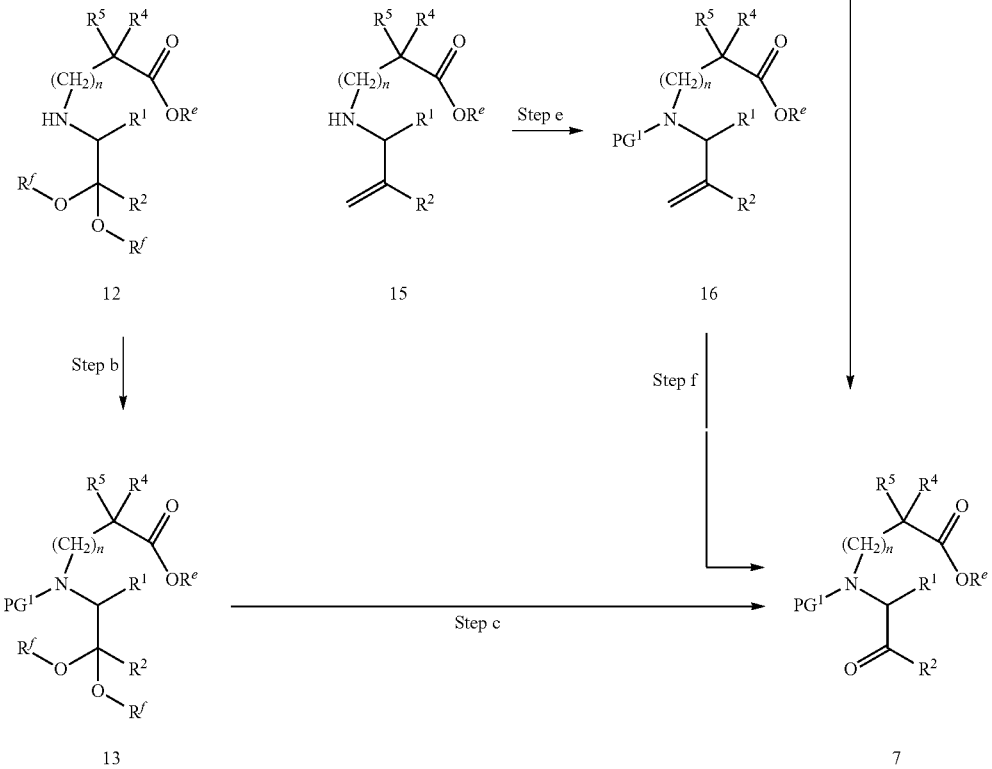

In scheme 4, $PG^1$, $R^e$, $R^f$, $R^1$, $R^2$, $R^4$ and $R^5$ are as defined before. Alternatively, compounds 7 can be synthesised as outlined in scheme 4, steps d-f.

In step d, scheme 4, aldehyde or ketone 14 undergoes a reductive amination reaction with amine 11, leading to 15. This reaction is performed in analogy with scheme 4, step a.

In step e, scheme 4, secondary amine 15 is converted to protected derivative 16. This reaction is performed in analogy with scheme 4, step b.

In step f, scheme 4, the alkene subunit of 16 is converted to a carbonyl group, leading to 7. This reaction is performed using methods and reagents known in the art. For instance, the reaction is performed in with sodium periodate in the presence of catalytic amounts of a suitable osmium source such as osmium(VIII) oxide or potassium osmate(VI) dihydrate, in solvents such as acetone, tert-butylalcohol, water, or mixtures thereof, at temperatures between 0° C. and 30° C.

Alternatively, compounds 7 can be synthesised as outlined in scheme 4, step g. Thus, compound 17 is alkylated with halide 18. This reaction is performed in the presence of a suitable base, e. g., sodium hydride, potassium tert-butylate, sodium carbonate, or sodium hydrogencarbonate, in a solvent such as tetrahydrofuran, 1,4-dioxane, water, N,N-dimethyl-formamide, or mixtures thereof, at temperatures between 0° C. and 100° C.

Compounds of formula 4 in which E is oxygen and F is $CH_2$ are represented by general formula 4A. $PG^1$ is a suitable protective group, e. g., benzyl or benzyloxycarbonyl, G, $R^1$, $R^2$, $R^3$, $R^4$, $R^5$, V, and n are as defined before.

4A

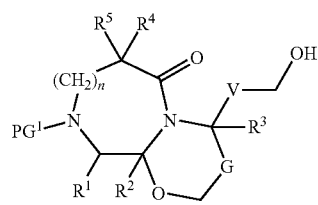

Compounds of formula 4A can be produced by thermal condensation of carbonyl compound 7 with amino alcohol 19, in analogy with scheme 3.

Amino alcohols 19 are commercially available or can be synthesised as outlined in the experimental section.

Scheme 5

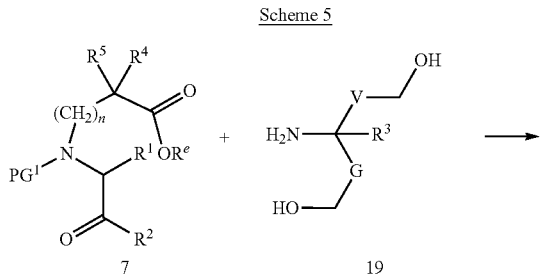

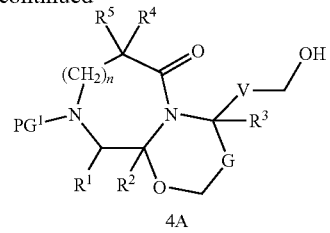

4A

In scheme 5, $PG^1$, $R^e$, G, $R^1$, $R^2$, $R^3$, $R^4$, $R^5$, V, and n are as defined before.

Compounds of formula 3 in which E is $CH_2$ and V is $(CH_2)_m$ are represented by formula 3B. Similarly, compounds of general formula 4 in which E is $CH_2$ are represented by formula 4B. $PG^1$ is a suitable protective group, e. g., benzyl or benzyloxycarbonyl, m is an integer of 1 to 3, F, G, $R^1$, $R^2$, $R^3$, $R^4$, $R^5$, V and n are as defined before.

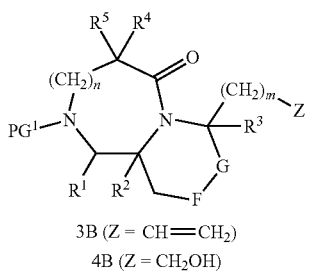

3B (Z = CH=CH$_2$)
4B (Z = CH$_2$OH)

Compounds of formula 3B and 4B can be prepared as described in scheme 6. $PG^1$, $PG^2$, and $PG^3$ are suitable protective groups—for instance, $PG^1$ is benzyloxycarbonyl, $PG^2$ is tert-butoxycarbonyl, and $PG^3$ is tetrahydropyran-2-yl. $R^e$ is methyl, ethyl, or tert-butyl, m is an integer of 1 to 3, F, G, $R^1$, $R^2$, $R^3$, $R^4$ and $R^5$ are as defined before.

In step a, scheme 6, aldehyde or ketone 20A, 20B, or 20C undergoes a reductive amination reaction with amino ester 11, leading to 21A, 21B, and 21C, respectively. This reaction is performed in analogy with scheme 4, step a.

In step b, scheme 6, secondary amine 21A, 21B, or 21C is converted to protected derivative 22A, 22B, and 22C, respectively. This reaction is performed in analogy with scheme 4, step b.

In step c, scheme 6, compound 22A is transformed into 3B. This conversion is performed in two steps. In the case where $R^e$ is methyl or ethyl, and $PG^2$ is tert-butoxycarbonyl, $PG^2$ is cleaved under acidic conditions, e. g., using hydrogen chloride in 1,4-dioxane or trifluoroacetic acid in dichloromethane at temperatures between 0° C. and 25° C. The resultant amino ester is cyclised in the presence of a base, e. g., potassium carbonate, in a solvent such as methanol, at temperatures between 0° C. and 60° C. In the case where $R^e$ is tert-butyl and $PG^2$ is tert-butoxycarbonyl, both $R^e$ and $PG^2$ are cleaved under acidic conditions as described above, i. e., using hydrogen chloride in 1,4-dioxane or trifluoroacetic acid in dichloromethane at temperatures between 0° C. and 25° C. The resultant amino acid is condensed to lactam 3B using methods and reagents known in the art, e. g, using a suitable coupling agent such as N,N'-dicyclohexylcarbodiimide or O-(7-azabenzotriazol-1-yl)-N,N,N',N'-tetramethyluronium hexafluoro-phosphate, in the presence of a base, e. g., triethylamine or 4-methylmorpholine, in a solvent such as tetrahydrofuran or N,N-dimethylformamide, at temperatures between 0° C. and 60° C.

In analogy with the transformation from 22A to 3B, 22B is transformed into 4B in scheme 6, step c.

Similarly, 22C is transformed into 4B in scheme 6, step c. Here, in the case where $PG^3$ is tetrahydropyran-2-yl, $PG^3$ is cleaved concomitantly with $PG^1$ and $PG^2$, as described above.

Scheme 6

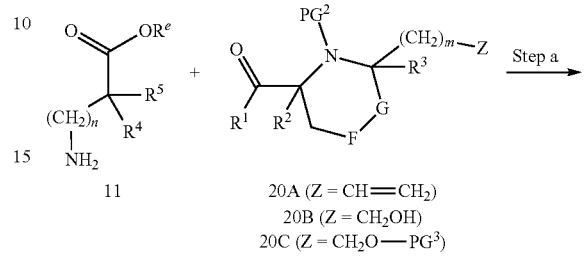

20A (Z = CH=CH$_2$)
20B (Z = CH$_2$OH)
20C (Z = CH$_2$O—PG$^3$)

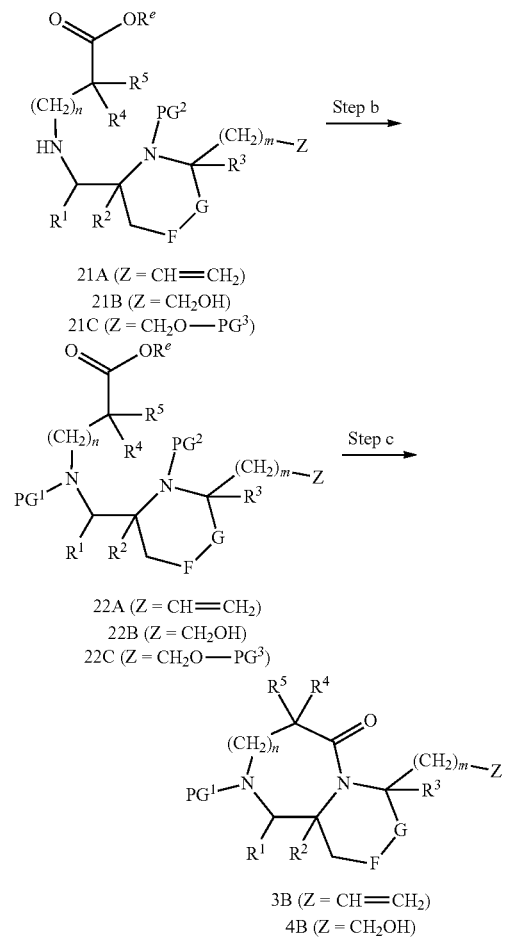

21A (Z = CH=CH$_2$)
21B (Z = CH$_2$OH)
21C (Z = CH$_2$O—PG$^3$)

22A (Z = CH=CH$_2$)
22B (Z = CH$_2$OH)
22C (Z = CH$_2$O—PG$^3$)

3B (Z = CH=CH$_2$)
4B (Z = CH$_2$OH)

In scheme 6, $PG^1$, $PG^2$, $PG^3$, $R^e$, F, G, $R^1$, $R^2$, $R^3$, $R^4$ and $R^5$ are as defined before.

Compound of formula 22B can be synthesised from 22A as outlined in scheme 7. PG' and $PG^2$ are suitable protective groups—for instance, $PG^1$ is benzyloxycarbonyl and $PG^2$ is tert-butoxycarbonyl $R^e$ is methyl, ethyl, or tert-butyl. m is an integer of 1 to 3, F, G, $R^1$, $R^2$, $R^3$, $R^4$ and $R^5$ are as defined before.

Thus, alkene 22A is converted to alcohol 22B through a hydroboration reaction, using reagents and conditions described in the art. For instance, the reaction is performed in the presence of 9-borabicyclo[3.3.1]nonane in a solvent such as tetrahydrofuran, at temperatures between 0° C. and 30° C., followed by oxidation of the 9-borabicyclo[3.3.1]non-9-yl adduct with hydrogen peroxide or sodium perborate, in solvents such as water, methanol, tetrahydrofuran, or mixtures thereof, at temperatures between 0° C. and 30° C.

Scheme 7

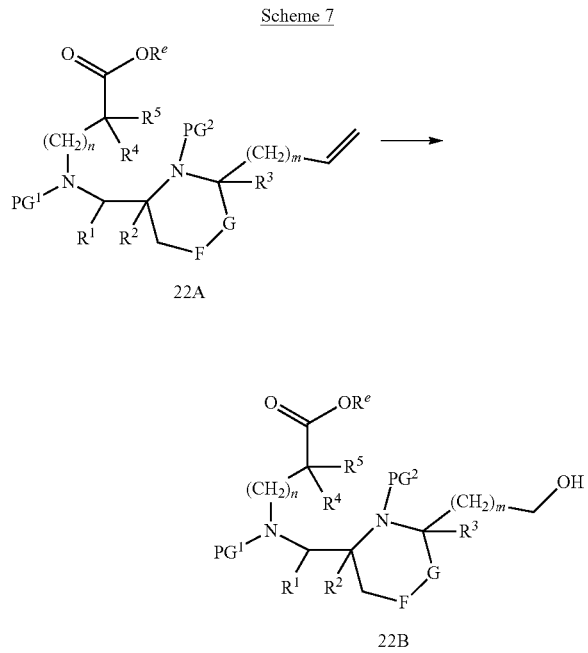

In scheme 7, $PG^1$, $PG^2$, $R^e$, F, G, $R^1$, $R^2$, $R^3$, $R^4$ and $R^5$ are as defined before.

Compounds of formula 20A, 20B, and 20C can be prepared as described in scheme 8. $PG^2$ and $PG^3$ are suitable protective groups; for instance $PG^2$ is tert-butoxycarbonyl and $PG^3$ is tetrahydropyran-2-yl, m is an integer of 1 to 3, $R^g$ is methyl, ethyl or benzyl, F, G, $R^1$, $R^2$ and $R^3$, are as defined before.

Compounds of formula 20A, 20B, and 20C in which $R^1$ is H can be synthesised as outlined in scheme 8, steps a and b.

In step a, scheme 8, ester 21A, 21B, or 21C are reduced to alcohol 22A, 22B, and 22C, respectively. This reaction is performed under suitable conditions, e. g., using lithium aluminum hydride in tetrahydrofuran or diethyl ether, or using sodium borohydride or lithium borohydride in methanol or tetrahydrofuran, at temperatures between −50° C. and +50° C.

In step b, scheme 8, alcohol 22A, 22B, or 22C is oxidised to aldehyde 20A, 20B, and 22C, respectively, using methods and reagents known in the art. For instance, the reaction is performed using dimethyl sulfoxide-based reagents such as dimethyl sulfoxide-oxalyl chloride or dimethyl sulfoxide-trifluoroacetic anhydride, in the presence of an organic base such as triethylamine in a solvent such as dichloromethane, at temperatures below 0° C., typically between −78° C. and −60° C. Alternatively, the reaction is performed in the presence of 1,1,1-tris(acetyloxy)-1,1-dihydro-1,2-benziodoxol-3 (1H)-one (Dess-Martin periodinane), in a suitable solvent such as dichloromethane or acetonitrile, at temperatures between 0° C. and 50° C.

Alternatively, compounds of formula 20A, 20B, and 20C in which $R^1$ is H can be synthesised directly from esters 21A, 21B and 21C, respectively using a suitable reducing agent, e. g., diisobutylaluminum hydride, in a solvent such as tetrahydrofuran or dichloromethane, at temperatures between −78° C. and 0° C.

Compounds of formula 20A, 20B, and 20C in which $R^1 \neq H$ can be synthesised as outlined in scheme 8, steps c and d.

In step c, scheme 8, esters 21A, 21B, or 22C are converted into N-methoxy-N-methylamides 23A, 23B, and 23C, respectively, using methods and reagents known in the art. For instance, the reaction is performed using N,O-dimethylhydroxylamine in the presence of trimethylaluminum, in a solvent such as dichloromethane, at temperatures between −20° C. and +30° C.

In step d, scheme 8, N-methoxy-N-methylamides 23A, 23B, or 23C are transformed into ketones of formula 20A, 20B, and 20C, respectively, using methods and reagents known in the art. For instance, the reaction is performed using organolithium ($R^1$—Li) or organomagnesium ($R^1$—Mg-Hal, Hal is Cl, Br, or I) reagents, in a solvent such as tetrahydrofuran, at temperatures between −78° C. and +70° C.

Scheme 8

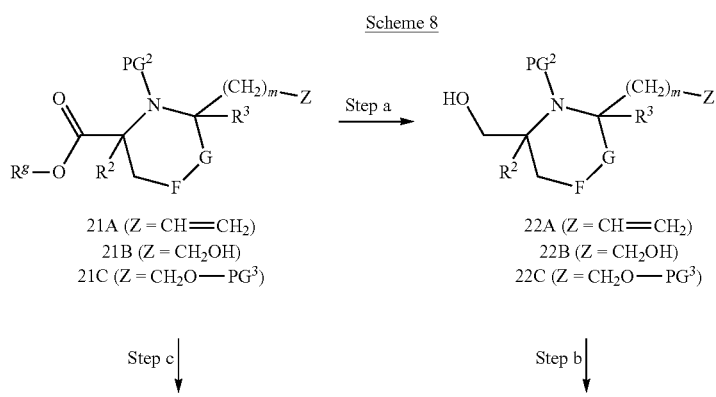

21A (Z = CH=CH$_2$)
21B (Z = CH$_2$OH)
21C (Z = CH$_2$O—PG$^3$)

22A (Z = CH=CH$_2$)
22B (Z = CH$_2$OH)
22C (Z = CH$_2$O—PG$^3$)

Step c ↓                                    Step b ↓

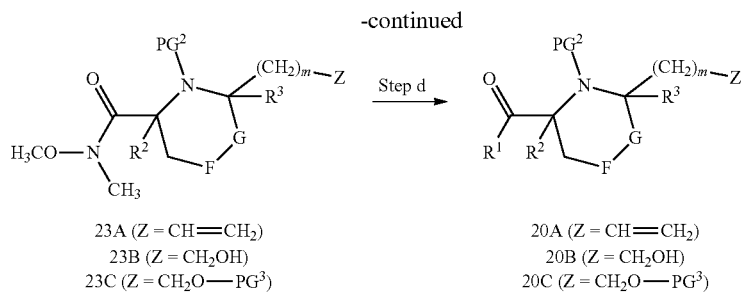

23A (Z = CH=CH₂)
23B (Z = CH₂OH)
23C (Z = CH₂O—PG³)

20A (Z = CH=CH₂)
20B (Z = CH₂OH)
20C (Z = CH₂O—PG³)

In scheme 8, $PG^2$, $PG^3$, $R^g$, F, G, $R^1$, $R^2$ and $R^3$, are as defined before.

Compounds of formula 21B and 21C can be synthesised from 21A as outlined in scheme 9. $R^g$ is methyl, ethyl, tert-butyl or benzyl, $PG^2$ is a suitable protective group, e.g., tert-butoxycarbonyl, m is an integer of 1 to 3, F, G, $R^2$ and $R^3$ are as defined before.

In step a, scheme 9, alkene 21A is converted to alcohol 21B through a hydroboration reaction, in analogy with scheme 7.

In step b, scheme 9, alcohol 21B protected, leading to 21C. For instance, in the case where $PG^3$ is tetrahydropyran-2-yl, the reaction is performed using 3,4-dihydro-2H-pyran in the presence of a suitable catalyst, e. g., toluene 4-sulfonic acid or pyridinium toluene-4-sulfonate, in a solvent such as dichloromethane, at about room temperature.

Scheme 9

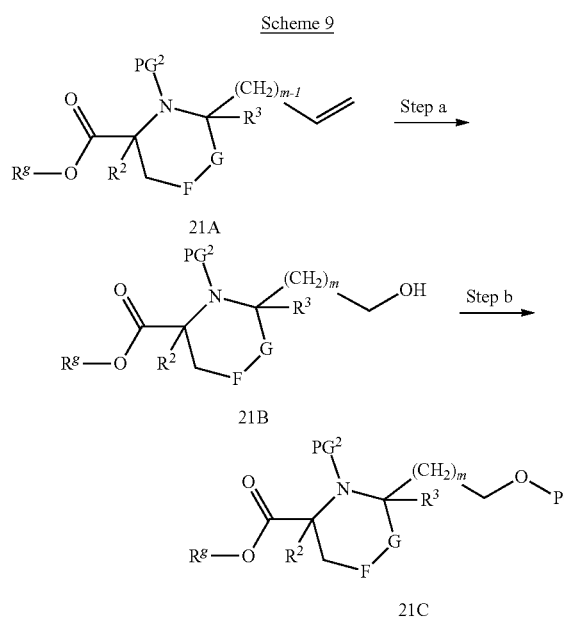

In scheme 9, $PG^2$, $PG^3$, $R^g$, F, G, $R^2$ and $R^3$ are as defined before.

Compounds of formula 21A can be synthesised as outlined in scheme 10. $PG^2$ is a suitable protective group, e.g., tert-butoxycarbonyl, $R^g$ is methyl, ethyl, tert-butyl or benzyl, m is an integer of 1 to 3, F, G, $R^2$ and $R^3$ are as defined before. Thus, ester 24 is functionalised at the acidic α-position using methods known in the art. For instance, in the case where $R^2$ is alkyl or cycloalkyl, ester 24 is deprotonated using a suitable base, e. g., lithium diisopropylamide or lithium bis(trimethylsilyl)amide, in a solvent such as tetrahydrofuran, at temperatures between –78° C. and 0° C. followed by treatment of the enolate intermediate with halide $R^2$-Hal (Hal is Cl, Br or I), leading to 21A.

Scheme 10

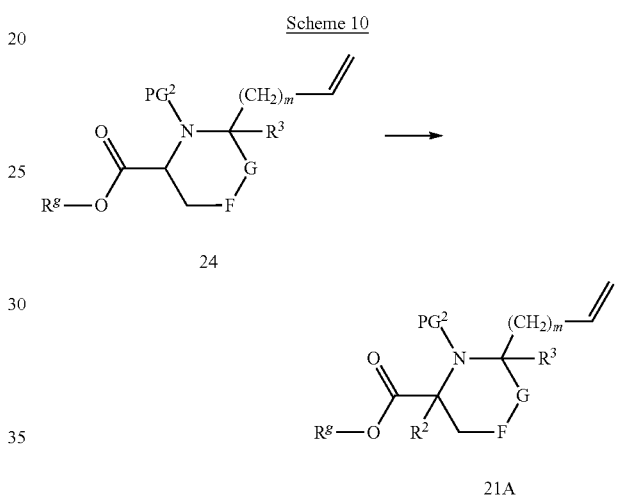

In scheme 10, $PG^2$, $R^g$, F, G, $R^2$ and $R^3$ are as defined before.

Compounds of formula 24 can be synthesised as outline in scheme 11. $PG^2$ is a suitable protective group, e. g., tert-butoxycarbonyl, $R^g$ is methyl, ethyl, tert-butyl or benzyl, m is an integer of 1 to 3, F, G and $R^3$ are as defined before.

In step a, scheme 11, compound 25 is protected at the amide N—H, leading to 26. In the case where $PG^2$ is tert-butoxycarbonyl, the reaction is performed using di-tert-butyl dicarbonate, in the presence of triethylamine, 4-(dimethylaminopyridine) or mixtures thereof, in solvents such as dichloromethane or acetonitrile, at temperatures between 0° C. and 30° C.

In step b, scheme 11, compound 26 is reacted with a Grignard reagent of the general formula H₂C=CH—(CH₂)ₘ—Mg-Hal (Hal is Cl, Br or I), leading to 27. This reaction is performed in a suitable solvent, e. g., tetrahydrofuran, at temperatures between –78° C. and 0° C. The Grignard reagent can be also branched as expressed with the more general formula H₂C=CH—V—Mg-Hal, in which V is as defined before.

In step c, scheme 11, compound 27 is deprotected and cyclised to 28. This reaction is performed in the presence of a suitable acid, e. g., trifluoroacetic acid, in a solvent such as dichloromethane, at temperatures between –20° C. and +30° C.

In step d, imine 28 is reacted with a Grignard reagent of the general formula $R^3$—Mg-Hal (Hal is Cl, Br or I), leading to 29. This reaction is performed in a suitable solvent, e. g., tetrahydrofuran, at temperatures between −78° C. and 0° C., optionally in the presence of a Lewis acid such as boron trifluoride etherate.

In step e, scheme 11, secondary amine 29 is protected, leading to 24. In the case where $PG^2$ is tert-butoxycarbonyl, the reaction is performed using reagents and conditions described in the art, e. g., using di tert-butyl dicarbonate in a solvent such as dichloromethane.

Compounds of general formula 25 are commercially available or can be synthesised as described in the experimental section.

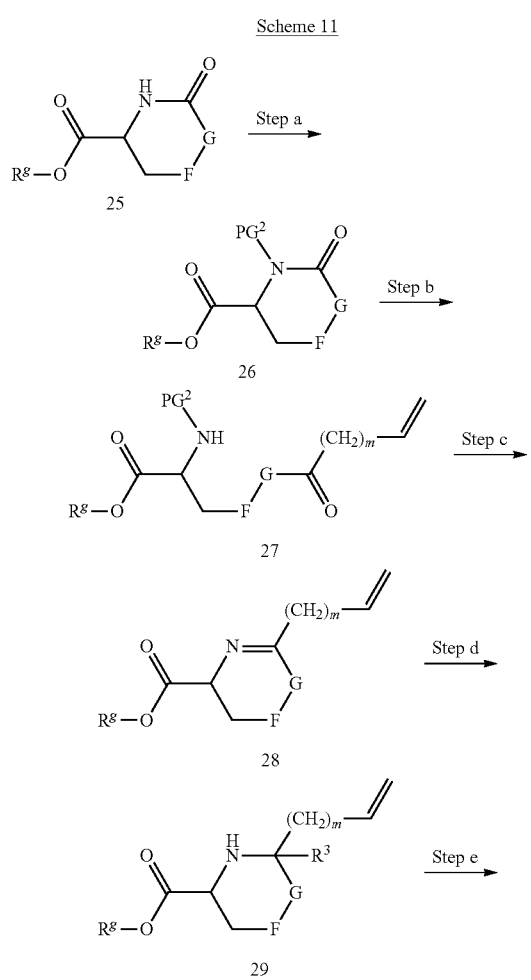

In scheme 11, $PG^2$, $R^g$, F, G, $R^2$ and $R^3$ are as defined before.

Compounds of formula 24 in which $R^3$ is hydrogen are represented by formula 24A. $PG^2$ is a suitable protective group, e. g., tert-butoxycarbonyl, m is an integer of 1 to 3, $R^g$ is methyl, ethyl, tert-butyl or benzyl.

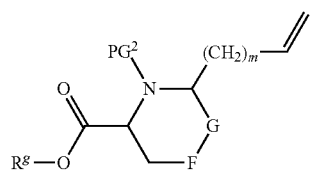

Compounds of formula 24A can be synthesised from compound 27 (scheme 11) by reaction with a silane reagent, e. g., triphenylsilane or triethylsilane, in the presence of a suitable Lewis acid, preferably tris(pentafluorophenyl)borane, in a solvent such as tetrahydrofuran, at temperatures between −78° C. and +30° C.

Compound of formula 24A can also be synthesised as outlined in scheme 12. $PG^2$ is a suitable protective group, e. g., tert-butoxycarbonyl, $R^g$ is methyl, ethyl, tert-butyl or benzyl, F and G are as defined before.

In step a, scheme 12, compound lactone 25 is reduced to lactol 30, using reagents and conditions known in the art. For instance, the reaction is performed in the presence of a suitable reducing agent, e. g., lithium triethylborohydride, in a solvent such as tetrahydrofuran, at temperatures between −78° C. and 0° C.

In step b, scheme 12, lactol 30 is converted to compound 31, using reagents and methods known in the art. For instance, the reaction is performed in the presence of a suitable acid, e. g., toluene 4-sulfonic acid, in methanol, at temperatures between 0° C. and the boiling point of the solvent.

In step c, scheme 12, compound 31 is transformed into 24A, using reagents and methods known in the art. For instance, the reaction is performed using a Grignard reagent of the general formula $H_2C=CH—(CH_2)_m—Mg-Hal$ (Hal is Cl, Br or I). This reaction is performed in a suitable solvent, e. g., tetrahydrofuran or diethyl ether, at temperatures between −78° C. and 0° C., in the presence of copper(I) bromide dimethylsulfide complex and boron trifluoride etherate. The Grignard reagent can be also branched as expressed with the more general formula $H_2C=CH—V—Mg-Hal$, in which V is as defined before.

Alternatively, in the case where m is 1, the reaction is preferably performed with allyltrimethylsilane, in the presence of a Lewis acid such as boron trifluoride etherate, at temperatures between −78° C. and 0° C.

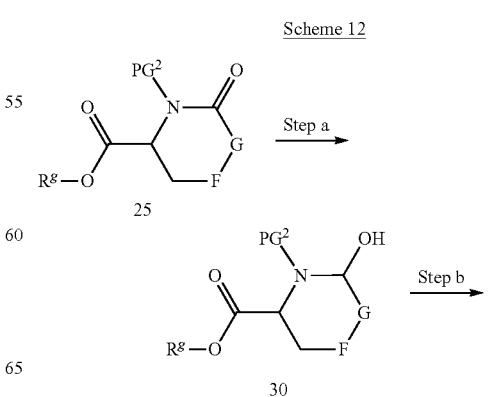

Scheme 12

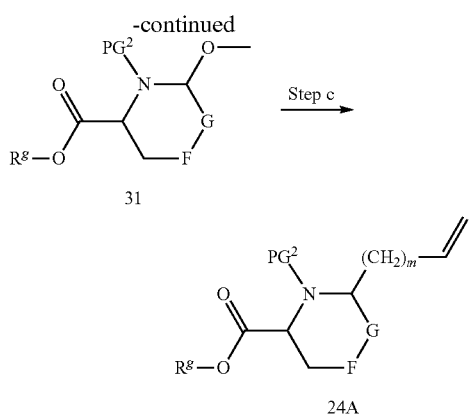

In scheme 12, $PG^2$, $R^g$, F and G are as defined before.

Compounds of general formula 30 can also be synthesised from alkene 32 as outlined in scheme 13. $PG^2$ is a suitable protective group, e. g., tert-butoxycarbonyl, $R^g$ is methyl, ethyl, tert-butyl or benzyl. For instance, the reaction is performed in analogy with scheme 4, step f. Alternatively, this conversion is accomplished through ozonolysis, in solvents such as dichloromethane, methanol or mixtures thereof, at temperatures between −78° C. and 0° C., followed by workup with dimethylsulfide.

Scheme 13

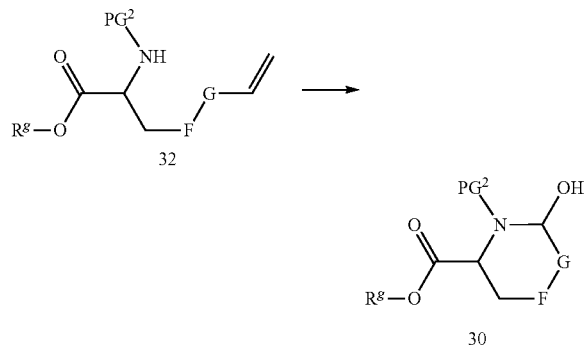

In scheme 13, $PG^2$, $R^g$, F and G are as defined before.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbent or eluent). The invention embraces all of these forms.

As described above, the compounds of formula (I) are CCR2 receptor antagonists, with some antagonist activity also at CCR3 and CCR5. These compounds consequently prevent migration of various leukocyte populations through the blockade of CCR2 stimulation. They therefore can be used for the treatment and/or prevention of inflammatory and/or allergic diseases, such as peripheral arterial occlusive disease, critical limb ischemia (CLI), vulnerable atherosclerotic plaque patients, unstable angina, congestive heart failure, left ventricular hypertrophy, ischemia reperfusion injury, stroke, cardiomyopathy, restenosis, rheumatoid arthritis, diabetes and diabetic complications, diabetic nephropathy, irritable bowel syndrome, Crohn's disease, multiple sclerosis, neuropathic pain, atherothrombosis and/or burns/ulcers in diabetes/CLI, and asthma.

Prevention and/or treatment of inflammatory diseases, particularly peripheral arterial occlusive diseases or atherothrombosis is the preferred indication.

The invention therefore also relates to pharmaceutical compositions comprising a compound as defined above and a pharmaceutically acceptable excipient.

The invention likewise embraces compounds as described above for use as therapeutically active substances, especially as therapeutically active substances for the treatment and/or prophylaxis of inflammatory and/or allergic diseases, particularly as therapeutically active substances for the treatment and/or prophylaxis of peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable bowel syndrome, Crohn's disease, multiple sclerosis, neuropathic pain, atherothrombosis, burns/ulcers in diabetes/CLI, and allergy, asthma.

The invention also relates to the use of compounds as described above for the preparation of medicaments for the therapeutic and/or prophylactic treatment of inflammatory and/or allergic diseases, particularly for the therapeutic and/or prophylactic treatment of peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable bowel syndrome, Crohn's disease, multiple sclerosis, neuropathic pain, atherothrombosis, burns/ulcers in diabetes/CLI, and asthma. Such medicaments comprise a compound as described above.

The invention also relates to the process and the intermediates for manufacturing the compounds of formula (I) as well as the process for manufacturing the intermediates.

CCR2 receptor antagonistic activity by the compounds of the present invention can be demonstrated by treceptor binding assays and calcium mobilization assays, examples of which are described in the Examples.

The compounds of formula (I) and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula (I).

EXAMPLES

The starting materials and reagents, which do not have their synthetic route explicitly disclosed herein, are generally available from commercial sources or are readily prepared using methods well known to the person skilled in the art.

The following examples are provided for the purpose of further illustration and are not intended to limit the scope of the claimed invention.

Abbreviations:
aq.=aqueous, Boc=tert-butoxycarbonyl, DCM=dichloromethane, DMF=N,N-dimethylformamide, Et$_3$N=Triethylamine, EtOAc=ethyl acetate, EtOH=Ethanol, HOAc=acetic acid, HPLC=high-pressure liquid chromatography, ISP=ion spray, MeOH=methanol, MS=mass spectrometry, sat.=saturated, THF=tetrahydrofuran.

Intermediate 1

(S)-2-[Benzyloxycarbonyl-(2-oxo-ethyl)-amino]-propionic acid methyl ester

A) (S)-2-(2,2-Dimethoxy-ethylamino)-propionic acid methyl ester

To a solution of L-alanine methyl ester hydrochloride (5.00 g, 35.8 mmol) in MeOH (100 mL) were added at 0° C. dimethoxyacetaldehyde (45% solution in tert-butyl methyl ether, 12.0 mL, 47 mmol) magnesium sulfate (38.8 g, 322 mmol), and sodium cyanoborohydride (3.08 g, 46.6 mmol). The ice bath was removed, then after 16 h the excess reagent was destroyed by careful addition of sat. aq. sodium hydrogencarbonate solution at 0° C. The reaction mixture was partitioned between sat. aq. sodium hydrogencarbonate solution and EtOAc. The organic layer was washed with brine, dried over magnesium sulfate, filtered, and evaporated to afford the title compound (5.50 g, 80%). Light yellow liquid, MS (ISP)=192.2 (M+H)$^+$.

B) (S)-2-[Benzyloxycarbonyl-(2,2-dimethoxy-ethyl)-amino]-propionic acid methyl ester Benzyl chloroformate (4.46 g, 24.8 mmol) was added at 0° C. to a mixture of (S)-2-(2,2-dimethoxy-ethylamino)-propionic acid methyl ester (4.75 g, 24.8 mmol) and sodium hydrogencarbonate (4.17 g, 49.7 mmol) in acetone (25 mL) and water (25 mL). The ice bath was removed, then after 2 h the reaction mixture was poured onto ice water and extracted with EtOAc. The organic layer was dried over magnesium sulfate, filtered, and evaporated. Chromatography (SiO$_2$; heptane-EtOAc gradient) afforded the title compound (5.84 g, 72%). Yellow oil, MS (ISP)=348.2 (M+Na)$^+$.

C) (S)-2-[Benzyloxycarbonyl-(2-oxo-ethyl)-amino]-propionic acid methyl ester

A solution of (S)-2-[benzyloxycarbonyl-(2,2-dimethoxy-ethyl)-amino]-propionic acid methyl ester (2.94 g, 9.04 mmol) and pyridinium toluene-4-sulfonate (1.13 g, 4.52 mmol) in 2-butanone (30 mL) and water (8.6 mL, 54 mmol) was heated under reflux for 16 h, then the solution was partitioned between EtOAc and water. The organic layer was washed with brine, dried over magnesium sulfate, filtered, and evaporated to afford the title compound (2.45 g, 97%). Yellow oil, MS (ISP)=348.3 (M+Na)$^+$.

Intermediate 2

(S)-2-[Benzyloxycarbonyl-(2-oxo-propyl)-amino]-propionic acid methyl ester

To a solution of L-alanine methyl ester hydrochloride (6.00 g, 43.0 mmol) in MeOH (120 mL) were added at 0° C. methacrolein (4.12 g, 56 mmol), magnesium sulfate (46.6 g, 387 mmol), and sodium cyanoborohydride (3.70 g, 56 mmol). The ice bath was removed, then after 16 h the excess reagent was destroyed by careful addition of sat. aq. sodium hydrogencarbonate solution at 0° C. The reaction mixture was partitioned between sat. aq. sodium hydrogencarbonate solution and EtOAc. The organic layer was washed with brine, dried (MgSO$_4$), filtered, and evaporated to afford a 1:1 mixture of (S)-2-(2-methyl-allylamino)-propionic acid methyl ester and (S)-2-isobutylamino-propionic acid methyl ester title compound (5.4 g). This was reacted with benzyl chloroformate in analogy with intermediate 1B, leading to a mixture of (S)-2-[benzyloxycarbonyl-(2-methyl-allyl)-amino]-propionic acid methyl ester and (S)-2-(benzyloxycarbonyl-isobutyl-amino)-propionic acid methyl ester (9.8 g). This was suspended in acetone (60 mL) and water (60 mL), then sodium periodate (13.8 g, 64 mmol) and osmium tetroxide solution (2.5% in tert-butylalcohol, 2.2 mL, 0.43 mmol) were added at 0° C. The ice bath was removed, then after 16 h the reaction mixture was partitioned between EtOAc and water. The organic layer was dried over magnesium sulfate, filtered, and evaporated. Chromatography (SiO$_2$; heptane-EtOAc gradient) produced the title compound (1.88 g, 14%). Colourless oil, MS: 294.1 (M+H)$^+$.

Intermediate 3

(S)-2-[Benzyl-(2-oxo-propyl)-amino]-propionic acid methyl ester

A mixture of N-benzylalanine methyl ester hydrochloride (1.00 g, 4.35 mmol), chloroacetone (1.21 g, 13.1 mmol), and sodium hydrogencarbonate (951 mg, 11.3 mmol) in 1,4-dioxane (11 mL) and water (1 mL) was heated at 70° C. for 2 days, then partitioned between EtOAc and 2 M aq. sodium carbonate solution. The organic layer was dried over magnesium sulfate, filtered, and evaporated. Chromatography (SiO$_2$; heptane-EtOAc gradient) produced the title compound (540 mg, 50%). Colourless oil, MS: 250.1 (M+H)$^+$.

Intermediate 4

A) tert-Butyl 4,4-difluoro-6-azaspiro[2.5]octane-6-carboxylate

Silica gel (particle size 32-63 μm, 60 mg) was added to a solution of tert-butyl 4-oxo-6-azaspiro[2.5]octane-6-carboxylate (PCT Int. Appl. WO 2009010429; 1000 mg, 4.44 mmol) in 1,2-dichloroethane (1 ml). Then a solution of bis(2-methoxyethyl)aminosulfur trifluoride (3.1 g, 13.3 mmol) in toluene (3.6 ml) was slowly added. The resulting mixture was heated to 70° C. and was then stirred at this temperature for 6 h. Sodium bicarbonate (74.6 mg, 888 μmol), potassium fluoride (258 mg, 4.44 mmol) and methyltrioctylammonium chloride (179 mg, 444 μmol) were added at 70° C. and the mixture was stirred at 70° C. for an additional 15 h. The mixture was cooled to room temperature and was then quenched in 20% aq. ammonium hydroxide solution (10 ml) while the pH was maintained around 8.5. The organic phase was separated, washed with water, and evaporated. Chromatography (SiO$_2$; heptane→heptane/ethyl acetate 4:1) afforded the title compound (852 mg, 78%). White solid, MS: 248.2 (M+H)$^+$.

B) 4,4-Difluoro-6-azaspiro[2.5]octane hydrochloride

Hydrogen chloride (4 M in dioxane, 3.29 ml, 13.2 mmol) was added to a solution of tert-butyl 4,4-difluoro-6-azaspiro[2.5]octane-6-carboxylate (592 mg, 2.39 mmol) in ethanol (0.5 ml). The solvents were evaporated to give a white solid. The solid residue was washed with tert-butylmethylether to afford the title compound (404 mg, 92%). White solid, MS: 148.2 (M+H)$^+$.

Examples 1 and 2

(3S,6S,8aS)-3-[2-((S)-4-Hydroxy-6-aza-spiro[2.5]oct-6-yl)-ethyl]-6-methyl-5-oxo-hexahydro-oxazolo[3,2-a]pyrazine-7-carboxylic acid (3,4-dichloro-phenyl)-amide and (3S,6S,8aR)-3-[2-((S)-4-hydroxy-6-aza-spiro[2.5]oct-6-yl)-ethyl]-6-methyl-5-oxo-hexahydro-oxazolo[3,2-a]pyrazine-7-carboxylic acid (3,4-dichloro-phenyl)-amide

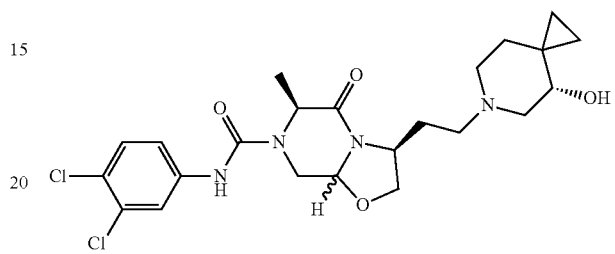

Example 1: (S)-epimer
Example 2: (R)-epimer

A) (S)-4-(2-Hydroxy-ethyl)-2,2-dimethyl-oxazolidine-3-carboxylic acid benzyl ester A solution of (S)—N-(benzyloxycarbonyl)-2-aminobutane-1,4-diol (8.00 g, 33.4 mmol) and toluene-4-sulfonic acid monohydrate (318 mg, 1.67 mmol) in 2,2-dimethoxypropane (320 mL) was stirred at room temperature, then after 2 h 2-methoxypropene (7.71 g, 107 mmol) was added, then after 72 h the reaction mixture was partitioned between EtOAc and sat. aq. sodium hydrogencarbonate solution. The organic layer was dried over magnesium sulfate, filtered, and evaporated. The residue was taken up in DCM (200 mL), then after addition of SiO$_2$ (80 g) and water (4.8 mL) the slurry was stirred for 64 h at room temperature. After dilution with DCM and addition of anhydrous magnesium sulfate, insoluble material was removed by filtration through diatomaceous earth. The filtrate was evaporated and chromatographed (SiO$_2$; heptane/EtOAc 1:1) to afford the title compound (8.92 g, 96%). Light yellow oil, MS (ISP)=280.1 (M+H)$^+$.

B) (S)-2,2-Dimethyl-4-(2-oxo-ethyl)-oxazolidine-3-carboxylic acid benzyl ester A solution of dimethyl sulfoxide (6.39 g, 81.8 mmol) in DCM (25 mL) was added at −70° C. to a solution of oxalyl chloride (5.59 g, 44.1 mmol) in DCM (90 mL), then after 15 min a solution of (S)-4-(2-hydroxy-ethyl)-2,2-dimethyl-oxazolidine-3-carboxylic acid benzyl ester (8.79 g, 31.5 mmol) in DCM (45 mL) was added dropwise. After 60 min Et$_3$N (15.9 g, 157 mmol) was added, then after 20 min the cooling bath was removed and the reaction mixture was stirred for 2 h. The reaction mixture was poured onto water and extracted five times with DCM. The combined organic phases were dried (MgSO$_4$), filtered, and evaporated. Chromatography (SiO$_2$; heptane/EtOAc 1:1) produced the title compound (8.52 g, 98%) as light yellow liquid.

C) (S)-4-[2-(S)-4-hydroxy-6-aza-spiro[2.5]oct-6-yl)-ethyl]-2,2-dimethyl-oxazolidine-3-carboxylic acid benzyl ester To a solution of (S)-2,2-dimethyl-4-(2-oxo-ethyl)-oxazolidine-3-carboxylic acid benzyl ester (8.51 g, 30.7 mmol) in DCM (140 mL) were added (S)-6-aza-spiro[2.5]octan-4-ol hydrochloride (PCT Int. Appl. WO 2009010429; 5.03 g, 30.7 mmol), Et$_3$N (3.11 g, 30.7 mmol) and sodium triacetoxyborohydride (9.11 g, 43.0 mmol) at room temperature. After 1 h the reaction mixture was partitioned between sat. aq. sodium hydrogencarbonate solution and DCM. The aqueous layer was extracted twice with DCM, the combined organic phases were dried (MgSO$_4$), filtered, and evaporated to afford the title compound (11.6 g, 97%). Light yellow gum, MS (ISP)= 389.3 (M+H)$^+$.

D) [(S)-3-((S)-4-Hydroxy-6-aza-spiro[2.5]oct-6-yl)-1-hydroxymethyl-propyl]-carbamic acid benzyl ester A solution of (S)-4-[2-((S)-4-hydroxy-6-aza-spiro[2.5]oct-6-yl)-ethyl]-2,2-dimethyl-oxazolidine-3-carboxylic acid benzyl ester (5.00 g, 12.9 mmol) in MeOH/water 9:1 (50 mL) was stirred at room temperature in the presence of Amberlite® IR-120 resin (15.8 g). After 16 h the resin was collected by filtration and washed with MeOH. The filtrate was discarded, and the product was recovered by digesting the Amberlite® resin three times in 7 M methanolic ammonia solution (60 mL) at room temperature over 15 min. The ammonia solutions were combined and evaporated to afford the title compound (4.27 g, 95%). Colourless oil, MS (ISP)= 349.3 (M+H)$^+$.

E) (S)-6-((S)-3-Amino-4-hydroxy-butyl)-6-aza-spiro[2.5]octan-4-ol

A solution of [(S)-3-((S)-4-hydroxy-6-aza-spiro[2.5]oct-6-yl)-1-hydroxymethyl-propyl]-carbamic acid benzyl ester (350 mg, 1.00 mmol) in MeOH (5 mL) was stirred for 1½ h at room temperature under a hydrogen atmosphere (1 bar) in the presence of palladium (10% on activated charcoal, 35 mg), then insoluble material was removed by filtration through diatomaceous earth. The filtrate was evaporated to afford the title compound (215 mg, 100%) Colourless gum, MS (ISP)=215.3 (M+H)$^+$.

F) (3S,6S)-3-[2-((S)-4-Hydroxy-6-aza-spiro[2.5]oct-6-yl)-ethyl]-6-methyl-5-oxo-hexahydro-oxazolo[3,2-a]pyrazine-7-carboxylic acid benzyl ester A solution of (S)-2-[benzyloxycarbonyl-(2-oxo-ethyl)-amino]-propionic acid methyl ester (intermediate 1; 570 mg, 2.04 mmol) and (S)-6-((S)-3-amino-4-hydroxy-butyl)-6-aza-spiro[2.5]octan-4-ol (445 mg, 2.04 mmol) in toluene (6 mL) was heated at reflux for 16 h, then the reaction mixture was concentrated. Chromatography (SiO$_2$; DCM→DCM/MeOH/25% aq. ammonia solution 90:10:0.25) produced the title compound (763 mg, 84%) as a 70:30 mixture of (R)- and (S)-epimers. White foam, MS (ISP)=446.2 (M+H)$^+$.

G) (3S,6S,8aS)-3-[2-((S)-4-Hydroxy-6-aza-spiro[2.5]oct-6-yl)-ethyl]-6-methyl-5-oxo-hexahydro-oxazolo[3,2-a]pyrazine-7-carboxylic acid (3,4-dichloro-phenyl)-amide and (3S,6S,8aR)-3-[2-((S)-4-Hydroxy-6-aza-spiro[2.5]oct-6-yl)-ethyl]-6-methyl-5-oxo-hexahydro-oxazolo[3,2-a]pyrazine-7-carboxylic acid (3,4-dichloro-phenyl)-amide A solution of (3S,6S)-3-[2-((S)-4-hydroxy-6-aza-spiro[2.5]oct-6-yl)-ethyl]-6-methyl-5-oxo-hexahydro-oxazolo[3,2-a]pyrazine-7-carboxylic acid benzyl ester (200 mg, 0.45 mmol) in EtOH (2 mL) was stirred for 3½ h at room temperature under a hydrogen atmosphere (1 bar) in the presence of palladium (10% on activated charcoal, 96 mg), then insoluble material was removed by filtration through diatomaceous earth. The filtrate was concentrated to afford (3S,6S)-3-[2-((S)-4-hydroxy-6-aza-spiro[2.5]oct-6-yl)-ethyl]-6-methyl-hexahydro-oxazolo[3,2-a]pyrazin-5-one (130 mg). This was redissolved in DCM (2 mL), then 3,4-dichlorophenyl isocyanate (88 mg, 0.45 mmol) was added at 0° C. The ice bath was removed, then after 30 min diethylamine (16 mg, 0.23 mmol) was added and the reaction mixture was evaporated. Chromatography (SiO$_2$; DCM→DCM/MeOH/25% aq. ammonia solution 90:10:0.25) produced (3S,6S,8aS)-3-[2-((S)-4-hydroxy-6-aza-spiro[2.5]oct-6-yl)-ethyl]-6-methyl-5-oxo-hexahydro-oxazolo[3,2-a]pyrazine-7-carboxylic acid (3,4-dichloro-phenyl)-amide [example 1; 17 mg, 8%; white solid, MS 497.3 (M+H)$^+$] and (3S,6S,8aR)-3-[2-((S)-4-hydroxy-6-aza-spiro[2.5]oct-6-yl)-ethyl]-6-methyl-5-oxo-hexahydro-oxazolo[3,2-a]pyrazine-7-carboxylic acid (3,4-dichloro-phenyl)-amide (example 2; 127 mg, 57%; white foam, MS 497.3 (M+H)$^+$].

Example 3

(3S,6S)-3-[2-((S)-4-Hydroxy-6-aza-spiro[2.5]oct-6-yl)-ethyl]-6-methyl-5-oxo-hexahydro-oxazolo[3,2-a]pyrazine-7-carboxylic acid (3-chloro-phenyl)-amide

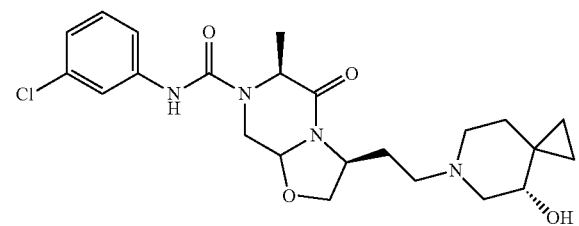 [SMILES: C[C@H]1C(=O)N2C(CN1C(=O)Nc1cccc(Cl)c1)OC[C@@H]2CCN1CCC2(CC2)[C@H](O)C1]

The title compound was produced in analogy with examples 1/2G from (3S,6S)-3-[2-((S)-4-hydroxy-6-aza-spiro[2.5]oct-6-yl)-ethyl]-6-methyl-5-oxo-hexahydro-oxazolo[3,2-a]pyrazine-7-carboxylic acid benzyl ester (examples 1/2F) and 3-chlorophenyl isocyanate. White foam, MS: 463.2 (M+H)$^+$.

Example 4

(3S,6S)-3-[2-((S)-4-Hydroxy-6-aza-spiro[2.5]oct-6-yl)-ethyl]-6-methyl-5-oxo-hexahydro-oxazolo[3,2-a]pyrazine-7-carboxylic acid (3-chloro-4-fluoro-phenyl)-amide

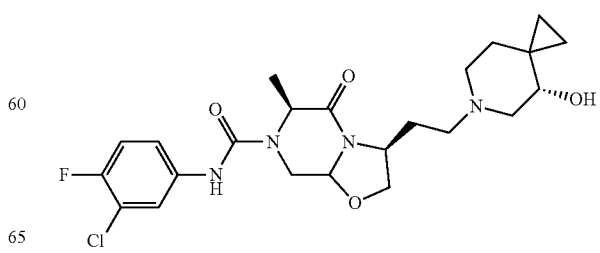

The title compound was produced in analogy with examples 1/2G from (3S,6S)-3-[2-((S)-4-hydroxy-6-aza-spiro[2.5]oct-6-yl)-ethyl]-6-methyl-5-oxo-hexahydro-oxazolo[3,2-a]pyrazine-7-carboxylic acid benzyl ester (examples 1/2F) and 3-chloro-4-fluorophenyl isocyanate. White foam, MS: 481.3 (M+H)⁺.

Example 5

(3S,6S)-3-[2-((S)-4-Hydroxy-6-aza-spiro[2.5]oct-6-yl)-ethyl]-6-methyl-5-oxo-hexahydro-oxazolo[3,2-a]pyrazine-7-carboxylic acid (3-trifluoromethyl-phenyl)-amide

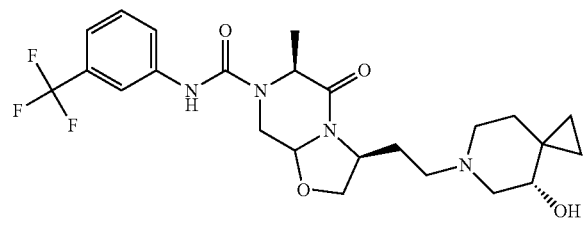

The title compound was produced in analogy with examples 1/2G from (3S,6S)-3-[2-((S)-4-hydroxy-6-aza-spiro[2.5]oct-6-yl)-ethyl]-6-methyl-5-oxo-hexahydro-oxazolo[3,2-a]pyrazine-7-carboxylic acid benzyl ester (examples 1/2F) and 3-(trifluoromethyl)phenyl isocyanate. White foam, MS: 497.3 (M+H)⁺.

Examples 6 and 7

(3S,6S,8aS)-3-[2-((S)-4-Hydroxy-6-aza-spiro[2.5]oct-6-yl)-ethyl]-6-methyl-5-oxo-hexahydro-oxazolo[3,2-a]pyrazine-7-carboxylic acid (3-chloro-4-fluoro-phenyl)-amide and (3S,6S,8aR)-3-[2-((S)-4-hydroxy-6-aza-spiro[2.5]oct-6-yl)-ethyl]-6-methyl-5-oxo-hexahydro-oxazolo[3,2-a]pyrazine-7-carboxylic acid (3-chloro-4-fluoro-phenyl)-amide

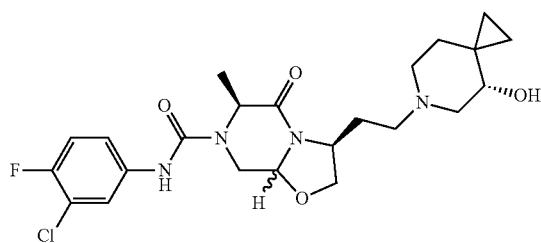 [SMILES: C[C@H]1C(=O)N2C(CN1C(=O)Nc1ccc(F)c(Cl)c1)OC[C@@H]2CCN1CCC2(CC2)[C@H](O)C1]

Example 6: (S)-epimer
Example 7: (R)-epimer

The mixture of epimers, (3S,6S)-3-[2-((S)-4-hydroxy-6-aza-spiro[2.5]oct-6-yl)-ethyl]-6-methyl-5-oxo-hexahydro-oxazolo[3,2-a]pyrazine-7-carboxylic acid (3-chloro-4-fluoro-phenyl)-amide (example 4; 176 mg, 0.37 mmol) was separated by HPLC using a Chiralpak® AD column as the stationary phase and heptane/EtOH 70:30 as the eluent. This afforded (3S,6S,8aS)-3-[2-((S)-4-hydroxy-6-aza-spiro[2.5]oct-6-yl)-ethyl]-6-methyl-5-oxo-hexahydro-oxazolo[3,2-a]pyrazine-7-carboxylic acid (3-chloro-4-fluoro-phenyl)-amide [example 6; 31 mg, 18%; white solid, MS 481.3 (M+H)⁺] and (3S,6S,8aR)-3-[2-((S)-4-hydroxy-6-aza-spiro[2.5]oct-6-yl)-ethyl]-6-methyl-5-oxo-hexahydro-oxazolo[3,2-a]pyrazine-7-carboxylic acid (3-chloro-4-fluoro-phenyl)-amide [example 7; 107 mg, 61%; white solid, MS 481.3 (M+H)⁺].

Examples 8 and 9

(3S,6S,8aS)-3-[2-((S)-4-Hydroxy-6-aza-spiro[2.5]oct-6-yl)-ethyl]-6-methyl-5-oxo-hexahydro-oxazolo[3,2-a]pyrazine-7-carboxylic acid (3-trifluoromethyl-phenyl)-amide and (3S,6S,8aR)-3-[2-((S)-4-hydroxy-6-aza-spiro[2.5]oct-6-yl)-ethyl]-6-methyl-5-oxo-hexahydro-oxazolo[3,2-a]pyrazine-7-carboxylic acid (3-trifluoromethyl-phenyl)-amide

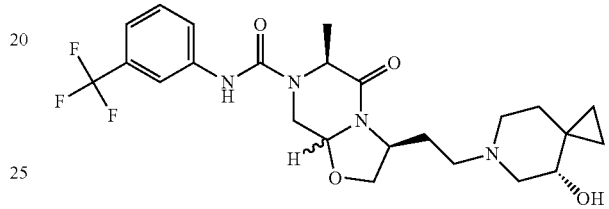

Example 8: (S)-epimer
Example 9: (R)-epimer

The title compounds were produced in analogy to examples 6/7 by HPLC separation of the mixture of epimers, (3S,6S)-3-[2-((S)-4-hydroxy-6-aza-spiro[2.5]oct-6-yl)-ethyl]-6-methyl-5-oxo-hexahydro-oxazolo[3,2-a]pyrazine-7-carboxylic acid (3-trifluoromethyl-phenyl)-amide (example 5). This produced the (S)-epimer [example 8; white solid, MS 497.3 (M+H)⁺] and the (R)-epimer [example 9; white solid, MS 497.3 (M+H)⁺].

Examples 10 and 11

(3S,6S,8aS)-3-[2-((S)-4-Hydroxy-6-aza-spiro[2.5]oct-6-yl)-ethyl]-6-methyl-5-oxo-hexahydro-oxazolo[3,2-a]pyrazine-7-carboxylic acid (3-chloro-phenyl)-amide and (3S,6S,8aR)-3-[2-((S)-4-hydroxy-6-aza-spiro[2.5]oct-6-yl)-ethyl]-6-methyl-5-oxo-hexahydro-oxazolo[3,2-a]pyrazine-7-carboxylic acid (3-chloro-phenyl)-amide

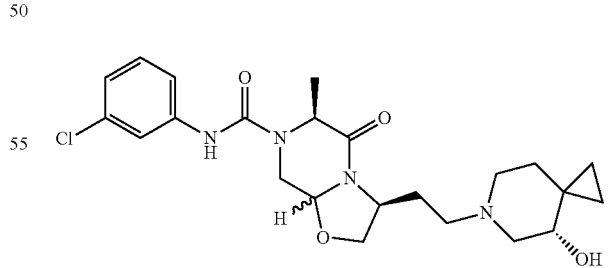

Example 10: (S)-epimer
Example 11: (R)-epimer

The title compounds were produced in analogy to examples 6/7 by HPLC separation of the mixture of epimers, (3S,6S)-3-[2-((S)-4-hydroxy-6-aza-spiro[2.5]oct-6-yl)- ethyl]-6-methyl-5-oxo-hexahydro-oxazolo[3,2-a]pyrazine-7-carboxylic acid (3-chloro-phenyl)-amide (example 3). This produced the (S)-epimer [example 10; white solid, MS 463.2 (M+H)⁺] and the (R)-epimer [example 11; white solid, MS 463.2 (M+H)⁺].

Example 12

(3S,6S)-3-[3-((S)-4-Hydroxy-6-aza-spiro[2.5]oct-6-yl)-propyl]-6,8a-dimethyl-5-oxo-hexahydro-oxazolo[3,2-a]pyrazine-7-carboxylic acid (3,4-dichloro-phenyl)-amide

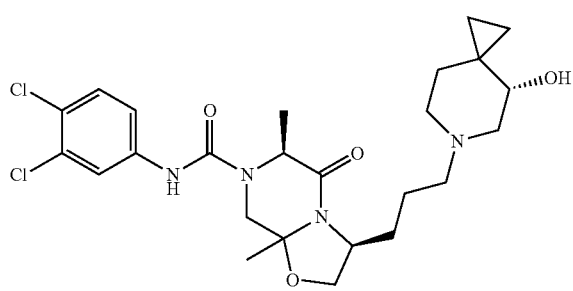 [SMILES: C[C@H]1C(=O)N2[C@@H](CCCN3CCC4(CC4)[C@H](O)C3)COC2(C)CN1C(=O)Nc1ccc(Cl)c(Cl)c1]

A) (S)-4-(3-Hydroxy-propyl)-2,2-dimethyl-oxazolidine-3-carboxylic acid benzyl ester The title compound was produced in analogy with examples 1/2A from (S)—N-(benzyloxycarbonyl)-2-aminopentane-1,5-diol. Light yellow liquid.

B) (S)-2,2-Dimethyl-4-(3-oxo-propyl)-oxazolidine-3-carboxylic acid benzyl ester

The title compound was produced in analogy with examples 1/2B from (S)-4-(3-hydroxy-propyl)-2,2-dimethyl-oxazolidine-3-carboxylic acid benzyl ester. Light yellow liquid.

C) (S)-4-[3-((S)-4-Hydroxy-6-aza-spiro[2.5]oct-6-yl)-propyl]-2,2-dimethyl-oxazolidine-3-carboxylic acid benzyl ester The title compound was produced in analogy with examples 1/2C from (S)-2,2-dimethyl-4-(3-oxo-propyl)-oxazolidine-3-carboxylic acid benzyl ester and (S)-6-aza-spiro[2.5]octan-4-ol hydrochloride. Light yellow gum, MS (ISP)=403.3 (M+H)⁺.

D) [(S)-4-((S)-4-hydroxy-6-aza-spiro[2.5]oct-6-yl)-1-hydroxymethyl-butyl]-carbamic acid benzyl ester The title compound was produced in analogy with examples 1/2D from (S)-4-[3-((S)-4-hydroxy-6-aza-spiro[2.5]oct-6-yl)-propyl]-2,2-dimethyl-oxazolidine-3-carboxylic acid benzyl ester. Colourless oil, MS (ISP)=363.4 (M+H)⁺.

E) (S)-6-((S)-4-amino-5-hydroxy-pentyl)-6-aza-spiro[2.5]octan-4-ol

The title compound was produced in analogy with the procedure described in examples 1/2E from [(S)-4-((S)-4-hydroxy-6-aza-spiro[2.5]oct-6-yl)-1-hydroxymethyl-butyl]-carbamic acid benzyl ester. Yellow gum, MS (ISP)=229.3 (M+H)⁺.

F) (3S,6S)-3-[3-((S)-4-Hydroxy-6-aza-spiro[2.5]oct-6-yl)-propyl]-6,8a-dimethyl-5-oxo-hexahydro-oxazolo[3,2-a]pyrazine-7-carboxylic acid benzyl ester The title compound was produced in analogy with examples 1/2F from (S)-2-[benzyloxycarbonyl-(2-oxo-propyl)-amino]-propionic acid methyl ester (intermediate 2) and (S)-6-((S)-4-amino-5-hydroxy-pentyl)-6-aza-spiro[2.5]octan-4-ol. Light yellow gum, MS: 472.4 (M+H)+.

G) (3S,6S)-3-[3-((S)-4-Hydroxy-6-aza-spiro[2.5]oct-6-yl)-propyl]-6,8a-dimethyl-hexahydro-oxazolo[3,2-a]pyrazin-5-one A solution of (3S,6S)-3-[3-((S)-4-hydroxy-6-aza-spiro[2.5]oct-6-yl)-propyl]-6,8a-dimethyl-5-oxo-hexahydro-oxazolo[3,2-a]pyrazine-7-carboxylic acid benzyl ester (295 mg, 0.63 mmol) in MeOH (3 mL) was stirred for 1½ h at room temperature under a hydrogen atmosphere (1 bar) in the presence of palladium (10% on activated charcoal, 133 mg), then insoluble material was removed by filtration through diatomaceous earth. The filtrate was evaporated to afford the title compound (208 mg, 99%) Colourless gum, MS (ISP)=338.3 (M+H)⁺.

H) (3S,6S)-3-[3-((S)-4-Hydroxy-6-aza-spiro[2.5]oct-6-yl)-propyl]-6,8a-dimethyl-5-oxo-hexahydro-oxazolo[3,2-a]pyrazine-7-carboxylic acid (3,4-dichloro-phenyl)-amide 3,4-Dichlorophenyl isocyanate (28 mg, 0.15 mmol) was added at 0° C. to a solution of (3S,6S)-3-[3-((S)-4-hydroxy-6-aza-spiro[2.5]oct-6-yl)-propyl]-6,8a-dimethyl-hexahydro-oxazolo[3,2-a]pyrazin-5-one (50 mg, 0.15 mmol), then the ice bath was removed. After 30 min the reaction mixture was evaporated and the residue chromatographed (SiO₂; DCM→DCM/MeOH/25% aq. ammonia solution 90:10:0.25) to pruduce the title compound (57 mg, 73%). Colourless gum, MS: 525.3 (M+H)+.

Example 13

(3S,6S)-3-[3-((S)-4-Hydroxy-6-aza-spiro[2.5]oct-6-yl)-propyl]-6,8a-dimethyl-5-oxo-hexahydro-oxazolo[3,2-a]pyrazine-7-carboxylic acid (3-chloro-4-trifluoromethyl-phenyl)-amide

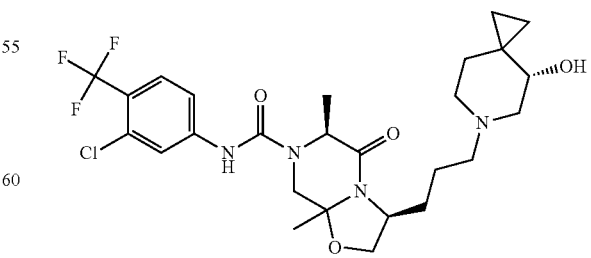

A solution of 4-amino-2-chlorobenzotrifluoride (30 mg, 0.15 mmol) in acetonitrile (0.5 mL) was added dropwise at 0° C. to a solution of bis-(trichloromethyl)-carbonate (17 mg, 50

μmol) in acetonitrile (0.5 mL) and pyridine (13 mg, 0.16 mmol). The ice bath was removed, then after 30 min a solution of (3S,6S)-3-[3-((S)-4-hydroxy-6-aza-spiro[2.5]oct-6-yl)-propyl]-6,8a-dimethyl-hexahydro-oxazolo[3,2-a]pyrazin-5-one (example 12G) in acetonitrile (0.5 mL) was added. After 3 h the reaction mixture was evaporated and the residue purified by chromatography (SiO$_2$; DCM→DCM/MeOH/25% aq. ammonia solution 90:10:0.25) to produce the title compound (39 mg, 47%). White solid, MS: 559.4 (M+H)$^+$.

Example 14

(3S,6S,8aR)-3-[2-((S)-4-Hydroxy-6-aza-spiro[2.5]oct-6-yl)-ethyl]-6,8a-dimethyl-5-oxo-hexahydro-oxazolo[3,2-a]pyrazine-7-carboxylic acid (3,4-dichloro-phenyl)-amide

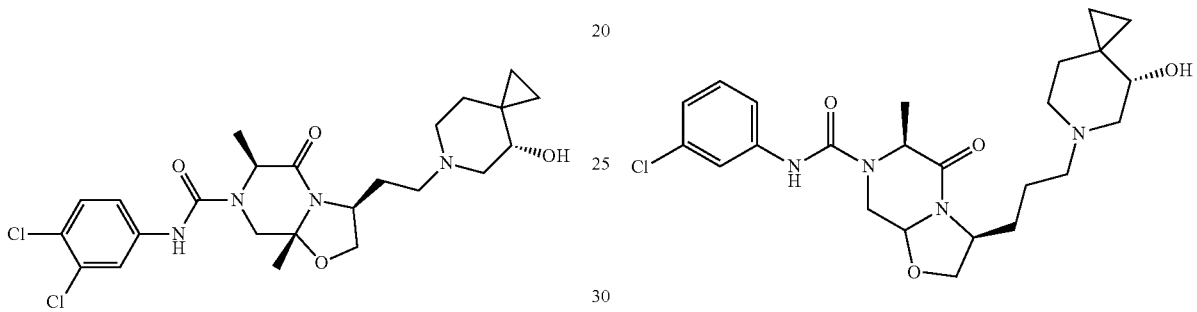

A) (3S,6S,8aR)-7-Benzyl-3-[2-((S)-4-hydroxy-6-aza-spiro[2.5]oct-6-yl)-ethyl]-6,8a-dimethyl-hexahydro-oxazolo[3,2-a]pyrazin-5-one The title compound was produced in analogy with examples 1/2F from (S)-2-[benzyl-(2-oxo-propyl)-amino]-propionic acid methyl ester (intermediate 3) and (S)-6-((S)-3-amino-4-hydroxy-butyl)-6-aza-spiro[2.5]octan-4-ol (examples 1/2E). Orange gum, MS: 414.4 (M+H)$^+$.

B) (3S,6S,8aR)-3-[2-((S)-4-Hydroxy-6-aza-spiro[2.5]oct-6-yl)-ethyl]-6,8a-dimethyl-hexahydro-oxazolo[3,2-a]pyrazin-5-one A solution of (3S,6S,8aR)-7-benzyl-3-[2-((S)-4-hydroxy-6-aza-spiro[2.5]oct-6-yl)-ethyl]-6,8a-dimethyl-hexahydro-oxazolo[3,2-a]pyrazin-5-one (160 mg, 0.39 mmol) in EtOH (3 mL) was stirred at 50° C. for 3 h under a hydrogen atmosphere (3 bar) in the presence of palladium (10% on activated charcoal, 63 mg), then insoluble material was removed by filtration through diatomaceous earth. The filtrate was evaporated to afford the title compound (104 mg, 83%). Off-white foam, MS: 324.5 (M+H)$^+$.

C) (3S,6S,8aR)-3-[2-((S)-4-Hydroxy-6-aza-spiro[2.5]oct-6-yl)-ethyl]-6,8a-dimethyl-5-oxo-hexahydro-oxazolo[3,2-a]pyrazine-7-carboxylic acid (3,4-dichloro-phenyl)-amide The title compound was produced in analogy with example 12H from (3S,6S,8aR)-7-benzyl-3-[2-((S)-4-hydroxy-6-aza-spiro[2.5]oct-6-yl)-ethyl]-6,8a-dimethyl-hexahydro-oxazolo[3,2-a]pyrazin-5-one and 3,4-dichlorophenyl isocyanate. White foam, MS: 511.4 (M+H)$^+$.

Example 15

(3S,6S)-3-[3-((S)-4-Hydroxy-6-aza-spiro[2.5]oct-6-yl)-propyl]-6-methyl-5-oxo-hexahydro-oxazolo[3,2-a]pyrazine-7-carboxylic acid (3-chloro-phenyl)-amide

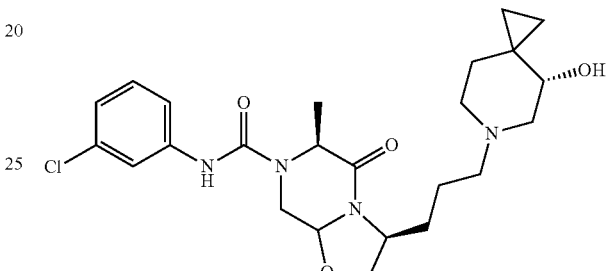

A) (3S,6S)-3-[3-((S)-4-Hydroxy-6-aza-spiro[2.5]oct-6-yl)-propyl]-6-methyl-5-oxo-hexahydro-oxazolo[3,2-a]pyrazine-7-carboxylic acid benzyl ester The title compound was produced in analogy with examples 1/2F from (S)-2-[benzyloxycarbonyl-(2-oxo-ethyl)-amino]-propionic acid methyl ester (intermediate 1) and (S)-6-((S)-4-amino-5-hydroxy-pentyl)-6-aza-spiro[2.5]octan-4-ol (example 12E). Brown foam, MS: 458.4 (M+H)$^+$.

B) (3S,6S)-3-[3-((S)-4-Hydroxy-6-aza-spiro[2.5]oct-6-yl)-propyl]-6-methyl-hexahydro-oxazolo[3,2-a]pyrazin-5-one The title compound was produced in analogy with example 12G from (3S,6S)-3-[3-((S)-4-hydroxy-6-aza-spiro[2.5]oct-6-yl)-propyl]-6-methyl-5-oxo-hexahydro-oxazolo[3,2-a]pyrazine-7-carboxylic acid benzyl ester. Light brown oil, MS: 324.3 (M+H)$^+$.

C) (3S,6S)-3-[3-((S)-4-Hydroxy-6-aza-spiro[2.5]oct-6-yl)-propyl]-6-methyl-5-oxo-hexahydro-oxazolo[3,2-a]pyrazine-7-carboxylic acid (3-chloro-phenyl)-amide The title compound was produced in analogy with example 12H from (3S,6S)-3-[3-((S)-4-hydroxy-6-aza-spiro[2.5]oct- 6-yl)-propyl]-6-methyl-hexahydro-oxazolo[3,2-a]pyrazin-5-one and 3,4-dichlorophenyl isocyanate. Light yellow foam, MS: 477.2 (M+H)+.

Example 16

(3S,6S)-3-[3-((S)-4-Hydroxy-6-aza-spiro[2.5]oct-6-yl)-propyl]-6-methyl-5-oxo-hexahydro-oxazolo[3,2-a]pyrazine-7-carboxylic acid (3,4-dichloro-phenyl)-amide

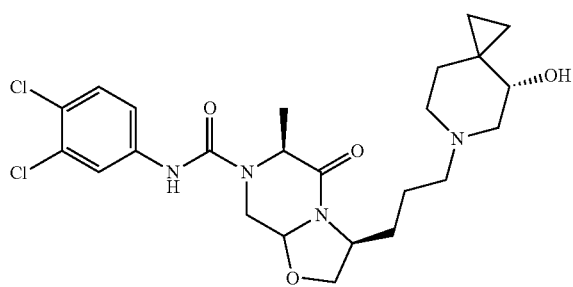 [SMILES: C[C@H]1C(=O)N2C(CN1C(=O)Nc1ccc(Cl)c(Cl)c1)OC[C@@H]2CCCN1CCC2(CC2)[C@H](O)C1]

The title compound was produced in analogy with example 12H from (3S,6S)-3-[3-((S)-4-hydroxy-6-aza-spiro[2.5]oct-6-yl)-propyl]-6-methyl-hexahydro-oxazolo[3,2-a]pyrazin-5-one (example 15C) and 3,4-dichlorophenyl isocyanate. Colourless gum, MS: 511.3 (M+H)+.

Examples 17 and 18

(3S,6S,8aS)-3-[3-((S)-4-Hydroxy-6-aza-spiro[2.5] oct-6-yl)-propyl]-6-methyl-5-oxo-hexahydro-oxazolo[3,2-a]pyrazine-7-carboxylic acid (3,4-dichloro-phenyl)-amide and (3S,6S,8aR)-3-[3-((S)-4-hydroxy-6-aza-spiro[2.5]oct-6-yl)-propyl]-6-methyl-5-oxo-hexahydro-oxazolo[3,2-a]pyrazine-7-carboxylic acid (3,4-dichloro-phenyl)-amide

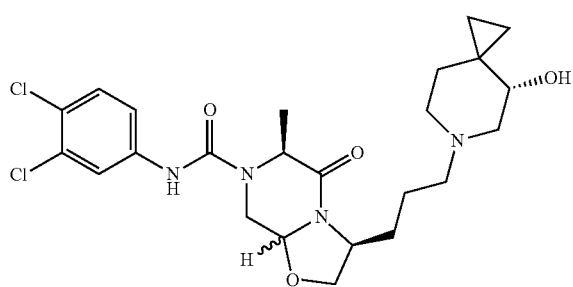

Example 17: (S)-epimer
Example 18: (R)-epimer

The mixture of epimers, (3S,6S)-3-[3-((S)-4-hydroxy-6-aza-spiro[2.5]oct-6-yl)-propyl]-6-methyl-5-oxo-hexahydro-oxazolo[3,2-a]pyrazine-7-carboxylic acid (3,4-dichloro-phenyl)-amide (example 16; 210 mg, 0.41 mmol) was separated by HPLC using a ReproSil Chiral-NR column as the stationary phase and heptane/EtOH 70:30 as the eluent. This afforded (3S,6S,8aS)-3-[3-((S)-4-hydroxy-6-aza-spiro[2.5] oct-6-yl)-propyl]-6-methyl-5-oxo-hexahydro-oxazolo[3,2-a]pyrazine-7-carboxylic acid (3,4-dichloro-phenyl)-amide [example 17; 106 mg, 50%; white foam, MS 511.2 (M+H)+] and (3S,6S,8aR)-3-[3-((S)-4-hydroxy-6-aza-spiro[2.5]oct-6-yl)-propyl]-6-methyl-5-oxo-hexahydro-oxazolo[3,2-a]pyrazine-7-carboxylic acid (3,4-dichloro-phenyl)-amide [example 18; 65 mg, 31%; white foam, MS: 511.2 (M+H)+].

Examples 19 and 20

(3S,6S,8aS)-3-[3-((S)-4-Hydroxy-6-aza-spiro[2.5] oct-6-yl)-propyl]-6-methyl-5-oxo-hexahydro-oxazolo[3,2-a]pyrazine-7-carboxylic acid (3-chloro-phenyl)-amide and (3S,6S,8aR)-3-[3-((S)-4-hydroxy-6-aza-spiro[2.5]oct-6-yl)-propyl]-6-methyl-5-oxo-hexahydro-oxazolo[3,2-a]pyrazine-7-carboxylic acid (3-chloro-phenyl)-amide

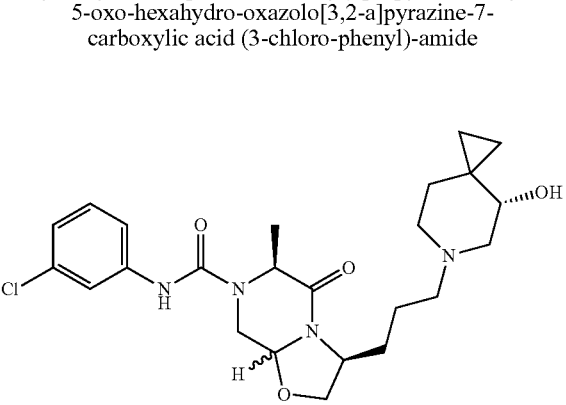

Example 19: (S)-epimer
Example 20: (R)-epimer

The title compounds were produced in analogy to examples 17/18 by HPLC separation of the mixture of epimers, (3S,6S)-3-[3-((S)-4-hydroxy-6-aza-spiro[2.5]oct-6-yl)-propyl]-6-methyl-5-oxo-hexahydro-oxazolo[3,2-a] pyrazine-7-carboxylic acid (3-chloro-phenyl)-amide (example 15). This produced the (S)-epimer [example 19; white foam, MS 477.2 (M+H)+] and the (R)-epimer [example 20; white foam, MS: 477.2 (M+H)+].

Examples 21 and 22

(3S,6S,8aS)-3-[3-((S)-4-Hydroxy-6-aza-spiro[2.5] oct-6-yl)-propyl]-6,8a-dimethyl-5-oxo-hexahydro-oxazolo[3,2-a]pyrazine-7-carboxylic acid (3,4-dichloro-phenyl)-amide and (3S,6S,8aR)-3-[3-((S)-4-hydroxy-6-aza-spiro[2.5]oct-6-yl)-propyl]-6,8a-dimethyl-5-oxo-hexahydro-oxazolo[3,2-a]pyrazine-7-carboxylic acid (3,4-dichloro-phenyl)-amide

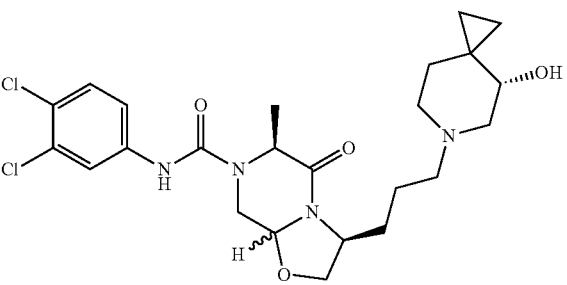

Example 21: (S)-epimer
Example 22: (R)-epimer

The mixture of epimers, (3S,6S)-3-[3-((S)-4-hydroxy-6-aza-spiro[2.5]oct-6-yl)-propyl]-6,8a-dimethyl-5-oxo-hexahydro-oxazolo[3,2-a]pyrazine-7-carboxylic acid (3,4-dichlorophenyl)-amide (example 12; 50 mg, 95 μmol) was separated by HPLC using a Lux™ Cellulose-2 column as the stationary phase and heptane/EtOH 70:30 as the eluent. This afforded (3S,6S,8aS)-3-[3-((S)-4-hydroxy-6-aza-spiro[2.5]oct-6-yl)-propyl]-6,8a-dimethyl-5-oxo-hexahydro-oxazolo[3,2-a]pyrazine-7-carboxylic acid (3,4-dichloro-phenyl)-amide [example 21; 3.5 mg, 7%; colourless gum, MS 525.2 (M+H)$^+$] and (3S,6S,8aR)-3-[3-((S)-4-hydroxy-6-aza-spiro[2.5]oct-6-yl)-propyl]-6,8a-dimethyl-5-oxo-hexahydro-oxazolo[3,2-a]pyrazine-7-carboxylic acid (3,4-dichloro-phenyl)-amide [example 22; 20 mg, 40%; white solid, MS: 525.2 (M+H)$^+$].

Example 23

(3S,6S)-3-[3-((S)-4-Hydroxy-6-aza-spiro[2.5]oct-6-yl)-3-oxo-propyl]-6-methyl-5-oxo-hexahydro-oxazolo[3,2-a]pyrazine-7-carboxylic acid (3,4-dichloro-phenyl)-amide

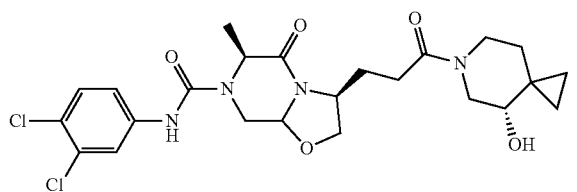 [SMILES: C[C@H]1C(=O)N2C(CN1C(=O)Nc1ccc(Cl)c(Cl)c1)OC[C@@H]2CCC(=O)N1CCC2(CC2)[C@H](O)C1]

A) (S)-2-Amino-pentane-1,5-diol

A solution of (S)—N-(benzyloxycarbonyl)-2-aminopentane-1,5-diol (2.00 g, 7.90 mmol) in EtOH (30 mL) was stirred at room temperature for 2 h under a hydrogen atmosphere (3 bar) in the presence of palladium (10% on activated charcoal, 1.68 g), then insoluble material was removed by filtration through diatomaceous earth. The filtrate was evaporated to afford the title compound (946 mg, 100%) as a colourless oil.

B) (3S,6S)-3-(3-Hydroxy-propyl)-6-methyl-5-oxo-hexahydro-oxazolo[3,2-a]pyrazine-7-carboxylic acid benzyl ester Condensation of (S)-2-[benzyloxycarbonyl-(2-oxo-ethyl)-amino]-propionic acid methyl ester (intermediate 1) with (S)-2-amino-pentane-1,5-diol in analogy with examples 1/2F produced a nearly statistical mixture of the title compound [light yellow gum, MS: 349.3 (M+H)$^+$] and (3S,5S)-5-hydroxymethyl-3-methyl-4-oxo-octahydro-9-oxa-2,4a-diazabenzocycloheptene-2-carboxylic acid benzyl ester [light yellow gum, MS:349.3 (M+H)'], which were separated by column chromatography (SiO$_2$; DCM→DCM/MeOH/25% aq. ammonia solution 90:10:0.25).

C) (3S,6S)-3-(2-Carboxy-ethyl)-6-methyl-5-oxo-hexahydro-oxazolo[3,2-a]pyrazine-7-carboxylic acid benzyl ester The title compound was produced in analogy with example 29C from (3S,6S)-3-(3-hydroxy-propyl)-6-methyl-5-oxo-hexahydro-oxazolo[3,2-a]pyrazine-7-carboxylic acid benzyl ester. Colourless gum, MS: 361.2 (M–H)$^-$.

D) (3S,6S)-3-[3-((S)-4-Hydroxy-6-aza-spiro[2.5]oct-6-yl)-3-oxo-propyl]-6-methyl-5-oxo-hexahydro-oxazolo[3,2-a]pyrazine-7-carboxylic acid benzyl ester The title compound was produced in analogy with example 29D from (3S,6S)-3-(2-carboxy-ethyl)-6-methyl-5-oxo-hexahydro-oxazolo[3,2-a]pyrazine-7-carboxylic acid benzyl ester and (S)-6-aza-spiro[2.5]octan-4-ol hydrochloride. White foam, MS: 472.4 (M+H)$^+$.

E) (3S,6S)-3-[3-((S)-4-Hydroxy-6-aza-spiro[2.5]oct-6-yl)-3-oxo-propyl]-6-methyl-5-oxo-hexahydro-oxazolo[3,2-a]pyrazine-7-carboxylic acid (3,4-dichloro-phenyl)-amide The title compound was produced in analogy with examples 1/2G from (3S,6S)-3-[3-((S)-4-hydroxy-6-aza-spiro[2.5]oct-6-yl)-3-oxo-propyl]-6-methyl-5-oxo-hexahydro-oxazolo[3,2-a]pyrazine-7-carboxylic acid benzyl ester and 3,4-dichlorophenyl isocyanate. White solid, MS: 525.4 (M+H)$^+$.

Example 24

(3S,6S,8aR)-3-[3-((S)-4-Hydroxy-6-aza-spiro[2.5]oct-6-yl)-3-oxo-propyl]-6-methyl-5-oxo-hexahydro-oxazolo[3,2-a]pyrazine-7-carboxylic acid (3-chloro-4-trifluoromethyl-phenyl)-amide

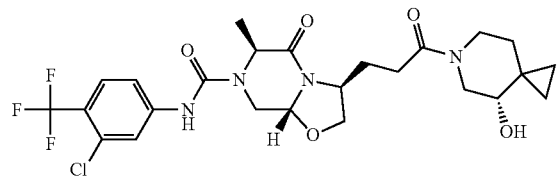 [SMILES: C[C@H]1C(=O)N2[C@@H](CCC(=O)N3CCC4(CC4)[C@H](O)C3)CO[C@@H]2CN1C(=O)Nc1ccc(C(F)(F)F)c(Cl)c1]

A) [(S)-4-((S)-4-Hydroxy-6-aza-spiro[2.5]oct-6-yl)-1-hydroxymethyl-4-oxo-butyl]-carbamic acid benzyl ester The title compound was produced in analogy with example 29D from (S)-5-hydroxy-4-(benzyloxycarbonylamino)-pentanoic acid [prepared from N-(benzyloxycarbonyl)-L-glutamic acid following the procedure described in Indian J. Chem. 1988, 27B, 1124] and (S)-6-aza-spiro[2.5]octan-4-ol hydrochloride. Light yellow gum, MS: 377.4 (M+H)$^+$.

B) (S)-4-Amino-5-hydroxy-1-((S)-4-hydroxy-6-aza-spiro[2.5]oct-6-yl)-pentan-1-one The title compound was produced in analogy with example 23A from [(S)-4-((S)-4-hydroxy-6-aza-spiro[2.5]oct-6-yl)-1-hydroxymethyl-4-oxo-butyl]-carbamic acid benzyl ester. Colourless gum, MS: 243.4 (M+H)$^+$.

C) (3S,6S,8aR)-3-[3-((S)-4-Hydroxy-6-aza-spiro[2.5]oct-6-yl)-3-oxo-propyl]-6-methyl-5-oxo-hexahydro-oxazolo[3,2-a]pyrazine-7-carboxylic acid benzyl ester Condensation of (S)-2-[benzyloxycarbonyl-(2-oxo-ethyl)-amino]-propionic acid methyl ester (intermediate 1) with (S)-

4-amino-5-hydroxy-1-((S)-4-hydroxy-6-aza-spiro[2.5]oct-6-yl)-pentan-1-one in analogy with examples 1/2F produced a nearly statistical mixture of the title compound [light brown gum, MS: 472.4 (M+H)⁺], and its epimer, (3S,6S,8aS)-3-[3-((S)-4-hydroxy-6-aza-spiro[2.5]oct-6-yl)-3-oxo-propyl]-6-methyl-5-oxo-hexahydro-oxazolo[3,2-a]pyrazine-7-carboxylic acid benzyl ester [light brown gum, MS: 472.4 (M+H)¹], which were separated by column chromatography (SiO₂; DCM→DCM/MeOH/25% aq. ammonia solution 90:10:0.25).

D) (3S,6S,8aR)-3-[3-((S)-4-Hydroxy-6-aza-spiro [2.5]oct-6-yl)-3-oxo-propyl]-6-methyl-hexahydro-oxazolo[3,2-a]pyrazin-5-one The title compound was produced in analogy with example 1E from (3S,6S,8aR)-3-[3-((S)-4-hydroxy-6-aza-spiro[2.5]oct-6-yl)-3-oxo-propyl]-6-methyl-5-oxo-hexahydro-oxazolo[3,2-a]pyrazine-7-carboxylic acid benzyl ester. Light yellow gum, MS: 338.2 (M+H)⁺.

E) (3S,6S,8aR)-3-[3-((S)-4-Hydroxy-6-aza-spiro [2.5]oct-6-yl)-3-oxo-propyl]-6-methyl-5-oxo-hexahydro-oxazolo[3,2-a]pyrazine-7-carboxylic acid (3-chloro-4-trifluoromethyl-phenyl)-amide The title compound was produced in analogy with example 13 from (3S,6S,8aR)-3-[3-((S)-4-hydroxy-6-aza-spiro[2.5]oct-6-yl)-3-oxo-propyl]-6-methyl-hexahydro-oxazolo[3,2-a]pyrazin-5-one and 4-amino-2-chlorobenzotrifluoride. Colourless gum, MS: 559.2 (M+H)⁺.

Example 25

(3S,6S,8aS)-3-[3-((S)-4-Hydroxy-6-aza-spiro[2.5]oct-6-yl)-3-oxo-propyl]-6-methyl-5-oxo-hexahydro-oxazolo[3,2-a]pyrazine-7-carboxylic acid (3-chloro-4-trifluoromethyl-phenyl)-amide

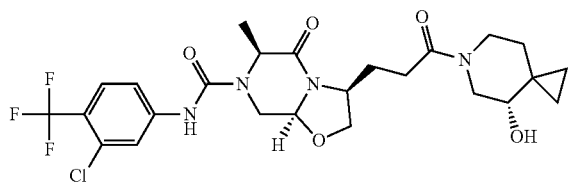 [SMILES: C[C@H]1C(=O)N2[C@@H](CCC(=O)N3CCC4(CC4)[C@H](O)C3)CO[C@H]2CN1C(=O)Nc1ccc(C(F)(F)F)c(Cl)c1]

A) (3S,6S,8aS)-3-[3-((S)-4-Hydroxy-6-aza-spiro [2.5]oct-6-yl)-3-oxo-propyl]-6-methyl-hexahydro-oxazolo[3,2-a]pyrazin-5-one The title compound was produced in analogy with example 1E from (3S,6S,8aS)-3-[3-((S)-4-hydroxy-6-aza-spiro[2.5]oct-6-yl)-3-oxo-propyl]-6-methyl-5-oxo-hexahydro-oxazolo[3,2-a]pyrazine-7-carboxylic acid benzyl ester (example 24C). Colourless gum, MS: 338.2 (M+H)⁺.

B) (3S,6S,8aS)-3-[3-((S)-4-Hydroxy-6-aza-spiro [2.5]oct-6-yl)-3-oxo-propyl]-6-methyl-5-oxo-hexahydro-oxazolo[3,2-a]pyrazine-7-carboxylic acid (3-chloro-4-trifluoromethyl-phenyl)-amide The title compound was produced in analogy with example 13 from (3S,6S,8aS)-3-[3-((S)-4-hydroxy-6-aza-spiro[2.5]oct-6-yl)-3-oxo-propyl]-6-methyl-hexahydro-oxazolo[3,2-a]pyrazin-5-one and 4-amino-2-chlorobenzotrifluoride. Colourless gum, MS: 559.2 (M+H)⁺.

Example 26

(3S,6S,8aR)-7-[(E)-3-(3-Chloro-4-fluoro-phenyl)-acryloyl]-3-[3-((S)-4-hydroxy-6-aza-spiro[2.5]oct-6-yl)-3-oxo-propyl]-6-methyl-hexahydro-oxazolo[3,2-a]pyrazin-5-one

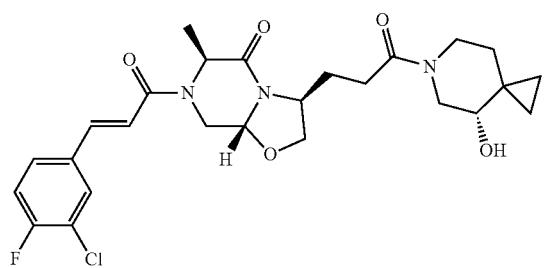 [SMILES: C[C@H]1C(=O)N2[C@@H](CCC(=O)N3CCC4(CC4)[C@H](O)C3)CO[C@@H]2CN1C(=O)/C=C/c1ccc(F)c(Cl)c1]

The title compound was produced in analogy with example 29D from (3S,6S,8aR)-3-[3-((S)-4-hydroxy-6-aza-spiro[2.5]oct-6-yl)-3-oxo-propyl]-6-methyl-hexahydro-oxazolo[3,2-a]pyrazin-5-one (example 24D) and 3-chloro-4-fluorocinnamic acid. White solid, MS: 520.3 (M+H)⁺.

Example 27

(3S,6S,8aS)-7-[(E)-3-(3-Chloro-4-fluoro-phenyl)-acryloyl]-3-[3-((S)-4-hydroxy-6-aza-spiro[2.5]oct-6-yl)-3-oxo-propyl]-6-methyl-hexahydro-oxazolo[3,2-a]pyrazin-5-one

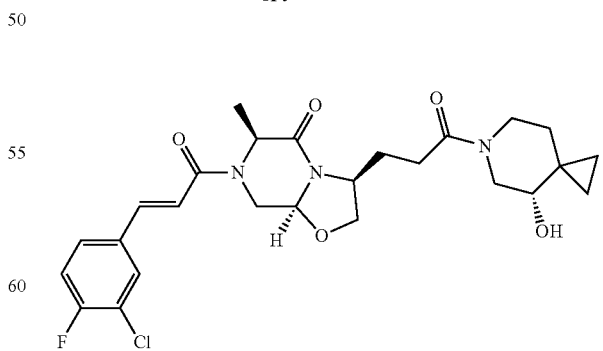

The title compound was produced in analogy with example 29D from (3S,6S,8aS)-3-[3-((S)-4-hydroxy-6-aza-spiro[2.5]oct-6-yl)-3-oxo-propyl]-6-methyl-hexahydro-oxazolo[3,2- a]pyrazin-5-one (example 25A) and 3-chloro-4-fluorocinnamic acid. White solid, MS: 520.3 (M+H)+.

Example 28

(3S,5S)-5-((S)-4-Hydroxy-6-aza-spiro[2.5]oct-6-ylmethyl)-3-methyl-4-oxo-octahydro-9-oxa-2,4a-diaza-benzocycloheptene-2-carboxylic acid (3,4-dichloro-phenyl)-amide

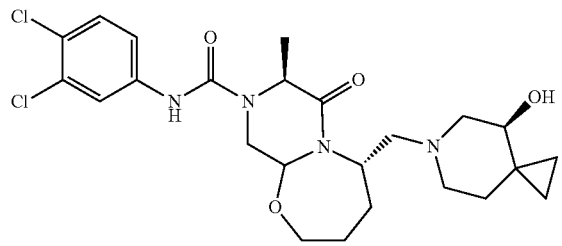 [SMILES: C[C@H]1C(=O)N2C(CN1C(=O)Nc1ccc(Cl)c(Cl)c1)OCCC[C@H]2CN1CCC2(CC2)[C@H](O)C1]

A) (3S,5S)-5-((S)-4-Hydroxy-6-aza-spiro[2.5]oct-6-ylmethyl)-3-methyl-4-oxo-octahydro-9-oxa-2,4a-diaza-benzocycloheptene-2-carboxylic acid benzyl ester 2,2,6,6-Tetramethylpiperidine-1-oxyl radical (0.05 mg, 0.3 µmol) was added at room temperature to a suspension of (3S,5S)-5-hydroxymethyl-3-methyl-4-oxo-octahydro-9-oxa-2,4a-diaza-benzocycloheptene-2-carboxylic acid benzyl ester (example 23B, 102 mg, 0.29 mmol) and trichloroisocyanuric acid (72 mg, 0.29 mmol) in DCM (1 mL), then after 5 min the mixture was washed with 1 M aq. sodium sulfite solution and brine. The organic layer was dried over magnesium sulfate, filtered, and evaporated. The residue [(3S,5S)-5-oxomethyl-3-methyl-4-oxo-octahydro-9-oxa-2,4a-diaza-benzocycloheptene-2-carboxylic acid benzyl ester] was dissolved in DCM (1 mL) and added dropwise at room temperature to a suspension of (S)-6-aza-spiro[2.5]octan-4-ol hydrochloride (48 mg, 0.29 mmol), Et₃N (30 mg, 0.29 mmol), HOAc (35 mg, 0.58 mmol) and sodium triacetoxyborohydride (70 mg, 0.32 mmol) in DCM, then after 16 h the reaction mixture was cooled to 0° C. and partitioned between EtOAc and 1 M aq. sodium carbonate solution. The organic layer was washed with brine, dried over magnesium sulfate, filtered, and evaporated. Chromatography (SiO₂; DCM→DCM/MeOH/25% aq. ammonia solution 90:10:0.25) produced the title compound (70 mg, 52%). Light yellow gum, MS: 458.4 (M+H)+.

B) (3S,5S)-5-((S)-4-Hydroxy-6-aza-spiro[2.5]oct-6-ylmethyl)-3-methyl-4-oxo-octahydro-9-oxa-2,4a-diaza-benzocycloheptene-2-carboxylic acid (3,4-dichloro-phenyl)-amide The title compound was produced in analogy with examples 1/2G from (3S,5S)-5-((S)-4-hydroxy-6-aza-spiro[2.5]oct-6-ylmethyl)-3-methyl-4-oxo-octahydro-9-oxa-2,4a-diaza-benzocycloheptene-2-carboxylic acid benzyl ester and 3,4-dichlorophenyl isocyanate. Colourless gum, MS: 511.3 (M+H)+.

Example 29

(3S,6S)-3-[2-((S)-4-Hydroxy-6-aza-spiro[2.5]oct-6-yl)-2-oxo-ethyl]-6-methyl-5-oxo-hexahydro-oxazolo[3,2-a]pyrazine-7-carboxylic acid (3,4-dichloro-phenyl)-amide

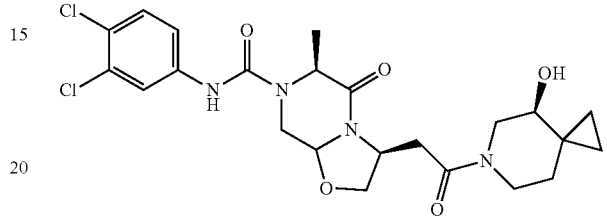

A) (S)-2-Amino-butane-1,4-diol

The title compound was produced in analogy with example 23A from (S)—N-(benzyloxycarbonyl)-2-aminobutane-1,4-diol. Colourless oil.

B) (3S,6S)-3-(2-Hydroxy-ethyl)-6-methyl-5-oxo-hexahydro-oxazolo[3,2-a]pyrazine-7-carboxylic acid benzyl ester Condensation of (S)-2-[benzyloxycarbonyl-(2-oxo-ethyl)-amino]-propionic acid methyl ester (intermediate 1) with (S)-2-amino-butane-1,4-diol in analogy with examples 1/2F produced a nearly statistical mixture of the title compound [light yellow gum, MS: 335.5 (M+H)+] and (4S,7S)-4-hydroxymethyl-7-methyl-6-oxo-hexahydro-pyrazino[2,1-b][1,3]oxazine-8-carboxylic acid benzyl ester [light yellow gum, MS: 335.4 (M+H)¹], which were separated by column chromatography (SiO₂; DCM→DCM/MeOH/25% aq. ammonia solution 90:10:0.25).

C) (3S,6S)-3-Carboxymethyl-6-methyl-5-oxo-hexahydro-oxazolo[3,2-a]pyrazine-7-carboxylic acid benzyl ester Solutions of sodium chlorite (66 mg, 0.58 mmol in 0.5 mL water) and 10% aq. sodium hypochlorite (4 µL, 6 µmol in 0.2 mL water) were added simultaneously at 35° C. to a mixture of (3S,6S)-3-(2-hydroxy-ethyl)-6-methyl-5-oxo-hexahydro-oxazolo[3,2-a]pyrazine-7-carboxylic acid benzyl ester (98 mg, 0.29 mmol), 2,2,6,6-tetramethylpiperidine-1-oxyl radical (3 mg, 20 µmol) in 1 M aq. potassium phosphate buffer (pH 6.85; 0.75 mL) and acetonitrile (1 mL). The reaction mixture was heated at 45° C. for 16 h, then cooled to 0° C., diluted with water and EtOAc and treated with 1 M sodium thiosulfate solution. The pH was then set to 3-4 by addition of 2 M aq. hydrochloric acid solution. The organic layer was washed with brine, dried over magnesium sulfate, filtered, and evaporated. Chromatography (SiO₂; DCM→DCM/MeOH/25% aq. ammonia solution 90:10:0.25) afforded the title compound (84 mg, 82%). Colourless gum, MS: 347.1 (M−H)⁻.

D) (3S,6S)-3-[2-((S)-4-Hydroxy-6-aza-spiro[2.5]oct-6-yl)-2-oxo-ethyl]-6-methyl-5-oxo-hexahydro-oxazolo[3,2-a]pyrazine-7-carboxylic acid benzyl ester -(7-Azabenzotriazol-1-yl)-N,N,N',N'-tetramethyluronium hexafluorophosphate (138 mg, 0.36 mmol) was added to a solution of (3S,6S)-3-carboxymethyl-6-methyl-5-oxo-hexahydro-oxazolo[3,2-a]pyrazine-7-carboxylic acid benzyl ester (84 mg, 0.24 mmol), (S)-6-aza-spiro[2.5]octan-4-ol hydrochloride (39 mg, 0.24 mmol) and 4-methylmorpholine (73 mg, 0.73 mmol) in DMF(1 mL), then after 16 h the reaction mixture was partitioned between EtOAc and water. The organic layer was washed with brine, dried over magnesium sulfate, filtered, and evaporated. Chromatography (SiO$_2$, DCM→DCM/MeOH/25% aq. ammonia solution 90:10:0.25) afforded the title compound (106 mg, 96%). Colourless gum, MS: 458.5 (M+H)$^+$.

E) (3S,6S)-3-[2-((S)-4-Hydroxy-6-aza-spiro[2.5]oct-6-yl)-2-oxo-ethyl]-6-methyl-5-oxo-hexahydro-oxazolo[3,2-a]pyrazine-7-carboxylic acid (3,4-dichloro-phenyl)-amide The title compound was produced in analogy with examples 1/2G from (3S,6S)-3-[2-((S)-4-hydroxy-6-aza-spiro[2.5]oct-6-yl)-2-oxo-ethyl]-6-methyl-5-oxo-hexahydro-oxazolo[3,2-a]pyrazine-7-carboxylic acid benzyl ester and 3,4-dichlorophenyl isocyanate. White solid, MS: 511.4 (M+H)$^+$.

Example 30

(4S,7S)-4-((S)-4-Hydroxy-6-aza-spiro[2.5]oct-6-ylmethyl)-7-methyl-6-oxo-hexahydro-pyrazino[2,1-b][1,3]oxazine-8-carboxylic acid (3,4-dichloro-phenyl)-amide

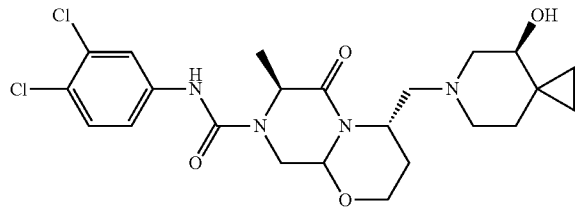 [SMILES: C[C@H]1C(=O)N2C(CN1C(=O)Nc1ccc(Cl)c(Cl)c1)OCC[C@H]2CN1CCC2(CC2)[C@H](O)C1]

A) (4S,7S)-4-((S)-4-Hydroxy-6-aza-spiro[2.5]oct-6-ylmethyl)-7-methyl-6-oxo-hexahydro-pyrazino[2,1-b][1,3]oxazine-8-carboxylic acid benzyl ester The title compound was produced in analogy with example 28A from (4S,7S)-4-hydroxymethyl-7-methyl-6-oxo-hexahydro-pyrazino[2,1-b][1,3]oxazine-8-carboxylic acid benzyl ester by oxidation to (4S,7S)-4-oxomethyl-7-methyl-6-oxo-hexahydro-pyrazino[2,1-b][1,3]oxazine-8-carboxylic acid benzyl ester, which was subjected to a reductive amination reaction with (S)-6-aza-spiro[2.5]octan-4-ol hydrochloride. Light yellow gum, MS: 444.3 (M+H)$^+$.

B) (4S,7S)-4-((S)-4-Hydroxy-6-aza-spiro[2.5]oct-6-ylmethyl)-7-methyl-6-oxo-hexahydro-pyrazino[2,1-b][1,3]oxazine-8-carboxylic acid (3,4-dichloro-phenyl)-amide The title compound was produced in analogy with examples 1/2G from (4S,7S)-4-((S)-4-hydroxy-6-aza-spiro[2.5]oct-6-ylmethyl)-7-methyl-6-oxo-hexahydro-pyrazino[2,1-b][1,3]oxazine-8-carboxylic acid benzyl ester and 3,4-dichlorophenyl isocyanate. Colourless gum, MS: 497.3 (M+H)$^+$.

Example 31

(4S,7S,9aR)-4-[2-((S)-4-Hydroxy-6-aza-spiro[2.5]oct-6-yl)-ethyl]-7-methyl-6-oxo-hexahydro-pyrazino[2,1-c][1,4]oxazine-8-carboxylic acid (3,4-dichloro-phenyl)-amide

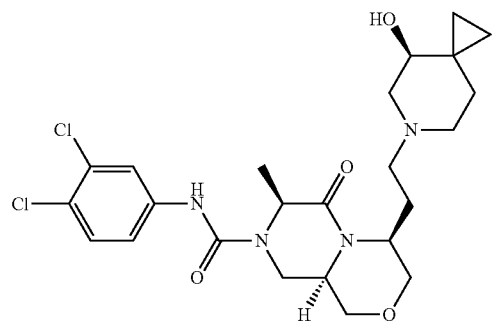 [SMILES: C[C@H]1C(=O)N2[C@@H](CCN3CCC4(CC4)[C@H](O)C3)COC[C@H]2CN1C(=O)Nc1ccc(Cl)c(Cl)c1]

A) (3S,5R)-3-Allyl-5-hydroxymethyl-morpholine-4-carboxylic acid tert-butyl ester Osmium tetroxide solution (2.5% in tert-butyl alcohol, 0.49 mL, 77 μmol) was added at 0° C. to a solution of (S)-3-allyloxy-2-tert-butoxycarbonylamino-propionic acid methyl ester (Org. Lett. 2007, 9, 3061; 1.00 g, 3.86 mmol) and 50% aq. 4-methylmorpholine-4-oxide solution (1.81 g, 7.71 mmol) in THF/water 2:1 (8 mL), then after 1 h sodium periodate (2.47 g, 11.6 mmol) was added. The ice bath was removed, then after 2 h the reaction mixture was treated with 10% aq. sodium sulfite solution (5.2 mL) and stirred for an additional 3 h, then poured upon water and extracted with EtOAc. The organic layer was washed with brine, dried over magnesium sulfate, filtered, and evaporated. The residue [(3S,5R)-3-hydroxy-5-[((S)-1-methoxycarbonyl-ethylamino)-methyl]-morpholine-4-carboxylic acid tert-butyl ester] was dissolved in MeOH (5 mL), treated with toluene 4-sulfonic acid monohydrate (66 mg, 0.39 mmol), stirred for 1 h at room temperature, and concentrated in vacuo. The residue was redissolved in EtOAc and washed with 1 M aq. sodium hydrogencarbonate solution. The organic layer was dried over magnesium sulfate, filtered, and evaporated to afford crude (3S,5R)-3-methoxy-5-[((S)-1-methoxycarbonyl-ethylamino)-methyl]-morpholine-4-carboxylic acid tert-butyl ester (908 mg) as a brown oil. This was dissolved in DCM (10 mL), cooled to −78° C., then boron trifluoride etherate (928 mg, 6.54 mmol) and allyl trimethylsilane (560 mg, 4.90 mmol) were added, then after 2 h the reaction mixture was poured upon sat. aq. sodium hydrogencarbonate solution. The organic layer was dried over magnesium sulfate, filtered, and evaporated. Chromatography (SiO$_2$; heptane/EtOAc 70:30) afforded the title compound (601 mg, 55%). Colourless oil, MS: 308.1 (M+Na)$^+$.

B) (3S,5R)-3-Allyl-5-hydroxymethyl-morpholine-4-carboxylic acid tert-butyl ester A solution of (3S,5R)-3-allyl-5-hydroxymethyl-morpholine-4-carboxylic acid tert-butyl ester (595 mg, 2.09 mmol) in THF (3 mL) was added at 0° C. to a suspension of lithium aluminum hydride (158 mg, 4.17 mmol) in THF (3 mL), then after 10 min excess reagent was destroyed by careful addition of 1 M aq. sodium hydroxide solution. The reaction mixture was extracted with EtOAc, the organic layer was washed with brine, dried over magnesium sulfate, filtered, and evaporated to afford the title compound (472 mg, 88%). Colourless oil, MS: 258.3 (M+H)$^+$.

C) (3S,5S)-3-Allyl-5-formyl-morpholine-4-carboxylic acid tert-butyl ester

Dimethyl sulfoxide (498 mg, 6.38 mmol) was added at −70° C. to a solution of oxalyl chloride (405 mg, 3.19 mmol) in DCM (5 mL), then after 15 min a solution of (3S,5S)-3-allyl-5-hydroxymethyl-morpholine-4-carboxylic acid tert-butyl ester (547 mg, 2.13 mmol) in DCM (3 mL) was added. The reaction mixture was stirred at −70° C. for 30 min, then treated with Et$_3$N (1.29 g, 12.8 mmol), then after 20 min the ice bath was removed. After 30 min the reaction mixture was washed with sat. aq. sodium hydrogencarbonate solution. The organic layer was washed with brine, dried over magnesium sulfate, filtered, and evaporated to afford the title compound (608 mg) as a light yellow gum, which was directly used in the next step.

D) (3S,5R)-3-Allyl-5-{[benzyloxycarbonyl-((S)-1-methoxycarbonyl-ethyl)-amino]-methyl}-morpholine-4-carboxylic acid tert-butyl ester Sodium triacetoxyborohydride (628 mg, 2.96 mmol) were added at 0° C. to a solution of (3S,5S)-3-allyl-5-formyl-morpholine-4-carboxylic acid tert-butyl ester (608 mg, 2.12 mmol) and L-alanine methyl ester hydrochloride (295 mg, 2.12 mmol) in DCM (8 mL), then after 16 h the reaction mixture was partitioned between sat. aq. sodium hydrogencarbonate solution and DCM. The organic layer was washed with brine, dried over magnesium sulfate, filtered, and evaporated. The residue [(3S,5R)-3-allyl-5-[((S)-1-methoxycarbonyl-ethylamino)-methyl]-morpholine-4-carboxylic acid tert-butyl ester, MS: 343.3 (M+H)$^+$] was taken up in acetone (3.5 mL) and water (3.5 mL), then after addition of sodium hydrogencarbonate (355 mg, 4.23 mmol), the reaction mixture was cooled to 0° C. and treated with benzyl chloroformate (380 mg, 2.12 mmol). The ice bath was removed, then after 1 h the reaction mixture was partitioned between EtOAc and water. The organic layer was dried over magnesium sulfate, filtered, and evaporated to afford the title compound (1.01 g, 100%). Light yellow oil, MS: 477.3 (M+H)$^+$.

E) (4S,7S,9aR)-4-Allyl-7-methyl-6-oxo-hexahydro-pyrazino[2,1-c][1,4]oxazine-8-carboxylic acid benzyl ester The title compound was produced in analogy with examples 33/34C from (3S,5R)-3-allyl-5-{[benzyloxycarbonyl-((S)-1-methoxycarbonyl-ethyl)-amino]-methyl}-morpholine-4-carboxylic acid tert-butyl ester. Light yellow oil, MS: 345.2 (M+H)$^+$.

F) (4S,7S,9aR)-4-[2-((S)-4-Hydroxy-6-aza-spiro[2.5]oct-6-yl)-ethyl]-7-methyl-6-oxo-hexahydro-pyrazino[2,1-c][1,4]oxazine-8-carboxylic acid benzyl ester The title compound was produced in analogy with examples 33/34D from (4S,7S,9aR)-4-allyl-7-methyl-6-oxo-hexahydro-pyrazino[2,1-c][1,4]oxazine-8-carboxylic acid benzyl ester and (S)-6-aza-spiro[2.5]octan-4-ol hydrochloride. Light yellow gum, MS: 458.5 (M+H)$^+$.

G) (4S,7S,9aR)-4-[2-((S)-4-Hydroxy-6-aza-spiro[2.5]oct-6-yl)-ethyl]-7-methyl-hexahydro-pyrazino[2,1-c][1,4]oxazin-6-one The title compound was produced in analogy with examples 1/2E from (4S,7S,9aR)-4-[2-((S)-4-hydroxy-6-aza-spiro[2.5]oct-6-yl)-ethyl]-7-methyl-6-oxo-hexahydro-pyrazino[2,1-c][1,4]oxazine-8-carboxylic acid benzyl ester. Light grey foam, MS: 324.5 (M+H)$^+$.

H) (4S,7S,9aR)-4-[2-((S)-4-Hydroxy-6-aza-spiro[2.5]oct-6-yl)-ethyl]-7-methyl-6-oxo-hexahydro-pyrazino[2,1-c][1,4]oxazine-8-carboxylic acid (3,4-dichloro-phenyl)-amide The title compound was produced in analogy with example 12H from (4S,7S,9aR)-4-[2-((S)-4-hydroxy-6-aza-spiro[2.5]oct-6-yl)-ethyl]-7-methyl-hexahydro-pyrazino[2,1-c][1,4]oxazin-6-one and 3,4-dichlorophenyl isocyanate. White foam, MS: 511.3 (M+H)$^+$.

Example 32

(4S,7S,9aR)-4-[2-((S)-4-Hydroxy-6-aza-spiro[2.5]oct-6-yl)-ethyl]-7-methyl-6-oxo-hexahydro-pyrazino[2,1-c][1,4]oxazine-8-carboxylic acid (3-chloro-4-trifluoromethyl-phenyl)-amide

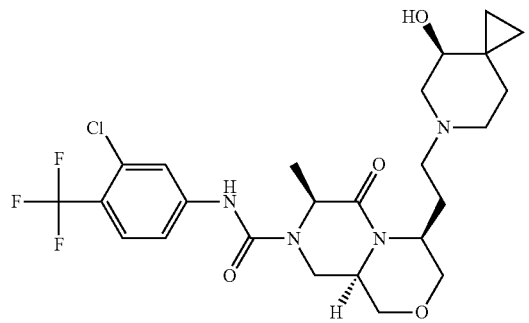 [SMILES: C[C@H]1C(=O)N2[C@@H](CCN3CCC4(CC4)[C@H](O)C3)COC[C@H]2CN1C(=O)Nc1ccc(C(F)(F)F)c(Cl)c1]

The title compound was produced in analogy with example 13 from (4S,7S,9aR)-4-[2-((S)-4-hydroxy-6-aza-spiro[2.5]oct-6-yl)-ethyl]-7-methyl-hexahydro-pyrazino[2,1-c][1,4]

oxazin-6-one and 4-amino-2-chlorobenzotrifluoride (example 31G). Light yellow solid, MS: 545.3 (M+H)⁺.

Examples 33 and 34

(3S,6R,8aS)-6-[2-((S)-4-Hydroxy-6-aza-spiro[2.5]oct-6-yl)-ethyl]-3-methyl-4-oxo-hexahydro-pyrrolo[1,2-a]pyrazine-2-carboxylic acid (3,4-dichloro-phenyl)-amide and (3S,6S,8aS)-6-[2-((S)-4-hydroxy-6-aza-spiro[2.5]oct-6-yl)-ethyl]-3-methyl-4-oxo-hexahydro-pyrrolo[1,2-a]pyrazine-2-carboxylic acid (3,4-dichloro-phenyl)-amide

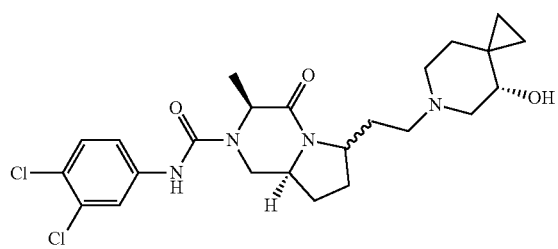

Example 33: (R)-epimer
Example 34: (S)-epimer

A) (S)-2-Allyl-5-formyl-pyrrolidine-1-carboxylic acid tert-butyl ester

The title compound was produced in analogy with example 31C from (5S)-2-allyl-5-hydroxymethyl-pyrrolidine-1-carboxylic acid tert-butyl ester (*Org. Lett.* 2004, 6, 1469). Colourless liquid, MS: 240.2 (M+H)⁺.

B) (S)-2-Allyl-5-{[[benzyloxycarbonyl-((S)-1-methoxycarbonyl-ethyl)-amino]-methyl}-pyrrolidine-1-carboxylic acid tert-butyl ester The title compound was produced in analogy with example 31D from (S)-2-allyl-5-formyl-pyrrolidine-1-carboxylic acid tert-butyl ester by reductive amination with L-alanine methyl ester hydrochloride, followed by derivatisation of the resultant secondary amine, (S)-2-allyl-5-[((S)-1-methoxycarbonyl-ethylamino)-methyl]-pyrrolidine-1-carboxylic acid tert-butyl ester with benzyl chloroformate. Colourless liquid, MS: 461.2 (M+H)⁺.

C) (3S,8aS)-6-Allyl-3-methyl-4-oxo-hexahydro-pyrrolo[1,2-a]pyrazine-2-carboxylic acid benzyl ester A solution of (S)-2-allyl-5-{[benzyloxycarbonyl-((S)-1-methoxycarbonyl-ethyl)-amino]-methyl}-pyrrolidine-1-carboxylic acid tert-butyl ester (298 mg, 0.65 mmol) in hydrogen chloride solution (4 M in 1,4-dioxane, 3 mL) was stirred at room temperature for 2 h, then evaporated. The residue was taken up in MeOH (3 mL), then after addition of potassium carbonate (268 mg, 1.94 mmol) the suspension was stirred at room temperature for 16 h, then partitioned between sat. aq. ammonium chloride solution and EtOAc. The organic layer was washed with brine, dried over magnesium sulfate, and evaporated to afford the title compound (221 mg, 100%). Light brown solid, MS: 329.4 (M+H)⁺.

D) (3S,8aS)-6-[2-((S)-4-Hydroxy-6-aza-spiro[2.5]oct-6-yl)-ethyl]-3-methyl-4-oxo-hexahydro-pyrrolo[1,2-a]pyrazine-2-carboxylic acid benzyl ester Sodium periodate (206 mg, 0.96 mmol) and osmium tetroxide solution (2.5% in tert-butyl alcohol, 33 μL, 3.3 μmol) were added at 0° C. to a suspension of (3S,8aS)-6-allyl-3-methyl-4-oxo-hexahydro-pyrrolo[1,2-a]pyrazine-2-carboxylic acid benzyl ester (110 mg, 0.33 mmol) in acetone (1 mL) and water (1 mL). After removal of the ice bath the reaction mixture was stirred for 3 h at room temperature, then partitioned between EtOAc and water. The organic layer was washed with brine, dried over magnesium sulfate, and evaporated to furnish (3S,8aS)-3-methyl-4-oxo-6-(2-oxo-ethyl)-hexahydro-pyrrolo[1,2-a]pyrazine-2-carboxylic acid benzyl ester [MS: 331.2 (M+H)⁺]. This was dissolved in DCM (1 mL) and added at room temperature to a suspension of (S)-6-aza-spiro[2.5]octan-4-ol hydrochloride (53 mg, 0.33 mmol), Et₃N (33 mg, 0.33 mmol), HOAc (39 mg, 0.66 mmol), and sodium triacetoxyborohydride (77 mg, 0.36 mmol) in DCM (1 mL). After 16 h the reaction mixture was partitioned between EtOAc and 1 M aq. sodium carbonate solution. The organic layer was washed with brine, dried over magnesium sulfate, filtered, and evaporated. Chromatography (SiO₂; DCM→DCM/MeOH/25% aq. ammonia solution 90:10:0.25) afforded the title compound (88 mg, 62%). Light yellow gum, MS: 442.4 (M+H)⁺.

E) (3S,8aS)-6-[2-((S)-4-Hydroxy-6-aza-spiro[2.5]oct-6-yl)-ethyl]-3-methyl-4-oxo-hexahydro-pyrrolo[1,2-a]pyrazine-2-carboxylic acid (3,4-dichloro-phenyl)-amide The title compound was produced in analogy with examples 1/2G from (3S,8aS)-6-[2-((S)-4-hydroxy-6-aza-spiro[2.5]oct-6-yl)-ethyl]-3-methyl-4-oxo-hexahydro-pyrrolo[1,2-a]pyrazine-2-carboxylic acid benzyl ester and 3,4-dichlorophenyl isocyanate. White solid, MS: 495.4 (M+H)⁺.

F) (3S,6R,8aS)-6-[2-((S)-4-Hydroxy-6-aza-spiro[2.5]oct-6-yl)-ethyl]-3-methyl-4-oxo-hexahydro-pyrrolo[1,2-a]pyrazine-2-carboxylic acid (3,4-dichloro-phenyl)-amide and (3S,6S,8aS)-6-[2-((S)-4-hydroxy-6-aza-spiro[2.5]oct-6-yl)-ethyl]-3-methyl-4-oxo-hexahydro-pyrrolo[1,2-a]pyrazine-2-carboxylic acid (3,4-dichloro-phenyl)-amide The mixture of epimers, (3S,8aS)-6-[2-((S)-4-hydroxy-6-aza-spiro[2.5]oct-6-yl)-ethyl]-3-methyl-4-oxo-hexahydro-pyrrolo[1,2-a]pyrazine-2-carboxylic acid (3,4-dichloro-phenyl)-amide (55 mg, 0.11 mmol) was separated by HPLC using a ReproSil Chiral-NR column as the stationary phase and heptane/EtOH 60:40 as the eluent. This afforded (3S,6R,8aS)-6-[2-((S)-4-hydroxy-6-aza-spiro[2.5]oct-6-yl)-ethyl]-3-methyl-4-oxo-hexahydro-pyrrolo[1,2-a]pyrazine-2-carboxylic acid (3,4-dichloro-phenyl)-amide [example 33; 22 mg, 40%; white solid, MS: 495.2 (M+H)⁺] and (3S,6S,8aS)-6-[2-((S)-4-hydroxy-6-aza-spiro[2.5]oct-6-yl)-ethyl]-3-methyl-4-oxo-hexahydro-pyrrolo[1,2-a]pyrazine-2-carboxylic acid (3,4-dichloro-phenyl)-amide [example 34; 18 mg, 33%; white solid, MS: 495.2 (M+H)⁺].

Example 35

(3S,6S,8aR)-3-[3-((S)-4-Hydroxy-6-aza-spiro[2.5] oct-6-yl)-3-oxo-propyl]-6-methyl-5-oxo-hexahydro-oxazolo[3,2-a]pyrazine-7-carboxylic acid (3,4-dichloro-phenyl)-amide

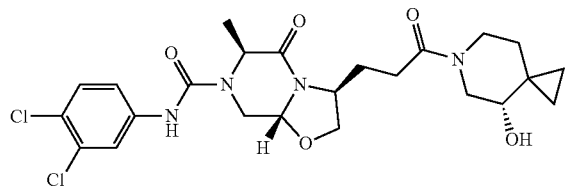 [SMILES: C[C@H]1C(=O)N2[C@@H](CCC(=O)N3CCC4(CC4)[C@H](O)C3)CO[C@@H]2CN1C(=O)Nc1ccc(Cl)c(Cl)c1]

The title compound was produced in analogy with example 12H from (3S,6S,8aR)-3-[3-((S)-4-hydroxy-6-aza-spiro[2.5] oct-6-yl)-3-oxo-propyl]-6-methyl-hexahydro-oxazolo[3,2-a]pyrazin-5-one (example 24D) and 3,4-dichlorophenyl isocyanate. White solid, MS: 525.3 (M+H)⁺.

Example 36

(3S,6S,8aS)-3-[3-((S)-4-Hydroxy-6-aza-spiro[2.5] oct-6-yl)-3-oxo-propyl]-6-methyl-5-oxo-hexahydro-oxazolo[3,2-a]pyrazine-7-carboxylic acid (3,4-dichloro-phenyl)-amide

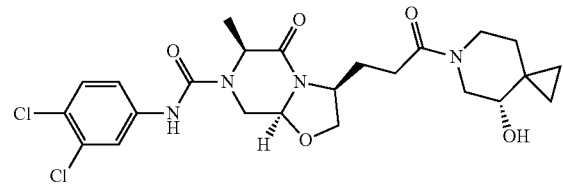 [SMILES: C[C@H]1C(=O)N2[C@@H](CCC(=O)N3CCC4(CC4)[C@H](O)C3)CO[C@H]2CN1C(=O)Nc1ccc(Cl)c(Cl)c1]

The title compound was produced in analogy with example 12H from (3S,6S,8aS)-3-[3-((S)-4-hydroxy-6-aza-spiro[2.5] oct-6-yl)-3-oxo-propyl]-6-methyl-hexahydro-oxazolo[3,2-a]pyrazin-5-one (example 25A) and 3,4-dichlorophenyl isocyanate. White solid, MS: 525.3 (M+H)⁺.

Example 37

(3S,6S)-3-[3-((S)-4-Hydroxy-6-aza-spiro[2.5]oct-6-yl)-3-oxo-propyl]-6,8a-dimethyl-5-oxo-hexahydro-oxazolo[3,2-a]pyrazine-7-carboxylic acid (3-chloro-4-trifluoromethyl-phenyl)-amide

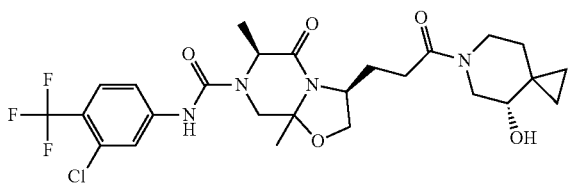 [SMILES: C[C@H]1C(=O)N2[C@@H](CCC(=O)N3CCC4(CC4)[C@H](O)C3)COC2(C)CN1C(=O)Nc1ccc(C(F)(F)F)c(Cl)c1]

A) (3S,6S)-3-[3-((S)-4-Hydroxy-6-aza-spiro[2.5] oct-6-yl)-3-oxo-propyl]-6,8a-dimethyl-5-oxo-hexahydro-oxazolo[3,2-a]pyrazine-7-carboxylic acid benzyl ester The title compound was produced in analogy with examples 1/2F from (S)-2-[benzyloxycarbonyl-(2-oxo-propyl)-amino]-propionic acid methyl ester (intermediate 2) and (S)-6-((S)-4-amino-5-hydroxy-pentyl)-6-aza-spiro[2.5]octan-4-ol (example 12E). Light brown gum, MS: 486.5 (M+H)⁺.

B) (3S,6S)-3-[3-((S)-4-Hydroxy-6-aza-spiro[2.5]oct-6-yl)-3-oxo-propyl]-6,8a-dimethyl-hexahydro-oxazolo[3,2-a]pyrazin-5-one The title compound was produced in analogy with examples 1/2E from (3S,6S)-3-[3-((S)-4-hydroxy-6-aza-spiro[2.5]oct-6-yl)-3-oxo-propyl]-6,8a-dimethyl-5-oxo-hexahydro-oxazolo[3,2-a]pyrazine-7-carboxylic acid benzyl ester. Light yellow gum, MS: 352.4 (M+H)⁺.

C) (3S,6S)-3-[3-((S)-4-Hydroxy-6-aza-spiro[2.5]oct-6-yl)-3-oxo-propyl]-6,8a-dimethyl-5-oxo-hexahydro-oxazolo[3,2-a]pyrazine-7-carboxylic acid (3-chloro-4-trifluoromethyl-phenyl)-amide The title compound was produced in analogy with example 13 from (3S,6S)-3-[3-((S)-4-hydroxy-6-aza-spiro[2.5]oct-6-yl)-3-oxo-propyl]-6,8a-dimethyl-hexahydro-oxazolo[3,2-a]pyrazin-5-one and 4-amino-2-chlorobenzotrifluoride. Light yellow gum, MS: 573.2 (M+H)⁺.

Example 38

(3S,9aR)-6-[2-((S)-4-Hydroxy-6-aza-spiro[2.5]oct-6-yl)-ethyl]-3-methyl-4-oxo-octahydro-pyrido[1,2-a]pyrazine-2-carboxylic acid (3,4-dichloro-phenyl)-amide

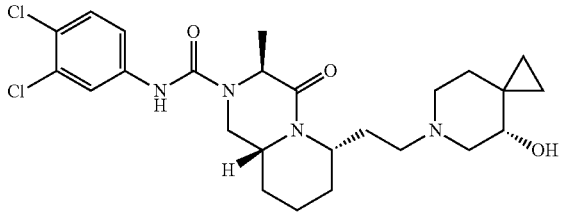

A) (R)-6-Allyl-piperidine-1,2-dicarboxylic acid 1-tert-butyl ester 2-methyl ester Lithium triethylborohydride solution (1 M in THF, 11.2 mL, 11.2 mmol) was added dropwise at −78° C. to a solution of 1-(tert-butoxycarbonyl)-R-6-oxopipecolic acid methyl ester (*J. Org. Chem.* 1996, 61, 8496; 2.40 g, 9.33 mmol) in THF (30 mL), then after 90 min the reaction mixture was poured upon half-saturated aq. sodium hydrogencarbonate solution and extracted with EtOAc. The organic layer was washed with brine, dried over magnesium sulfate, filtered, and evaporated. The residue was dissolved in MeOH (25 mL), treated with toluene 4-sulfonic acid monohydrate (177 mg, 0.93 mmol), stirred for 2 h at room temperature, then concentrated under vacuum. The residue was chromatographed (SiO₂; heptane-EtOAc gradient) to afford (R)-6-methoxy-piperidine-1,2-dicarboxylic acid 1-tert-butyl ester 2-methyl ester (2.1 g) as mixture of epimers. This was dissolved in DCM (25 mL), cooled to −78° C., and treated with allyl trimethylsilane (1.30 g, 11.4 mmol) and boron trifluoride etherate (2.16 g, 15.2 mmol), then after 2 h the reaction mixture was poured onto sat. aq. sodium hydrogencarbonate solution. The organic layer was washed with brine, dried over magnesium sulfate, filtered, and evaporated. Chromatography (SiO₂; heptane-EtOAc gradient) afforded the title compound (362 mg, 14%). Light yellow liquid, MS: 184.2 (M+H−Boc)⁺.

B) (R)-2-Allyl-6-hydroxymethyl-piperidine-1-carboxylic acid tert-butyl ester

The title compound was produced in analogy with example 31B from (R)-6-allyl-piperidine-1,2-dicarboxylic acid 1-tert-butyl ester 2-methyl ester. Colourless oil, MS: 278.3 (M+Na)⁺.

C) (R)-2-Allyl-6-formyl-piperidine-1-carboxylic acid tert-butyl ester

The title compound was produced in analogy with example 31C from (R)-2-allyl-6-hydroxymethyl-piperidine-1-carboxylic acid tert-butyl ester. Colourless oil.

D) (R)-2-Allyl-6-{[benzyloxycarbonyl-((S)-1-methoxycarbonyl-ethyl)-amino]-methyl}-piperidine-1-carboxylic acid tert-butyl ester The title compound was produced in analogy with example 31D from (R)-2-allyl-6-formyl-piperidine-1-carboxylic acid tert-butyl ester by reductive amination reaction with L-alanine methyl ester hydrochloride, followed by derivatisation of the resultant secondary amine, (R)-2-allyl-6-[((S)-1-methoxycarbonyl-ethylamino)-methyl]-piperidine-1-carboxylic acid tert-butyl ester with benzyl chloroformate. Yellow oil, MS: 475.3 (M+H)⁺.

E) (3S,9aR)-6-Allyl-3-methyl-4-oxo-octahydro-pyrido[1,2-a]pyrazine-2-carboxylic acid benzyl ester The title compound was produced in analogy with examples 33/34C from (R)-2-allyl-6-{[benzyloxycarbonyl-((S)-1-methoxycarbonyl-ethyl)-amino]-methyl}-piperidine-1-carboxylic acid tert-butyl ester. Yellow gum, MS: 343.2 (M+H)⁺.

F) (3S,9aR)-6-[2-((S)-4-Hydroxy-6-aza-spiro[2.5]oct-6-yl)-ethyl]-3-methyl-4-oxo-octahydro-pyrido[1,2-a]pyrazine-2-carboxylic acid benzyl ester The title compound was produced in analogy with examples 33/34D from (3S,9aR)-6-allyl-3-methyl-4-oxo-octahydro-pyrido[1,2-a]pyrazine-2-carboxylic acid benzyl ester and (S)-6-aza-spiro[2.5]octan-4-ol hydrochloride. White foam, MS: 456.4 (M+H)⁺.

G) (3S,9aR)-6-[2-((S)-4-Hydroxy-6-aza-spiro[2.5]oct-6-yl)-ethyl]-3-methyl-4-oxo-octahydro-pyrido[1,2-a]pyrazine-2-carboxylic acid (3,4-dichloro-phenyl)-amide The title compound was produced in analogy with examples 1/2G from (3S,9aR)-6-[2-((S)-4-hydroxy-6-aza-spiro[2.5]oct-6-yl)-ethyl]-3-methyl-4-oxo-octahydro-pyrido[1,2-a]pyrazine-2-carboxylic acid benzyl ester and 3,4-dichlorophenyl isocyanate. White foam, MS: 509.3 (M+H)⁺.

Example 39

(3S,6S,9aR)-6-[2-((S)-4-Hydroxy-6-aza-spiro[2.5]oct-6-yl)-ethyl]-3-methyl-4-oxo-octahydro-pyrido[1,2-a]pyrazine-2-carboxylic acid (3,4-dichloro-phenyl)-amide

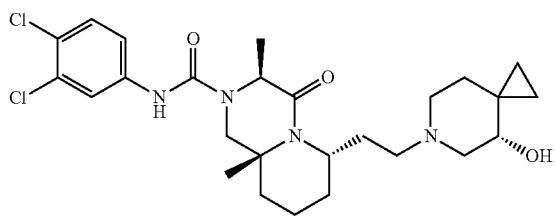 [SMILES: C[C@H]1C(=O)N2[C@H](CCN3CCC4(CC4)[C@H](O)C3)CCC[C@]2(C)CN1C(=O)Nc1ccc(Cl)c(Cl)c1]

The mixture of epimers, (3S,9aR)-6-[2-((S)-4-Hydroxy-6-aza-spiro[2.5]oct-6-yl)-ethyl]-3-methyl-4-oxo-octahydro-pyrido[1,2-a]pyrazine-2-carboxylic acid (3,4-dichloro-phenyl)-amide (example 38; 41 mg, 80 μmol) was separated by HPLC using a Chiralpak® AD column as the stationary phase and heptane/EtOH 70:30 as the eluent. This afforded (3S,9aR)-6-[2-((S)-4-hydroxy-6-aza-spiro[2.5]oct-6-yl)-ethyl]-3-methyl-4-oxo-octahydro-pyrido[1,2-a]pyrazine-2-carboxylic acid (3,4-dichloro-phenyl)-amide (16 mg, 39%; light yellow foam, MS: 509.3 (M+H)⁺). The other epimer, (3S,6R,9aR)-6-[2-((S)-4-hydroxy-6-aza-spiro[2.5]oct-6-yl)-ethyl]-3-methyl-4-oxo-octahydro-pyrido[1,2-a]pyrazine-2-carboxylic acid (3,4-dichloro-phenyl)-amide, was not obtained in pure form.

Example 40

(4R,7S,9aS)-4-[2-((S)-4-Hydroxy-6-aza-spiro[2.5]oct-6-yl)-ethyl]-7-methyl-6-oxo-hexahydro-pyrazino[2,1-c][1,4]oxazine-8-carboxylic acid (3,4-dichloro-phenyl)-amide

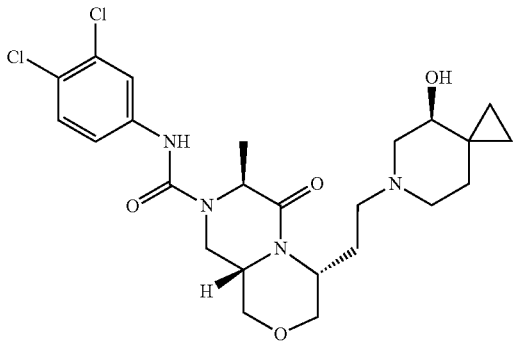 [SMILES: C[C@H]1C(=O)N2[C@H](CCN3CCC4(CC4)[C@H](O)C3)COC[C@@H]2CN1C(=O)Nc1ccc(Cl)c(Cl)c1]

The title compound was produced in analogy with example 31, steps A-F, starting from (R)-3-allyloxy-2-tert-butoxycarbonylamino-propionic acid methyl ester, which was synthesised in the same manner as the (S)-enantiomer, as described in *Org. Lett.* 2007, 9, 3061. White foam, MS: 511.4 (M+H)⁺.

Example 41

(3S,6S,8aS)-6-[3-((S)-4-Hydroxy-6-aza-spiro[2.5]oct-6-yl)-propyl]-3-methyl-4-oxo-hexahydro-pyrrolo[1,2-a]pyrazine-2-carboxylic acid (3,4-dichloro-phenyl)-amide

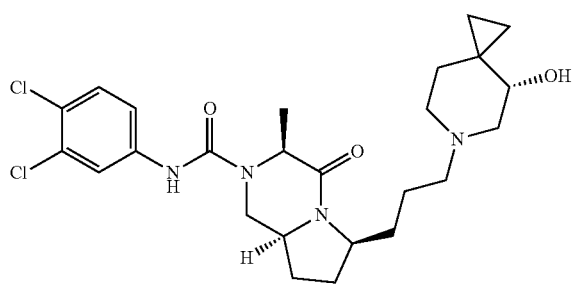 [SMILES: C[C@H]1C(=O)N2[C@@H](CCCN3CCC4(CC4)[C@H](O)C3)CC[C@H]2CN1C(=O)Nc1ccc(Cl)c(Cl)c1]

A) (S)-2-tert-Butoxycarbonylamino-5-oxo-non-8-enoic acid benzyl ester

To a solution of (S)-5-oxo-pyrrolidine-1,2-dicarboxylic acid 2-benzyl ester 1-tert-butyl ester (*Org. Lett.* 2004, 5, 1469; 450 mg, 1.41 mmol) in THF (10 mL) was added 3-butenylmagnesium bromide solution (0.5 M in THF, 3.38 mL, 1.69 mmoL) at −40° C., then after 3 h sat. aq. ammonium chloride solution (5 mL) was added. The reaction mixture was partitioned between EtOAc and water, the organic layer was washed with brine, dried over magnesium sulfate, filtered, and evaporated. Chromatography (SiO₂; heptane/EtOAc 2:1) afforded the title compound (329 mg, 62%). Colourless oil, MS: 376.4 (M+H)⁺.

B) (2S,5S)-2-But-3-enyl-5-hydroxymethyl-pyrrolidine-1-carboxylic acid tert-butyl ester A solution of (S)-2-tert-butoxycarbonylamino-5-oxo-non-8-enoic acid benzyl ester in DCM (5 mL) was added at −78° C. to a solution of triphenylsilane (496 mg, 1.90 mmol) and tris(pentafluorophenyl)borane (55 mg, 0.11 mmol) in DCM (5 mL), then after 30 min the cooling bath was removed and the reaction mixture was allowed to reach room temperature over 2 h. After cooling to −78° C. a solution of triphenylsilane (496 mg, 1.90 mmol) and tris(pentafluorophenyl)borane (55 mg, 0.11 mmol) in DCM (5 mL) was added to the reaction mixture, then after 30 min the cooling bath was removed. The reaction mixture was stirred at room temperature for 72 h, then treated with Et₃N (1 mL), then after 20 min partitioned between sat. aq. ammonium chloride solution and EtOAc. The organic layer was washed with brine, dried over magnesium sulfate, filtered, and evaporated. Chromatography (SiO₂; heptane/EtOAc 3:1) afforded an inseparable mixture of (2S,5S)-5-but-3-enyl-pyrrolidine-1,2-dicarboxylic acid 2-benzyl ester 1-tert-butyl ester and unspecified reagents. This mixture was dissolved in THF (2.5 mL) and added dropwise at 0° C. to a suspension of lithium aluminum hydride (65 mg, 1.71 mmol) in THF (2.5 mL), then after 20 min excess reagent was destroyed by addition of water (2 mL), EtOAc and 2 M aq. sodium hydroxide solution (1 mL). The reaction mixture was filtered through diatomaceous earth, the filtrate was washed with brine, dried over magnesium sulfate, filtered, and evaporated. Chromatography (SiO₂; heptane/EtOAc 3:1) afforded the title compound (179 mg, 82%). Colourless oil, MS: 256.3 (M+H)⁺.

C) (2S,5S)-2-But-3-enyl-5-formyl-pyrrolidine-1-carboxylic acid tert-butyl ester

The title compound was produced in analogy with example 31C from (2S,5S)-2-but-3-enyl-5-hydroxymethyl-pyrrolidine-1-carboxylic acid tert-butyl ester. Light yellow oil, MS: 254.3 (M+H)⁺.

D) (2S,5S)-2-{[Benzyloxycarbonyl-((S)-1-methoxycarbonyl-ethyl)-amino]-methyl}-5-but-3-enyl-pyrrolidine-1-carboxylic acid tert-butyl ester The title compound was produced in analogy with example 31D from (2S,5S)-2-but-3-enyl-5-formyl-pyrrolidine-1-carboxylic acid tert-butyl ester by reductive amination with L-alanine methyl ester hydrochloride, followed by derivatisation of the resultant secondary amine, (2S,5S)-2-but-3-enyl-5-[((S)-1-methoxycarbonyl-ethylamino)-methyl]-pyrrolidine-1-carboxylic acid tert-butyl ester with benzyl chloroformate. Colourless oil, MS: 475.3 (M+H)⁺.

E) (3S,6S,8aS)-6-But-3-enyl-3-methyl-4-oxo-hexahydro-pyrrolo[1,2-a]pyrazine-2-carboxylic acid benzyl ester The title compound was produced in analogy with examples 33/34C from (2S,5S)-2-{[benzyloxycarbonyl-((S)-1-methoxycarbonyl-ethyl)-amino]-methyl}-5-but-3-enyl-pyrrolidine-1-carboxylic acid tert-butyl ester. Colourless oil, MS: 343.2 (M+H)⁺.

F) (3S,6S,8aS)-6-[3-((S)-4-Hydroxy-6-aza-spiro[2.5]oct-6-yl)-propyl]-3-methyl-4-oxo-hexahydro-pyrrolo[1,2-a]pyrazine-2-carboxylic acid benzyl ester The title compound was produced in analogy with examples 33/34D from (3S,6S,8aS)-6-but-3-enyl-3-methyl-4-oxo-hexahydro-pyrrolo[1,2-a]pyrazine-2-carboxylic acid benzyl ester and (S)-6-aza-spiro[2.5]octan-4-ol hydrochloride. Colourless gum, MS: 456.5 (M+H)⁺.

G) (3S,6S,8aS)-6-[3-((S)-4-Hydroxy-6-aza-spiro[2.5]oct-6-yl)-propyl]-3-methyl-4-oxo-hexahydro-pyrrolo[1,2-a]pyrazine-2-carboxylic acid (3,4-dichloro-phenyl)-amide The title compound was produced in analogy with examples 1/2G from (3S,6S,8a5)-6-[3-((S)-4-hydroxy-6-aza-spiro[2.5]oct-6-yl)-propyl]-3-methyl-4-oxo-hexahydropyrrolo[1,2-a]pyrazine-2-carboxylic acid benzyl ester and 3,4-dichlorophenyl isocyanate. White solid, MS: 509.3 (M+H)⁺.

Example 42

(3S,6R,8aS)-6-[3-((S)-4-Hydroxy-6-aza-spiro[2.5]oct-6-yl)-3-oxo-propyl]-3-methyl-4-oxo-hexahydro-pyrrolo[1,2-a]pyrazine-2-carboxylic acid (3,4-dichloro-phenyl)-amide

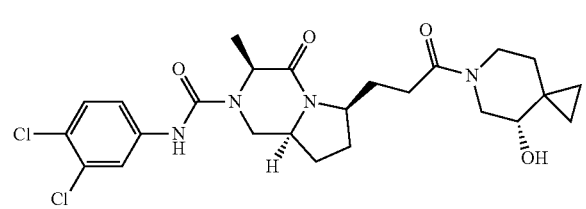 [SMILES: C[C@H]1C(=O)N2[C@@H](CCC(=O)N3CCC4(CC4)[C@H](O)C3)CC[C@H]2CN1C(=O)Nc1ccc(Cl)c(Cl)c1]

A) (3S,6R,8aS)-6-(2-Carboxy-ethyl)-3-methyl-4-oxo-hexahydro-pyrrolo[1,2-a]pyrazine-2-carboxylic acid benzyl ester A mixture of (3S,6S,8aS)-6-but-3-enyl-3-methyl-4-oxo-hexahydro-pyrrolo[1,2-a]pyrazine-2-carboxylic acid benzyl ester (example 41E; 80 mg, 0.23 mmol), sodium periodate (200 mg, 0.93 mmol) and ruthenium(III) chloride hydrate (3 mg, 12 µmol) in carbon tetrachloride (0.5 mL), acetonitrile (0.5 mL) and water (1 mL) was stirred at room temperature for 7½ h, then partitioned between DCM and water. The organic layer was washed with brine, dried over magnesium sulfate, filtered, and evaporated to afford the title compound (79 mg, 94%). Brown gum, MS: 361.2 (M+H)⁺.

B) (3S,6R,8aS)-6-[3-((S)-4-Hydroxy-6-aza-spiro[2.5]oct-6-yl)-3-oxo-propyl]-3-methyl-4-oxo-hexahydro-pyrrolo[1,2-a]pyrazine-2-carboxylic acid benzyl ester The title compound was produced in analogy with example 29D from (3S,6R,8aS)-6-(2-carboxy-ethyl)-3-methyl-4-oxo-hexahydro-pyrrolo[1,2-a]pyrazine-2-carboxylic acid benzyl ester and (S)-6-aza-spiro[2.5]octan-4-ol hydrochloride. Light yellow gum, MS: 470.4 (M+H)⁺.

C) (3S,6R,8aS)-6-[3-((S)-4-Hydroxy-6-aza-spiro[2.5]oct-6-yl)-3-oxo-propyl]-3-methyl-4-oxo-hexahydro-pyrrolo[1,2-a]pyrazine-2-carboxylic acid (3,4-dichloro-phenyl)-amide The title compound was produced in analogy with examples 1/2G from (3S,6R,8aS)-6-[3-((S)-4-hydroxy-6-aza-spiro[2.5]oct-6-yl)-3-oxo-propyl]-3-methyl-4-oxo-hexahydro-pyrrolo[1,2-a]pyrazine-2-carboxylic acid benzyl ester and 3,4-dichlorophenyl isocyanate. Colourless gum, MS: 523.3 (M+H)⁺.

Example 43

(3S,6R,8aS)-6-[3-((S)-4-Hydroxy-6-aza-spiro[2.5]oct-6-yl)-3-oxo-propyl]-3-methyl-4-oxo-hexahydro-pyrrolo[1,2-a]pyrazine-2-carboxylic acid (3-chloro-4-trifluoromethyl-phenyl)-amide

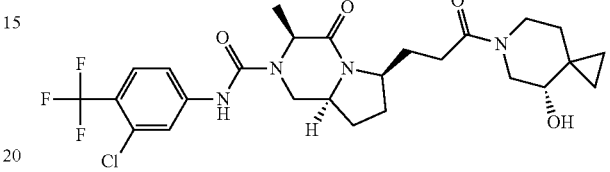

The title compound was produced in analogy with examples 1/2G from (3S,6R,8aS)-6-[3-((S)-4-hydroxy-6-aza-spiro[2.5]oct-6-yl)-3-oxo-propyl]-3-methyl-4-oxo-hexahydro-pyrrolo[1,2-a]pyrazine-2-carboxylic acid benzyl ester (example 42B) and 3-chloro-4-(trifluoromethyl)phenyl isocyanate (Eur. Pat. Appl. EP 290902). Colourless gum, MS: 557.2 (M+H)⁺.

Example 44

(3S,6S,8aS)-3-Methyl-4-oxo-6-[3-(3,3,4,4-tetrafluoro-pyrrolidin-1-yl)-propyl]-hexahydro-pyrrolo[1,2-a]pyrazine-2-carboxylic acid (3,4-dichloro-phenyl)-amide

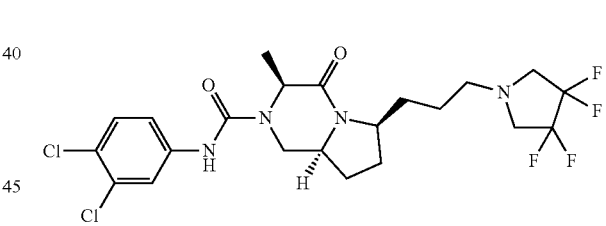

A) (3S,6S,8aS)-3-Methyl-4-oxo-6-[3-(3,3,4,4-tetrafluoro-pyrrolidin-1-yl)-propyl]-hexahydro-pyrrolo[1,2-a]pyrazine-2-carboxylic acid benzyl ester The title compound was produced in analogy with examples 33/34D from (3S,6S,8aS)-6-but-3-enyl-3-methyl-4-oxo-hexahydro-pyrrolo[1,2-a]pyrazine-2-carboxylic acid benzyl ester (example 41E) and 3,3,4,4-tetrafluoropyrrolidine hydrochloride. Colourless gum, MS: 472.4 (M+H)⁺.

B) (3S,6S,8aS)-3-Methyl-4-oxo-6-[3-(3,3,4,4-tetrafluoro-pyrrolidin-1-yl)-propyl]-hexahydro-pyrrolo[1,2-a]pyrazine-2-carboxylic acid (3,4-dichloro-phenyl)-amide The title compound was produced in analogy with examples 1/2G from (3S,6S,8aS)-3-methyl-4-oxo-6-[3-(3,3,4,4-tetrafluoro-pyrrolidin-1-yl)-propyl]-hexahydro-pyrrolo

[1,2-a]pyrazine-2-carboxylic acid benzyl ester and 3,4-dichlorophenyl isocyanate. Colourless gum, MS: 525.2 (M+H)⁺.

Example 45

(3S,6S,8aS)-6-[3-(3,3-Difluoro-pyrrolidin-1-yl)-propyl]-3-methyl-4-oxo-hexahydro-pyrrolo[1,2-a]pyrazine-2-carboxylic acid (3,4-dichloro-phenyl)-amide

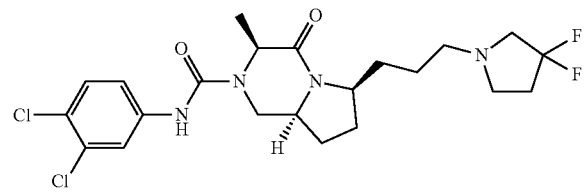 [SMILES: C[C@H]1C(=O)N2[C@@H](CCCN3CCC(F)(F)C3)CC[C@H]2CN1C(=O)Nc1ccc(Cl)c(Cl)c1]

A) (3S,6S,8aS)-3-Methyl-4-oxo-6-[3-(3,3-difluoro-pyrrolidin-1-yl)-propyl]-hexahydro-pyrrolo[1,2-a]pyrazine-2-carboxylic acid benzyl ester The title compound was produced in analogy with examples 33/34D from (3S,6S,8aS)-6-but-3-enyl-3-methyl-4-oxo-hexahydro-pyrrolo[1,2-a]pyrazine-2-carboxylic acid benzyl ester (example 41E) and 3,3-difluoropyrrolidine hydrochloride. Colourless gum, MS: 436.3 (M+H)⁺.

B) (3S,6S,8aS)-3-Methyl-4-oxo-6-[3-(3,3-difluoro-pyrrolidin-1-yl)-propyl]-hexahydro-pyrrolo[1,2-a]pyrazine-2-carboxylic acid (3,4-dichloro-phenyl)-amide The title compound was produced in analogy with examples 1/2G from (3S,6S,8aS)-3-methyl-4-oxo-6-[3-(3,3-difluoro-pyrrolidin-1-yl)-propyl]-hexahydro-pyrrolo[1,2-a]pyrazine-2-carboxylic acid benzyl ester and 3,4-dichlorophenyl isocyanate. Colourless gum, MS: 489.3 (M+H)⁺.

Example 46

(3S,6S,8aS)-6-[3-(4,4-Difluoro-piperidin-1-yl)-propyl]-3-methyl-4-oxo-hexahydro-pyrrolo[1,2-a]pyrazine-2-carboxylic acid (3,4-dichloro-phenyl)-amide

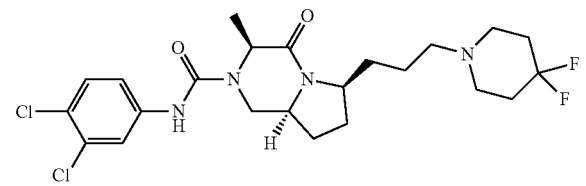 [SMILES: C[C@H]1C(=O)N2[C@@H](CCCN3CCC(F)(F)CC3)CC[C@H]2CN1C(=O)Nc1ccc(Cl)c(Cl)c1]

A) (3S,6S,8aS)-3-Methyl-4-oxo-6-[3-(4,4-difluoro-piperidin-1-yl)-propyl]-hexahydro-pyrrolo[1,2-a]pyrazine-2-carboxylic acid benzyl ester The title compound was produced in analogy with examples 33/34D from (3S,6S,8aS)-6-but-3-enyl-3-methyl-4-oxo-hexahydro-pyrrolo[1,2-a]pyrazine-2-carboxylic acid benzyl ester (example 41E) and 4,4-difluoropiperidine hydrochloride. Colourless gum, MS: 450.3 (M+H)⁺.

B) (3S,6S,8aS)-3-Methyl-4-oxo-6-[3-(4,4-difluoro-piperidin-1-yl)-propyl]-hexahydro-pyrrolo[1,2-a]pyrazine-2-carboxylic acid (3,4-dichloro-phenyl)-amide The title compound was produced in analogy with examples 1/2G from (3S,6S,8aS)-3-methyl-4-oxo-6-[3-(4,4-difluoro-piperidin-1-yl)-propyl]-hexahydro-pyrrolo[1,2-a]pyrazine-2-carboxylic acid benzyl ester and 3,4-dichlorophenyl isocyanate. Colourless gum, MS: 503.2 (M+H)⁺.

Example 47

(3S,6S,8aS)-6-[3-(3,3-Difluoro-piperidin-1-yl)-propyl]-3-methyl-4-oxo-hexahydro-pyrrolo[1,2-a]pyrazine-2-carboxylic acid (3,4-dichloro-phenyl)-amide

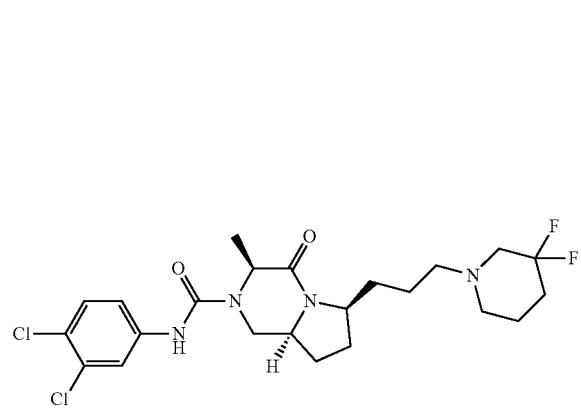 [SMILES: C[C@H]1C(=O)N2[C@@H](CCCN3CCCC(F)(F)C3)CC[C@H]2CN1C(=O)Nc1ccc(Cl)c(Cl)c1]

A) (3S,6S,8aS)-3-Methyl-4-oxo-6-[3-(3,3-difluoro-piperidin-1-yl)-propyl]-hexahydro-pyrrolo[1,2-a]pyrazine-2-carboxylic acid benzyl ester The title compound was produced in analogy with examples 33/34D from (3S,6S,8aS)-6-but-3-enyl-3-methyl-4-oxo-hexahydro-pyrrolo[1,2-a]pyrazine-2-carboxylic acid benzyl ester (example 41E) and 3,3-difluoropiperidine hydrochloride. Colourless gum, MS: 450.3 (M+H)⁺.

B) (3S,6S,8aS)-3-Methyl-4-oxo-6-[3-(3,3-difluoro-piperidin-1-yl)-propyl]-hexahydro-pyrrolo[1,2-a]pyrazine-2-carboxylic acid (3,4-dichloro-phenyl)-amide The title compound was produced in analogy with examples 1/2G from (3S,6S,8aS)-3-methyl-4-oxo-6-[3-(3,3-difluoro-piperidin-1-yl)-propyl]-hexahydro-pyrrolo[1,2-a]

pyrazine-2-carboxylic acid benzyl ester and 3,4-dichlorophenyl isocyanate. White solid, MS: 503.2 (M+H)+.

Example 48

(7R,9aS)-5-Oxo-7-(2-piperidin-1-yl-ethyl)-hexahydro-pyrrolo[1,2-a][1,4]diazepine-2-carboxylic acid (3,4-dichloro-phenyl)-amide

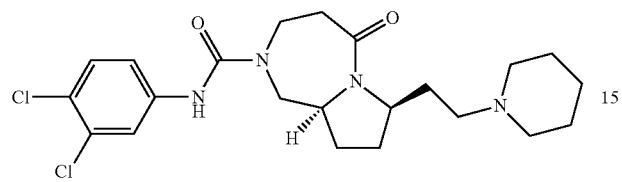

A) (2R,5S)-2-Allyl-5-formyl-pyrrolidine-1-carboxylic acid tert-butyl ester

The title compound was produced in analogy with example 31C from (2R,5S)-2-allyl-5-hydroxymethyl-pyrrolidine-1-carboxylic acid tert-butyl ester (*Org. Lett.* 2004, 6, 1469). Colourless oil, MS: 240.2 (M+H)+.

B) (2R,5S)-2-Allyl-5-{[benzyloxycarbonyl-(2-tert-butoxycarbonyl-ethyl)-amino]-methyl}-pyrrolidine-1-carboxylic acid tert-butyl ester The title compound was produced in analogy with example 31D from (2R,5S)-2-allyl-5-formyl-pyrrolidine-1-carboxylic acid tert-butyl ester by reductive amination with 3-aminopropionic acid tert-butyl ester hydrochloride, followed by derivatisation of the resultant secondary amine, (2R,5S)-2-allyl-5-[(2-tert-butoxycarbonyl-ethylamino)-methyl]-pyrrolidine-1-carboxylic acid tert-butyl ester with benzyl chloroformate. Colourless oil, MS: 503.4 (M+H)+.

C) (7R,9aS)-7-Allyl-5-oxo-hexahydro-pyrrolo[1,2-a][1,4]diazepine-2-carboxylic acid benzyl ester A solution of (2R,5S)-2-allyl-5-{[benzyloxycarbonyl-(2-tert-butoxycarbonyl-ethyl)-amino]-methyl}-pyrrolidine-1-carboxylic acid tert-butyl ester (875 mg, 1.74 mmol) in hydrogen chloride solution (4 M in 1,4-dioxane) was stirred for 2 1/2 h at room temperature, then concentrated in vacuo. The residue was taken up in N,N-dimethylformamide (10 mL), then 4-methylmorpholine (528 mg, 5.23 mmol) and O-(7-azabenzotriazol-1-yl)-N,N,N',N'-tetramethyluronium hexafluorophosphate (993 mg, 2.61 mmol) were added. The reaction mixture was stirred for 16 h at room temperature, then partitioned between water and ethyl acetate. The organic layer was washed with brine, dried over magnesium sulfate, filtered, and evaporated. Chromatography (SiO2; heptane-ethyl acetate gradient) afforded the title compound (479 mg, 84%). Colourless gum, MS: 329.4 (M+H)+.

D) (7R,9aS)-5-Oxo-7-(2-piperidin-1-yl-ethyl)-hexahydro-pyrrolo[1,2-a][1,4]diazepine-2-carboxylic acid benzyl ester The title compound was produced in analogy with examples 33/34D from (7R,9aS)-7-allyl-5-oxo-hexahydro-pyrrolo[1,2-a][1,4]diazepine-2-carboxylic acid benzyl ester and piperidine. Colourless gum, MS: 400.3 (M+H)+.

E) (7R,9aS)-5-Oxo-7-(2-piperidin-1-yl-ethyl)-hexahydro-pyrrolo[1,2-a][1,4]diazepine-2-carboxylic acid (3,4-dichloro-phenyl)-amide The title compound was produced in analogy with examples 1/2G from (7R,9aS)-5-oxo-7-(2-piperidin-1-yl-ethyl)-hexahydro-pyrrolo[1,2-a][1,4]diazepine-2-carboxylic acid benzyl ester and 3,4-dichlorophenyl isocyanate. Colourless gum, MS: 453.3 (M+H)+.

Example 49

(7R,9aS)-7-[2-((S)-4-Hydroxy-6-aza-spiro[2.5]oct-6-yl)-ethyl]-5-oxo-hexahydro-pyrrolo[1,2-a][1,4]diazepine-2-carboxylic acid (3,4-dichloro-phenyl)-amide

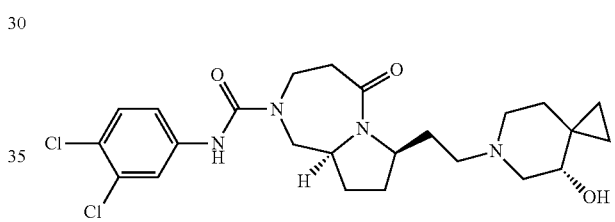

A) (7R,9aS)-7-[2-((S)-4-Hydroxy-6-aza-spiro[2.5]oct-6-yl)-ethyl]-5-oxo-hexahydro-pyrrolo[1,2-a][1,4]diazepine-2-carboxylic acid benzyl ester The title compound was produced in analogy with examples 33/34D from (7R,9aS)-7-allyl-5-oxo-hexahydro-pyrrolo[1,2-a][1,4]diazepine-2-carboxylic acid benzyl ester (example 48C) and (S)-6-aza-spiro[2.5]octan-4-ol hydrochloride. Colourless gum, MS: 442.4 (M+H)+.

B) (7R,9aS)-7-[2-((S)-4-Hydroxy-6-aza-spiro[2.5]oct-6-yl)-ethyl]-5-oxo-hexahydro-pyrrolo[1,2-a][1,4]diazepine-2-carboxylic acid (3,4-dichloro-phenyl)-amide The title compound was produced in analogy with examples 1/2G from (7R,9aS)-7-[2-((S)-4-hydroxy-6-aza-spiro[2.5]oct-6-yl)-ethyl]-5-oxo-hexahydro-pyrrolo[1,2-a]

[1,4]diazepine-2-carboxylic acid benzyl ester and 3,4-dichlorophenyl isocyanate. White solid, MS: 495.3 (M+H)+.

Example 50

(4S,7S,9aR)—N-(3,4-Dichlorophenyl)-4-(2-((S)-4-hydroxy-6-azaspiro[2.5]octan-6-yl)-2-oxoethyl)-7-methyl-6-oxohexahydropyrazino[2,1-c][1,4]oxazine-8(1H)-carboxamide

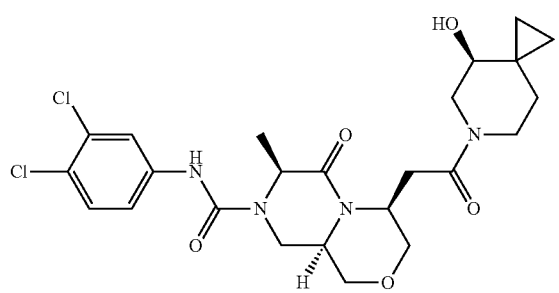 [SMILES: C[C@H]1C(=O)N2[C@@H](CC(=O)N3CCC4(CC4)[C@H](O)C3)COC[C@H]2CN1C(=O)Nc1ccc(Cl)c(Cl)c1]

A) (4S,7S,9aR)-4-Carboxymethyl-7-methyl-6-oxo-hexahydro-pyrazino[2,1-c][1,4]oxazine-8-carboxylic acid benzyl ester The title compound was produced in analogy with example 42A from (4S,7S,9aR)-4-allyl-7-methyl-6-oxo-hexahydro-pyrazino[2,1-c][1,4]oxazine-8-carboxylic acid benzyl ester (example 31E). Dark brown oil, MS: 361.2 (M−H)−.

B) (4S,7S,9aR)-4-[2-((S)-4-Hydroxy-6-aza-spiro[2.5]oct-6-yl)-2-oxo-ethyl]-7-methyl-6-oxo-hexahydro-pyrazino[2,1-c][1,4]oxazine-8-carboxylic acid benzyl ester The title compound was produced in analogy with example 29D from (4S,7S,9aR)-4-carboxymethyl-7-methyl-6-oxo-hexahydro-pyrazino[2,1-c][1,4]oxazine-8-carboxylic acid benzyl ester and (S)-6-aza-spiro[2.5]octan-4-ol hydrochloride. Light yellow oil, MS: 472.2 (M+H)+.

C) (4S,7S,9aR)—N-(3,4-Dichlorophenyl)-4-(2-((S)-4-hydroxy-6-azaspiro[2.5]oct-6-yl)-2-oxoethyl)-7-methyl-6-oxohexahydropyrazino[2,1-c][1,4]oxazine-8(1H)-carboxamide The title compound was produced in analogy with examples 1/2G from (4S,7S,9aR)-4-[2-((S)-4-hydroxy-6-aza-spiro[2.5]oct-6-yl)-2-oxo-ethyl]-7-methyl-6-oxo-hexahydro-pyrazino[2,1-c][1,4]oxazine-8-carboxylic acid benzyl ester and 3,4-dichlorophenyl isocyanate. White foam, MS: 525.2 (M+H)+.

Example 51

(4S,7S,9aR)-4-[3-((S)-4-Hydroxy-6-aza-spiro[2.5]oct-6-yl)-3-oxo-propyl]-7-methyl-6-oxo-hexahydro-pyrazino[2,1-c][1,4]oxazine-8-carboxylic acid (3,4-dichloro-phenyl)-amide

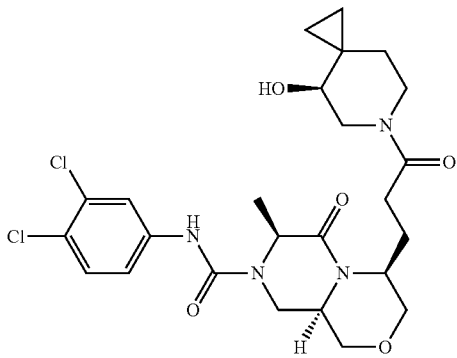 [SMILES: C[C@H]1C(=O)N2[C@@H](CCC(=O)N3CCC4(CC4)[C@H](O)C3)COC[C@H]2CN1C(=O)Nc1ccc(Cl)c(Cl)c1]

A) (3S,5R)-3-Allyl-5-{[benzyloxycarbonyl-((S)-1-tert-butoxycarbonyl-ethyl)-amino]-methyl}-morpholine-4-carboxylic acid tert-butyl ester The title compound was produced in analogy with example 31D from (3S,5S)-3-allyl-5-formyl-morpholine-4-carboxylic acid tert-butyl ester (example 31C) by reductive amination with L-alanine tert-butyl ester hydrochloride, followed by derivatisation of the resultant secondary amine, (3S,5R)-3-allyl-5-[((S)-1-tert-butoxycarbonyl-ethylamino)-methyl]-morpholine-4-carboxylic acid tert-butyl ester with benzyl chloroformate. Light yellow oil, MS: 519.4 (M+H)+.

B) (3R,5S)-3-{[Benzyloxycarbonyl-((S)-1-tert-butoxycarbonyl-ethyl)-amino]-methyl}-5-(3-hydroxy-propyl)-morpholine-4-carboxylic acid tert-butyl ester To a solution of (3S,5R)-3-allyl-5-{[benzyloxycarbonyl-((S)-1-tert-butoxycarbonyl-ethyl)-amino]-methyl}-morpholine-4-carboxylic acid tert-butyl ester (4.50 g, 8.68 mmol) in tetrahydrofuran (90 mL) was added 9-borabicyclo[3.3.1]nonane solution (0.5 M in tetrahydrofuran, 36.4 mL, 18.2 mmol) at 0° C., then after 2 1/2 h another portion of 9-borabicyclo[3.3.1]nonane solution (0.5 M in tetrahydrofuran, 20.8 mL, 10.4 mmol) was added. The reaction mixture was stirred for another 45 min at 0° C., then methanol (80 mL), water (115 mL) and sodium perborate tetrahydrate (37.3 g, 242 mmol) were added. After 90 min the ice bath was removed, then after stirring for 16 h the reaction mixture was partitioned between ethyl acetate and water. The organic layer was washed with brine, dried over magnesium sulfate, filtered, and evaporated. Chromatography (SiO₂; heptane-ethyl acetate gradient) afforded the title compound (3.76 g, 81%). Colourless gum, MS: 537.5 (M+H)+.

C) (4S,7S,9aR)-4-(3-Hydroxy-propyl)-7-methyl-6-oxo-hexahydro-pyrazino[2,1-c][1,4]oxazine-8-carboxylic acid benzyl ester The title compound was produced in analogy with example 48C from (3R,5S)-3-{[benzyloxycarbonyl-((S)-1-tert-butoxycarbonyl-ethyl)-amino]-methyl}-5-(3-hydroxy-propyl)-morpholine-4-carboxylic acid tert-butyl ester. Colourless gum, MS: 363.3 (M+H)⁺.

D) (4S,7S,9aR)-4-(2-Carboxy-ethyl)-7-methyl-6-oxo-hexahydro-pyrazino[2,1-c][1,4]oxazine-8-carboxylic acid benzyl ester The title compound was produced in analogy with example 29C from (4S,7S,9aR)-4-(3-hydroxy-propyl)-7-methyl-6-oxo-hexahydro-pyrazino[2,1-c][1,4]oxazine-8-carboxylic acid benzyl ester. Light yellow gum, MS: 377.4 (M+H)⁺.

E) (4S,7S,9aR)-4-[3-((S)-4-Hydroxy-6-aza-spiro[2.5]oct-6-yl)-3-oxo-propyl]-7-methyl-6-oxo-hexahydro-pyrazino[2,1-c][1,4]oxazine-8-carboxylic acid benzyl ester The title compound was produced in analogy with example 29D from (4S,7S,9aR)-4-(2-carboxy-ethyl)-7-methyl-6-oxo-hexahydro-pyrazino[2,1-c][1,4]oxazine-8-carboxylic acid benzyl ester and (S)-6-aza-spiro[2.5]octan-4-ol hydrochloride. Light yellow oil, MS: 486.3 (M+H)⁺.

F) (4S,7S,9aR)-4-[3-((S)-4-Hydroxy-6-aza-spiro[2.5]oct-6-yl)-3-oxo-propyl]-7-methyl-6-oxo-hexahydro-pyrazino[2,1-c][1,4]oxazine-8-carboxylic acid (3,4-dichloro-phenyl)-amide The title compound was produced in analogy with examples 1/2G from (4S,7S,9aR)-4-[3-((S)-4-hydroxy-6-aza-spiro[2.5]oct-6-yl)-3-oxo-propyl]-7-methyl-6-oxo-hexahydro-pyrazino[2,1-c][1,4]oxazine-8-carboxylic acid benzyl ester and 3,4-dichlorophenyl isocyanate. Light yellow gum, MS: 539.3 (M+H)⁺.

Example 52

(4S,7S,9aR)—N-(3-chloro-4-(trifluoromethyl)phenyl)-4-(3-((S)-4-hydroxy-6-azaspiro[2.5]octan-6-yl)-3-oxopropyl)-7-methyl-6-oxohexahydropyrazino[2,1-c][1,4]oxazine-8(1H)-carboxamide

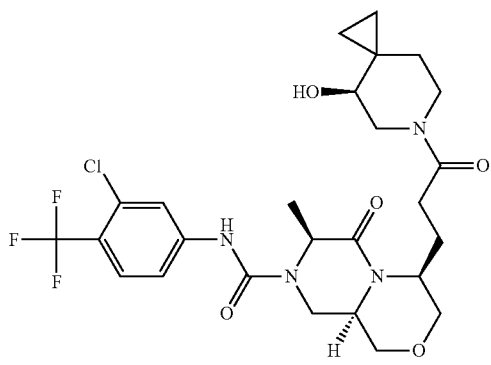 [SMILES: C[C@H]1C(=O)N2[C@@H](CCC(=O)N3CCC4(CC4)[C@H](O)C3)COC[C@H]2CN1C(=O)Nc1ccc(C(F)(F)F)c(Cl)c1]

The title compound was produced in analogy with examples 1/2G from (4S,7S,9aR)-4-[3-((S)-4-hydroxy-6-aza-spiro[2.5]oct-6-yl)-3-oxo-propyl]-7-methyl-6-oxo-hexahydro-pyrazino[2,1-c][1,4]oxazine-8-carboxylic acid benzyl ester (example 51E) and 3-chloro-4-(trifluoromethyl) phenyl isocyanate. White foam, MS: 573.2 (M+H)⁺.

Example 53

(4S,7S,9aR)—N-(3,4-dichlorophenyl)-4-(2-(4,4-difluoro-6-azaspiro[2.5]octan-6-yl)ethyl)-7-methyl-6-oxohexahydropyrazino[2,1-c][1,4]oxazine-8(1H)-carboxamide

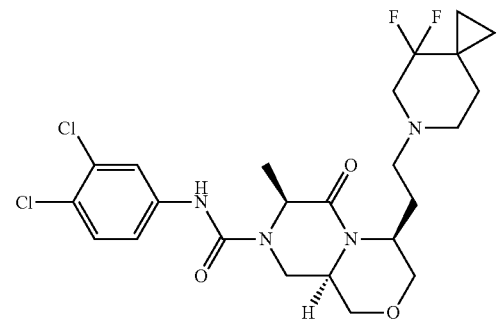 [SMILES: C[C@H]1C(=O)N2[C@@H](CCN3CCC4(CC4)C(F)(F)C3)COC[C@H]2CN1C(=O)Nc1ccc(Cl)c(Cl)c1]

A) (4S,7S,9aR)-Benzyl 4-(2-(4,4-difluoro-6-azaspiro[2.5]octan-6-yl)ethyl)-7-methyl-6-oxohexahydropyrazino[2,1-c][1,4]oxazine-8(1H)-carboxylate The title compound was produced in analogy with examples 33/34D from (4S,7S,9aR)-4-allyl-7-methyl-6-oxo-hexahydro-pyrazino[2,1-c][1,4]oxazine-8-carboxylic acid benzyl ester (example 31E) and 4,4-difluoro-6-azaspiro[2.5] octane hydrochloride (intermediate 4). Brown gum, MS: 478.2 (M+H)⁺.

B) (4S,7S,9aR)—N-(3,4-dichlorophenyl)-4-(2-(4,4-difluoro-6-azaspiro[2.5]octan-6-yl)ethyl)-7-methyl-6-oxohexahydropyrazino[2,1-c][1,4]oxazine-8(1H)-carboxamide The title compound was produced in analogy with examples 1/2G from (4S,7S,9aR)-benzyl 4-(2-(4,4-difluoro-6-azaspiro[2.5]octan-6-yl)ethyl)-7-methyl-6-oxohexahydropyrazino[2,1-c][1,4]oxazine-8(1H)-carboxylate and 3,4-dichlorophenyl isocyanate. White foam, MS:531.1 (M+H)+.

Example 54

(4S,7S,9aR)—N-(3-chlorophenyl)-4-(2-(4,4-difluoro-6-azaspiro[2.5]octan-6-yl)ethyl)-7-methyl-6-oxohexahydropyrazino[2,1-c][1,4]oxazine-8(1H)-carboxamide

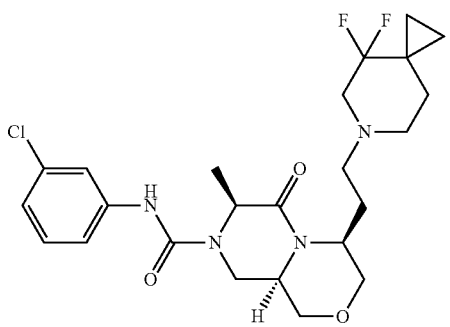 [SMILES: C[C@H]1C(=O)N2[C@@H](CCN3CCC4(CC4)C(F)(F)C3)COC[C@H]2CN1C(=O)Nc1cccc(Cl)c1]

The title compound was produced in analogy with examples 1/2G from (4S,7S,9aR)-benzyl 4-(2-(4,4-difluoro-6-azaspiro[2.5]octan-6-yl)ethyl)-7-methyl-6-oxohexahydropyrazino[2,1-c][1,4]oxazine-8(1H)-carboxylate (example 53A) and 3-chlorophenyl isocyanate. White foam, MS:497.3 (M+H)+.

Example 55

(4S,7S,9aR)—N-(3-chloro-4-(trifluoromethyl)phenyl)-4-(2-(4,4-difluoro-6-azaspiro[2.5]octan-6-yl)ethyl)-7-methyl-6-oxohexahydropyrazino[2,1-c][1,4]oxazine-8(1H)-carboxamide

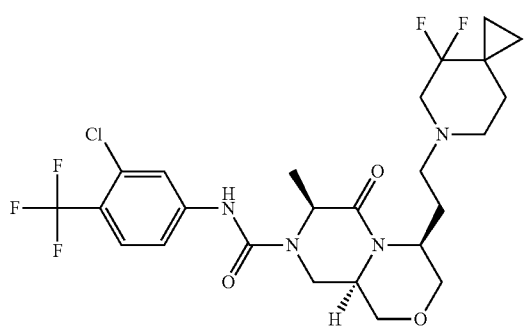 [SMILES: C[C@H]1C(=O)N2[C@@H](CCN3CCC4(CC4)C(F)(F)C3)COC[C@H]2CN1C(=O)Nc1ccc(C(F)(F)F)c(Cl)c1]

The title compound was produced in analogy with examples 1/2G from (4S,7S,9aR)-benzyl 4-(2-(4,4-difluoro-6-azaspiro[2.5]octan-6-yl)ethyl)-7-methyl-6-oxohexahydropyrazino[2,1-c][1,4]oxazine-8(1H)-carboxylate (example 53A) and 3-chloro-4-(trifluoromethyl)phenyl isocyanate. White solid, MS:565.2 (M+H)+.

Example 56

(4S,7S,9aR)—N-(3,4-dichlorophenyl)-4-(2-(4,4-difluoropiperidin-1-yl)ethyl)-7-methyl-6-oxohexahydropyrazino[2,1-c][1,4]oxazine-8(1H)-carboxamide

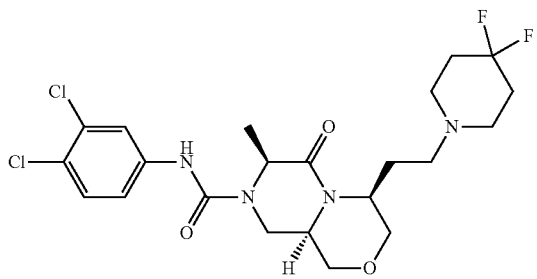 [SMILES: C[C@H]1C(=O)N2[C@@H](CCN3CCC(F)(F)CC3)COC[C@H]2CN1C(=O)Nc1ccc(Cl)c(Cl)c1]

A) (4S,7S,9aR)-Benzyl 4-(2-(4,4-difluoropiperidin-1-yl)ethyl)-7-methyl-6-oxohexahydropyrazino[2,1-c][1,4]oxazine-8(1H)-carboxylate The title compound was produced in analogy with examples 33/34D from (4S,7S,9aR)-4-allyl-7-methyl-6-oxohexahydro-pyrazino[2,1-c][1,4]oxazine-8-carboxylic acid benzyl ester (example 31E) and 4,4-difluoropiperidine hydrochloride. Black gum, MS:452.2 (M+H)+.

B) (4S,7S,9aR)—N-(3,4-dichlorophenyl)-4-(2-(4,4-difluoropiperidin-1-yl)ethyl)-7-methyl-6-oxohexahydropyrazino[2,1-c][1,4]oxazine-8(1H)-carboxamide The title compound was produced in analogy with examples 1/2G from (4S,7S,9aR)-benzyl 4-(2-(4,4-difluoropiperidin-1-yl)ethyl)-7-methyl-6-oxohexahydropyrazino[2,1-c][1,4]oxazine-8(1H)-carboxylate and 3,4-dichlorphenyl isocyanate. White foam, MS:505.2 (M+H)+.

Example 57

(4S,7S,9aR)—N-(3-chloro-4-(trifluoromethyl)phenyl)-4-(2-(4,4-difluoropiperidin-1-yl)ethyl)-7-methyl-6-oxohexahydropyrazino[2,1-c][1,4]oxazine-8(1H)-carboxamide

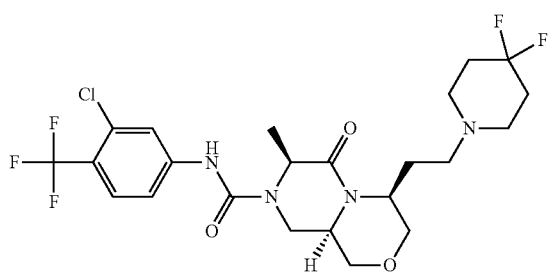 [SMILES: C[C@H]1C(=O)N2[C@@H](CCN3CCC(F)(F)CC3)COC[C@H]2CN1C(=O)Nc1ccc(C(F)(F)F)c(Cl)c1]

The title compound was produced in analogy with examples 1/2G from (4S,7S,9aR)-benzyl 4-(2-(4,4-difluoropiperidin-1-yl)ethyl)-7-methyl-6-oxohexahydropyrazino

[2,1-c][1,4]oxazine-8(1H)-carboxylate (example 56A) and 3-chloro-4-(trifluoromethyl)phenyl isocyanate. White foam, MS:539.2 (M+H)+.

Example 58

(4S,7S,9aR)-4-[2-(1,1-Dioxo-thiomorpholin-4-yl)-ethyl]-7-methyl-6-oxo-hexahydro-pyrazino[2,1-c][1,4]oxazine-8-carboxylic acid (3,4-dichloro-phenyl)-amide

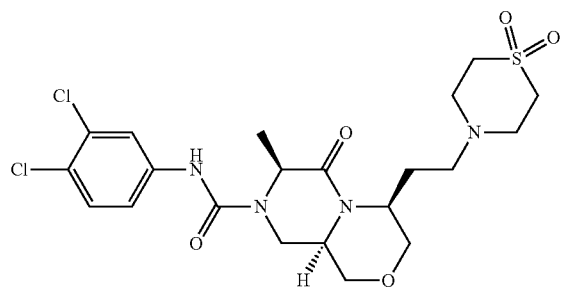 [SMILES: C[C@H]1C(=O)N2[C@@H](CCN3CCS(=O)(=O)CC3)COC[C@H]2CN1C(=O)Nc1ccc(Cl)c(Cl)c1]

A) (4S,7S,9aR)-Benzyl 4-(2-(1,1-dioxo-thiomorpholin-4-yl)ethyl)-7-methyl-6-oxohexahydropyrazino[2,1-c][1,4]oxazine-8(1H)-carboxylate The title compound was produced in analogy with examples 33/34D from (4S,7S,9aR)-4-allyl-7-methyl-6-oxo-hexahydro-pyrazino[2,1-c][1,4]oxazine-8-carboxylic acid benzyl ester (example 31E) and thiomorpholine 1,1-dioxide. Black gum, MS:452.2 (M+H)+.

B) (4S,7S,9aR)-4-[2-(1,1-Dioxo-thiomorpholin-4-yl)-ethyl]-7-methyl-6-oxo-hexahydro-pyrazino[2,1-c][1,4]oxazine-8-carboxylic acid (3,4-dichloro-phenyl)-amide The title compound was produced in analogy with examples 1/2G from (4S,7S,9aR)-benzyl 4-(2-(1,1-dioxo-thiomorpholin-4-yl)ethyl)-7-methyl-6-oxohexahydropyrazino[2,1-c][1,4]oxazine-8(1H)-carboxylate and 3,4-dichlorphenyl isocyanate. White foam, MS:519.1 (M+H)+.

Example 59

(4S,7S,9aR)-4-[2-(1,1-Dioxo-6-thiomorpholin-4-yl)-ethyl]-7-methyl-6-oxo-hexahydro-pyrazino[2,1-c][1,4]oxazine-8-carboxylic acid (3-chloro-4-trifluoromethyl-phenyl)-amide

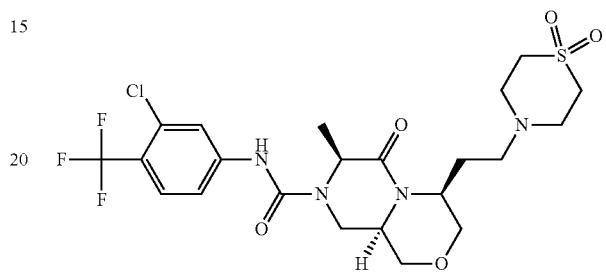

B) (4S,7S,9aR)-4-[2-(1,1-Dioxo-thiomorpholin-4-yl)-ethyl]-7-methyl-6-oxo-hexahydro-pyrazino[2,1-c][1,4]oxazine-8-carboxylic acid (3,4-dichloro-phenyl)-amide The title compound was produced in analogy with examples 1/2G from (4S,7S,9aR)-benzyl 4-(2-(1,1-dioxo-thiomorpholin-4-yl)ethyl)-7-methyl-6-oxohexahydropyrazino[2,1-c][1,4]oxazine-8(1H)-carboxylate (example 58A) and 3-chloro-4-(trifluoromethyl)phenyl isocyanate. White foam, MS:553.2 (M+H)+.

Example 60

(4S,7S,9aR)—N-(3,4-dichlorophenyl)-4-(3-(4,4-difluoro-6-azaspiro[2.5]octan-6-yl)propyl)-7-methyl-6-oxohexahydropyrazino[2,1-c][1,4]oxazine-8(1H)-carboxamide

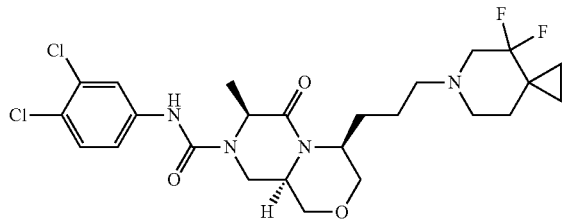 [SMILES: C[C@H]1C(=O)N2[C@@H](CCCN3CCC4(CC4)C(F)(F)C3)COC[C@H]2CN1C(=O)Nc1ccc(Cl)c(Cl)c1]

The title compound was produced in analogy with examples 1/2G from (4S,7S,9aR)-benzyl 4-(3-(4,4-difluoro-6-azaspiro[2.5]octan-6-yl)propyl)-7-methyl-6-oxohexahydropyrazino[2,1-c][1,4]oxazine-8(1H)-carboxylate (example 60A) and 3-chloro-4-(trifluoromethyl)phenyl isocyanate. White foam, MS:579.2 (M+H)+.

Example 61

(4S,7S,9aR)—N-(3-chloro-4-(trifluoromethyl)phenyl)-4-(3-(4,4-difluoro-6-azaspiro[2.5]octan-6-yl)propyl)-7-methyl-6-oxohexahydropyrazino[2,1-c][1,4]oxazine-8(1H)-carboxamide

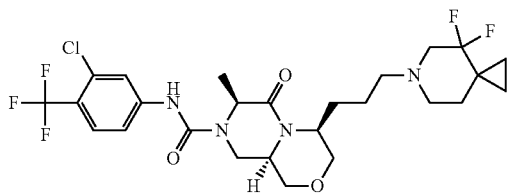 [SMILES: C[C@H]1C(=O)N2[C@@H](CCCN3CCC4(CC4)C(F)(F)C3)COC[C@H]2CN1C(=O)Nc1ccc(C(F)(F)F)c(Cl)c1]

The title compound was produced in analogy with examples 1/2G from (4S,7S,9aR)-benzyl 4-(3-(4,4-difluoro-6-azaspiro[2.5]octan-6-yl)propyl)-7-methyl-6-oxohexahydropyrazino[2,1-c][1,4]oxazine-8(1H)-carboxylate (example 60A) and 3-chloro-4-(trifluoromethyl)phenyl isocyanate. White foam, MS:579.2 (M+H)+.

Example 62

(3S,6R,9aS)-2-[(E)-3-(3-Chloro-4-fluoro-phenyl)-acryloyl]-6-[3-((S)-4-hydroxy-6-aza-spiro[2.5]oct-6-yl)-3-oxo-propyl]-3-methyl-octahydro-pyrido[1,2-a]pyrazin-4-one

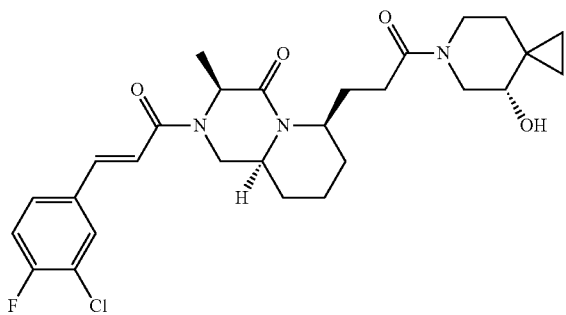 [SMILES: C[C@H]1C(=O)N2[C@@H](CCC(=O)N3CCC4(CC4)[C@H](O)C3)CCC[C@H]2CN1C(=O)/C=C/c1ccc(F)c(Cl)c1]

A) (2S,6R)-6-Allyl-piperidine-1,2-dicarboxylic acid 1-tert-butyl ester-2-methyl ester The title compound was produced in analogy with example 38A from 1-(tert-butoxycarbonyl)-R-6-oxopipecolic acid methyl ester (prepared in analogy to the procedure described for the (S)-enantiomer (J. Org. Chem. 1996, 61, 8496). Light yellow liquid, MS: 284.2 (M+H)+.

B) (2R,6S)-2-Allyl-6-hydroxymethyl-piperidine-1-carboxylic acid tert-butyl ester The title compound was produced in analogy with example 31B from (2S,6R)-6-allyl-piperidine-1,2-dicarboxylic acid 1-tert-butyl ester 2-methyl ester. Colourless oil, MS: 256.3 (M+H)+.

C) (2R,6S)-2-Allyl-6-formyl-piperidine-1-carboxylic acid tert-butyl ester

The title compound was produced in analogy with example 31C from (2R,6S)-2-allyl-6-hydroxymethyl-piperidine-1-carboxylic acid tert-butyl ester. Colourless oil, MS: 254.3 (M+H)+.

D) (2R,6S)-2-Allyl-6-{[benzyloxycarbonyl-((S)-1-tert-butoxycarbonyl-ethyl)-amino]-methyl}-piperidine-1-carboxylic acid tert-butyl ester The title compound was produced in analogy with example 31D from (2R,6S)-2-allyl-6-formyl-piperidine-1-carboxylic acid tert-butyl ester by reductive amination reaction with L-alanine tert-butyl ester hydrochloride, followed by derivatisation of the resultant secondary amine, (R)-2-allyl-6-[((S)-1-tert-butoxycarbonyl-ethylamino)-methyl]-piperidine-1-carboxylic acid tert-butyl ester with benzyl chloroformate. Light yellow oil, MS: 517.4 (M+H)+.

E) (2S,6R)-2-{[Benzyloxycarbonyl-((S)-1-tert-butoxycarbonyl-ethyl)-amino]-methyl}-6-(3-hydroxy-propyl)-piperidine-1-carboxylic acid tert-butyl ester The title compound was produced in analogy with example 51B from (2R,6S)-2-allyl-6-{[benzyloxycarbonyl-((S)-1-tert-butoxycarbonyl-ethyl)-amino]-methyl}-piperidine-1-carboxylic acid tert-butyl ester. Colourless gum, MS: 535.4 (M+H)+.

F) (3S,6R,9aS)-6-(3-Hydroxy-propyl)-3-methyl-4-oxo-octahydro-pyrido[1,2-a]pyrazine-2-carboxylic acid benzyl ester The title compound was produced in analogy with example 48C from (2S,6R)-2-{[benzyloxycarbonyl-((S)-1-tert-butoxycarbonyl-ethyl)-amino]-methyl}-6-(3-hydroxy-propyl)-piperidine-1-carboxylic acid tert-butyl ester. Colourless gum, MS: 361.4 (M+H)+.

G) (3S,6R,9aS)-6-(2-Carboxy-ethyl)-3-methyl-4-oxo-octahydro-pyrido[1,2-a]pyrazine-2-carboxylic acid benzyl ester The title compound was produced in analogy with example 29C from (3S,6R,9aS)-6-(3-hydroxy-propyl)-3-methyl-4-oxo-octahydro-pyrido[1,2-a]pyrazine-2-carboxylic acid benzyl ester. Colourless gum, MS: 373.4 (M–H)−.

H) (3S,6R,9aS)-6-[3-((S)-4-Hydroxy-6-aza-spiro[2.5]oct-6-yl)-3-oxo-propyl]-3-methyl-4-oxo-octahydro-pyrido[1,2-a]pyrazine-2-carboxylic acid benzyl ester The title compound was produced in analogy with example29D from (3S,6R,9aS)-6-(2-carboxy-ethyl)-3-methyl-4-oxo-octahydro-pyrido[1,2-a]pyrazine-2-carboxylic acid benzyl ester and (S)-6-aza-spiro[2.5]octan-4-ol hydrochloride. White foam, MS: 484.5 (M+H)+.

I) (3S,6R,9aS)-6-[3-((S)-4-Hydroxy-6-aza-spiro[2.5]oct-6-yl)-3-oxo-propyl]-3-methyl-octahydro-pyrido[1,2-a]pyrazin-4-one The title compound was produced in analogy with example 12G from (3S,6R,9aS)-6-[3-((S)-4-hydroxy-6-aza-spiro[2.5]

oct-6-yl)-3-oxo-propyl]-3-methyl-4-oxo-octahydro-pyrido[1,2-a]pyrazine-2-carboxylic acid benzyl ester. Light grey foam, MS: 350.4 (M+H)⁺.

J) (3S,6R,9aS)-2-[(E)-3-(3-Chloro-4-fluoro-phenyl)-acryloyl]-6-[3-((S)-4-hydroxy-6-aza-spiro[2.5]oct-6-yl)-3-oxo-propyl]-3-methyl-octahydro-pyrido[1,2-a]pyrazin-4-one The title compound was produced in analogy with example 29D from (3S,6R,9aS)-6-[3-((S)-4-hydroxy-6-aza-spiro[2.5]oct-6-yl)-3-oxo-propyl]-3-methyl-octahydro-pyrido[1,2-a]pyrazin-4-one and 3-chloro-4-fluorocinnamic acid. White foam, MS: 532.2 (M+H)⁺.

Example 63

(3S,6R,9aS)-6-[3-((S)-4-Hydroxy-6-aza-spiro[2.5]oct-6-yl)-3-oxo-propyl]-3-methyl-4-oxo-octahydro-pyrido[1,2-a]pyrazine-2-carboxylic acid (3,4-dichloro-phenyl)-amide

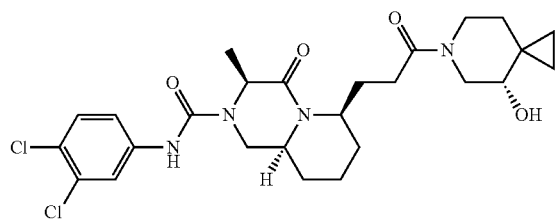 [SMILES: C[C@H]1C(=O)N2[C@@H](CCC(=O)N3CCC4(CC4)[C@H](O)C3)CCC[C@H]2CN1C(=O)Nc1ccc(Cl)c(Cl)c1]

The title compound was produced in analogy with examples 12H from (3S,6R,9aS)-6-[3-((S)-4-hydroxy-6-aza-spiro[2.5]oct-6-yl)-3-oxo-propyl]-3-methyl-octahydro-pyrido[1,2-a]pyrazin-4-one (example 62I) and 3,4-dichlorophenyl isocyanate. White foam, MS: 537.3 (M+H)⁺.

Example 64

(3S,6R,9aS)-6-[3-((S)-4-Hydroxy-6-aza-spiro[2.5]oct-6-yl)-3-oxo-propyl]-3-methyl-4-oxo-octahydro-pyrido[1,2-a]pyrazine-2-carboxylic acid (3-chloro-4-trifluoromethyl-phenyl)-amide

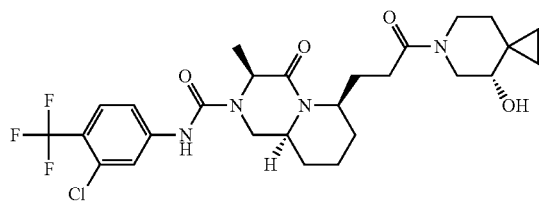 [SMILES: C[C@H]1C(=O)N2[C@@H](CCC(=O)N3CCC4(CC4)[C@H](O)C3)CCC[C@H]2CN1C(=O)Nc1ccc(C(F)(F)F)c(Cl)c1]

The title compound was produced in analogy with examples 12H from (3S,6R,9aS)-6-[3-((S)-4-hydroxy-6-aza-spiro[2.5]oct-6-yl)-3-oxo-propyl]-3-methyl-octahydro-pyrido[1,2-a]pyrazin-4-one (example 62I) and 3-chloro-4-(trifluoromethyl)phenyl isocyanate. White foam, MS: 571.2 (M+H)⁺.

Example 65

(3S,6R,9aS)-6-[2-((S)-4-Hydroxy-6-aza-spiro[2.5]oct-6-yl)-ethyl]-3-methyl-4-oxo-octahydro-pyrido[1,2-a]pyrazine-2-carboxylic acid (3,4-dichloro-phenyl)-amide

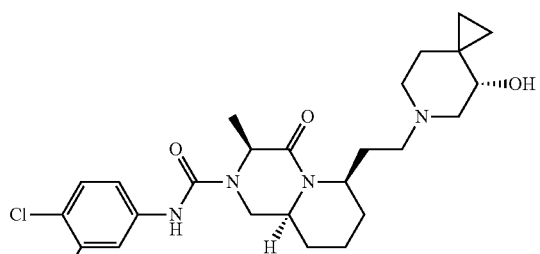

A) (3S,6R,9aS)-6-Allyl-3-methyl-4-oxo-octahydro-pyrido[1,2-a]pyrazine-2-carboxylic acid benzyl ester The title compound was produced in analogy with example 48C from (2R,6S)-2-allyl-6-{[benzyloxycarbonyl-((S)-1-tert-butoxycarbonyl-ethyl)-amino]-methyl}-piperidine-1-carboxylic acid tert-butyl ester (example 62D). Colourless gum, MS: 343.2 (M+H)⁺.

B) (3S,6R,9aS)-6-[2-((S)-4-Hydroxy-6-aza-spiro[2.5]oct-6-yl)-ethyl]-3-methyl-4-oxo-octahydro-pyrido[1,2-a]pyrazine-2-carboxylic acid benzyl ester The title compound was produced in analogy with examples 33/34D from (3S,6R,9aS)-6-allyl-3-methyl-4-oxo-octahydro-pyrido[1,2-a]pyrazine-2-carboxylic acid benzyl ester and (S)-6-aza-spiro[2.5]octan-4-ol hydrochloride. White foam, MS: 456.5 (M+H)⁺.

C) (3S,6R,9aS)-6-[2-((S)-4-Hydroxy-6-aza-spiro[2.5]oct-6-yl)-ethyl]-3-methyl-4-oxo-octahydro-pyrido[1,2-a]pyrazine-2-carboxylic acid (3,4-dichloro-phenyl)-amide The title compound was produced in analogy with examples 1/2G from (3S,6R,9aS)-6-[2-((S)-4-hydroxy-6-aza-spiro[2.5]oct-6-yl)-ethyl]-3-methyl-4-oxo-octahydropyrido[1,2-a]pyrazine-2-carboxylic acid benzyl ester and 3,4-dichlorophenyl isocyanate. White foam, MS: 509.4 (M+H)$^+$.

Example 66

(3S,6R,9aS)-6-[2-((S)-4-Hydroxy-6-aza-spiro[2.5]oct-6-yl)-ethyl]-3-methyl-4-oxo-octahydro-pyrido[1,2-a]pyrazine-2-carboxylic acid (3-chloro-phenyl)-amide

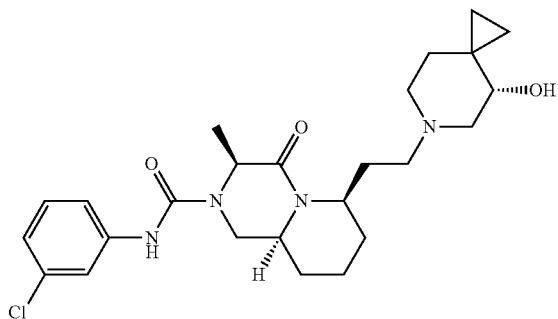 [SMILES: C[C@H]1C(=O)N2[C@@H](CCN3CCC4(CC4)[C@H](O)C3)CCC[C@H]2CN1C(=O)Nc1cccc(Cl)c1]

The title compound was produced in analogy with examples 1/2G from (3S,6R,9aS)-6-[2-((S)-4-hydroxy-6-aza-spiro[2.5]oct-6-yl)-ethyl]-3-methyl-4-oxo-octahydro-pyrido[1,2-a]pyrazine-2-carboxylic acid benzyl ester (example 65B) and 3-chlorophenyl isocyanate. Light yellow foam, MS: 475.3 (M+H)$^+$.

Example 67

(3S,6R,9aS)-6-[2-((S)-4-Hydroxy-6-aza-spiro[2.5]oct-6-yl)-ethyl]-3-methyl-4-oxo-octahydro-pyrido[1,2-a]pyrazine-2-carboxylic acid (3-fluoro-phenyl)-amide

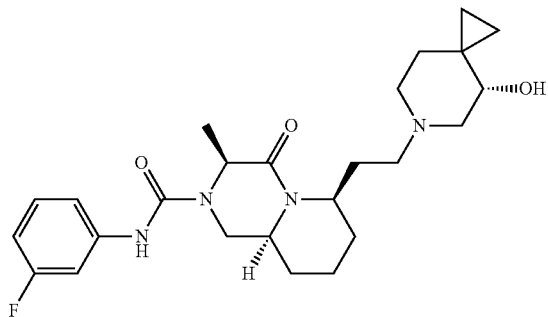 [SMILES: C[C@H]1C(=O)N2[C@@H](CCN3CCC4(CC4)[C@H](O)C3)CCC[C@H]2CN1C(=O)Nc1cccc(F)c1]

The title compound was produced in analogy with examples 1/2G from (3S,6R,9aS)-6-[2-((S)-4-hydroxy-6-aza-spiro[2.5 ]oct-6-yl)-ethyl]-3-methyl-4-oxo-octahydro-pyrido[1,2-a]pyrazine-2-carboxylic acid benzyl ester (example 65B) and 3-fluorophenyl isocyanate. Light yellow foam, MS: 459.4 (M+H)$^+$.

Example 68

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Polyvinylpyrrolidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magesiumstearate and compressed to yield kernels of 120 or 350 mg respectively. The kernels are lacquered with an aqueous solution/suspension of the above mentioned film coat.

Example 69

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 70

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | Ad 1.0 ml |

The active ingredient is dissolved in a mixture of polyethylene glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example 71

Soft gelatin capsules containing the following ingredients can be manufactured in a conventional manner:

| Capsule contents | |
| --- | --- |
| Compound of formula (I) | 5.0 mg |
| Yellow wax | 8.0 mg |
| Hydrogenated soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example 72

Sachets containing the following ingredients can be manufactured in a conventional manner:

| | |
| --- | --- |
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesiumstearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesiumstearate and the flavouring additives and filled into sachets.

Example 73

The Following Describes Receptor Binding Assays

Binding assays were done with membranes from CHOK1-CCR2B-A5 cells (Euroscreen) stably overexpressing the human CCR2B.

Membranes were prepared by homogenizing the cells in 10 mM Tris pH 7.4, 1 mM EDTA, 0.05 mM benzamidine, leupeptin 6 mg/L and separating the debris at 1000 g. The membranes were then isolated at 100000 g in 50 mM Tris pH 7.4, $MgCl_2$ 10 mM, EGTA 1 mM, glycerol 10%, benzamidine 0.05 mM, leupeptine 6 mg/l.

For binding, CCR2 antagonist compounds were added in various concentrations in 50 mM HEPES pH 7.2, 1 mM $CaCl_2$, 5 mM $MgCl_2$, 0.5% BSA, 0.01% $NaN_3$, together with 100 pM $^{125}$I-MCP-1 (PerkinElmer, 2200Ci/mmol) to about 5 fMol CCR2 membranes and incubated for 1 hour at room temperature. For unspecific control 57.7 nM MCP-1 (R&D Systems or prepared at Roche) was added. Membranes were harvested through GF/B (glass fiber filter; PerkinElmer) plates, equilibrated with 0.3% polyethylenimine, 0.2% BSA, air dried and binding was determined by counting in a top-counter (NXT Packard). Specific binding was defined as total binding minus nonspecific binding and typically represents about 90-95% of the total binding. Antagonist activity is indicated as inhibitor concentration required for 50% inhibition ($IC_{50}$) of specific binding.

Example 74

The Following Describes a Calcium Mobilization Assay

CHOK1-CCR2B-A5 cells (from Euroscreen) stably overexpressing the human chemokine receptor 2 isoform B were cultured in Nutrient Hams F12 medium supplemented with 5% FBS, 100 U/ml penicillin, 100 µg/ml streptomycin, 400 µg/ml G418 and 5 µg/ml puromycin.

For the assay cells were grown overnight in 384-well black clear flat bottom polystyrene plates (Costar) at 37° C. at 5% $CO_2$. After washing with DMEM, 20 mM Hepes, 2.5 mM probenecid, 0.1% BSA (DMEM assay buffer) cells were loaded with 4 µM Fluo-4 in the same DMEM assay buffer for 2 hours at 30° C. Excess dye was removed and cells were washed with DMEM assay buffer. 384-well compound plates were prepared with DMEM assay buffer/0.5% DMSO with or without various concentrations of test compounds. Usually compounds were tested for agonist and antagonist activity.

Test compounds were added to the assay plate and agonist activity was monitored as fluorescence for 80 seconds with a FLIPR (488 nm excitation; 510-570 nm emission; Molecular Devices). After 20-30 min. of incubation at 30° C., 20 nM MCP-1 (R&D; Roche) was added and fluorescence was monitored again for 80 seconds. Increases in intracellular calcium are reported as maximum fluorescence after agonist exposure minus basal fluorescence before exposure. Antagonist activity is indicated as inhibitor concentration required for 50% inhibition of specific calcium increases.

The compounds I of the present invention exhibit $IC_{50}$ values in the Ca mobilisation assay of 1 nM to 10 µM, preferably 1 nM to 1.5 µM for CCR2. The following table shows measured values for some selected compounds of the present invention.

| Example | IC50 (µM) |
| --- | --- |
| 1 | 0.0058 |
| 2 | 0.0022 |
| 3 | 0.0604 |
| 4 | 0.0160 |
| 5 | 0.0679 |
| 6 | 0.0720 |
| 7 | 0.0250 |
| 8 | 0.1463 |
| 9 | 0.0689 |
| 12 | 0.0120 |
| 13 | 0.0127 |
| 14 | 0.0111 |
| 15 | 0.0328 |
| 16 | 0.0074 |
| 17 | 0.0029 |
| 18 | 0.0102 |
| 19 | 0.0334 |
| 20 | 0.1766 |
| 21 | 0.0038 |
| 22 | 0.0274 |
| 23 | 0.0144 |
| 24 | 0.0055 |
| 25 | 0.0200 |
| 26 | 0.0618 |
| 27 | 0.0494 |
| 28 | 0.0037 |
| 29 | 0.7743 |
| 30 | 0.0015 |
| 31 | 0.0019 |

-continued

| Example | IC50 (μM) |
|---|---|
| 32 | 0.0021 |
| 33 | 0.0027 |
| 35 | 0.0057 |
| 36 | 0.0093 |
| 37 | 0.3604 |
| 38 | 0.0088 |
| 39 | 0.1354 |
| 40 | 0.3404 |
| 41 | 0.0033 |
| 42 | 0.0404 |
| 43 | 0.0205 |
| 44 | 0.4732 |
| 45 | 0.1996 |
| 46 | 0.0264 |
| 47 | 0.0674 |
| 49 | 0.1443 |
| 51 | 0.0869 |
| 52 | 0.0147 |
| 53 | 0.0167 |
| 54 | 0.1698 |
| 55 | 0.0343 |
| 56 | 0.0810 |
| 57 | 0.1194 |
| 58 | 0.4139 |
| 59 | 0.1893 |
| 60 | 0.0482 |
| 61 | 0.0341 |
| 62 | 0.2205 |
| 63 | 0.0108 |
| 64 | 0.0143 |
| 65 | 0.0022 |
| 66 | 0.0030 |
| 67 | 0.0079 |

The invention claimed is:

1. A compound according to formula (I)

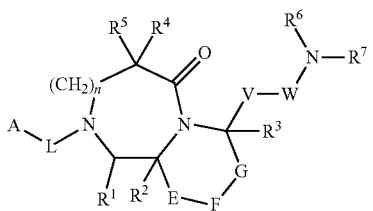

wherein
A is selected from the group consisting of: aryl, heteroaryl, arylmethyl and heteroarylmethyl, wherein the said aryl, heteroaryl and the aryl of arylmethyl are optionally substituted by one to three substituents independently selected from the group consisting of halogen, aryl, heteroaryl, $C_{1-6}$ alkyl, halo$C_{1-6}$ alkyl, $C_{1-6}$ alkoxy and halo $C_{1-6}$ alkoxy;
E is $CH_2$ or O;
F is selected from the group consisting of: $CH_2$, O, $N(R^8)$, S, SO and $SO_2$;
G is selected from the group consisting of: a single bond, $CH_2$, and $CH_2CH_2$, with the proviso that, when E is O, then F is not O, S, SO or $SO_2$;
L is selected from the group consisting of: a bond, NH—C (=O), NH—C(=S), and CH=CH—C(=O);
$R^1$, $R^2$ and $R^3$ are independently of each other selected from the group consisting of:
hydrogen,
$C_{1-6}$ alkyl, which is optionally substituted by one to three substituents independently selected from the group consisting of hydroxy, $C_{1-6}$ alkoxy, carboxyl, carbamoyl, mono or di-$C_{1-6}$ alkyl substituted aminocarbonyl and $C_{1-6}$ alkoxycarbonyl, aryl and heteroaryl, wherein said heteroaryl and aryl are optionally substituted by one to three substituents independently selected from the group consisting of halogen, $C_{1-6}$ alkyl, halo $C_{1-6}$ alkyl, $C_{1-6}$ alkoxy and halo $C_{1-6}$ alkoxy,
$C_{3-7}$ cycloalkyl, and
aryl;
$R^4$ and $R^5$ are independently of each other selected from the group consisting of:
hydrogen,
$C_{1-6}$ alkyl, which is optionally substituted by one to three substituents independently selected from the group consisting of amino, hydroxy, carboxyl, carbamoyl, mono or di-$C_{1-6}$ alkyl substituted aminocarbonyl and $C_{1-6}$ alkoxycarbonyl, and
$C_{3-7}$ cycloalkyl, which is optionally substituted by one to three substituents independently selected from the group consisting of amino, hydroxy, carboxyl, carbamoyl, mono or di-$C_{1-6}$ alkyl substituted aminocarbonyl and $C_{1-6}$ alkoxycarbonyl; or
$R^4$ and $R^5$, together with the carbon atom to which they are attached, form $C_{3-7}$ cycloalkyl or heterocyclyl which is optionally substituted by one to three substituents independently selected from the group consisting of $C_{1-4}$ alkyl, halo $C_{1-4}$ alkyl and halogen;
$R^6$ and $R^7$ together with the nitrogen atom to which they are attached form 6-aza-spiro[2,5]oct-6-yl, 5-azaspiro[2.5] oct-5-yl, 7-aza-spiro[3.5]non-7-yl, 8-aza-spiro[4.5]dec-8-yl, 1,8-diaza-spiro[4.5]dec-8-yl, 1,3,8-triaza-spiro [4.5]dec-8-yl, 2,8-diaza-spiro[4.5]dec-8-yl, 1-oxa-3,8-diaza-spiro[4.5]dec-8-yl, 1-oxa-8-aza-spiro[4.5]dec-8-yl, 2-oxa-8-aza-spiro[4.5]dec-8-yl, 2-oxa-7-aza-spiro [3.5]non-7-yl, 1-oxa-7-aza-spiro[3.5]non-7-yl, 9-aza-spiro[5.5]undec-9-yl, or 1-oxa-4,9-diaza-spiro[5.5] undec-9-yl wherein the spiro-heterocyclyl ring is optionally substituted by one to three substituents independently selected from the group consisting of hydroxy, oxo, alkoxy, fluoro and $C_{1-6}$ alkyl;
$R^8$ is selected from the group consisting of: hydrogen, $C_{1-6}$ alkyl, $C(=O)R^9$, and $S(O_2)R^9$;
$R^9$ is $C_{1-6}$ alkyl or $C_{3-7}$ cycloalkyl;
V is a $C_{1-4}$ alkylene, wherein each carbon atom is optionally substituted by one or two substituents independently selected from the group consisting of:
hydroxy,
$C_{1-6}$ alkyl,
$C_{1-6}$ alkoxy,
hydroxy-$C_{1-6}$ alkyl,
$C_{1-6}$ alkoxy-$C_{1-6}$ alkyl,
halogen, and
halo $C_{1-6}$ alkyl;
W is selected from the group consisting of: a bond, $CH_2$ and $C(=O)$; and
n is 0 or 1;
or a pharmaceutically acceptable salt thereof.

2. A compound according to claim 1, wherein A is phenyl or naphthyl, wherein said phenyl and said naphthyl are optionally substituted by one to three substituents selected from the group consisting of halogen, halo $C_{1-6}$ alkyl, halo $C_{1-6}$ alkoxy and aryl.

3. A compound according to claim 1, wherein A is phenyl substituted by one or two substituents selected from the group consisting of halogen atoms and trifluoromethyl.

4. A compound according to claim 1, wherein A is phenyl substituted by one or two substituents which are independently selected from the group consisting of chloro, fluoro and trifluoromethyl.

5. A compound according to claim 1, wherein A is selected from the group consisting of: 3-Fluoro-phenyl, 3-chloro-4-trifluoromethyl-phenyl and 3,4-dichlorophenyl.

6. A compound according to claim 1, wherein $R^6$ and $R^7$ together with the nitrogen atom to which they are attached form 6-aza-spiro[2,5]oct-6-yl wherein the spiro-heterocyclyl ring is optionally substituted by one to two substituents independently selected from the group consisting of fluoro, hydroxy and $C_{1-6}$ alkyl.

7. A compound according to claim 1, wherein $R^6$ and $R^7$ together with the nitrogen atom to which they are attached form a (S)-4-hydroxy-6-aza-spiro[2,5]oct-6-yl.

8. A compound according to claim 1, wherein n is 0.

9. A compound according to claim 1, wherein V is $C_{1-2}$ alkylene.

10. A compound according to claim 1, wherein $R^1$, $R^2$, $R^3$, $R^4$ and $R^5$ are independently hydrogen or $C_{1-6}$ alkyl.

11. A compound according to claim 1, wherein one of $R^4$ and $R^5$ is hydrogen or $C_{1-6}$ alkyl and the other is hydrogen, $R^1$ and $R^3$ are hydrogen and $R^2$ is hydrogen or $C_{1-6}$ alkyl.

12. A compound according to claim 1, wherein one of $R^4$ or $R^5$ is methyl and the other is hydrogen, and $R^1$, $R^2$ and $R^3$ are hydrogen.

13. A compound according to claim 1, wherein L is NH—C(=O) or CH=CH—C(=O).

14. A compound according to claim 1, wherein L is NH—C(=O).

15. A compound according to claim 1, wherein E and F are independently O or $CH_2$ with the proviso that, when E is O, then F is not O.

16. A compound according to claim 1, wherein G is a single bond or $CH_2$.

17. A compound according to claim 1, wherein $R^4$ is methyl, $R^1$, $R^2$, $R^3$ and $R^5$ are hydrogen, L is NHC(=O), V is $C_{1-2}$ alkylene and $R^6$ and $R^7$ together with the nitrogen atom to which they are attached form (S)-4-hydroxy-6-aza-spiro [2,5]oct-6-yl.

18. A compound according to claim 1, selected from the group consisting of:
- (3S,6S,8aS)-3-[2-((S)-4-Hydroxy-6-aza-spiro[2.5]oct-6-yl)-ethyl]-6-methyl-5-oxo-hexahydro-oxazolo[3,2-a]pyrazine-7-carboxylic acid (3,4-dichloro-phenyl)-amide,
- (3S,6S,8aR)-3-[2-((S)-4-Hydroxy-6-aza-spiro[2.5]oct-6-yl)-ethyl]-6-methyl-5-oxo-hexahydro-oxazolo[3,2-a]pyrazine-7-carboxylic acid (3,4-dichloro-phenyl)-amide,
- (3S,6S,8aS)-3-[3-((S)-4-Hydroxy-6-aza-spiro[2.5]oct-6-yl)-3-oxo-propyl]-6-methyl-5-oxo-hexahydro-oxazolo[3,2-a]pyrazine-7-carboxylic acid (3-chloro-4-trifluoromethyl-phenyl)-amide,
- (4S,7S)-4-((S)-4-Hydroxy-6-aza-spiro[2.5]oct-6-ylmethyl)-7-methyl-6-oxo-hexahydro-pyrazino[2,1-b][1,3]oxazine-8-carboxylic acid (3,4-dichloro-phenyl)-amide,
- (4S,7S,9aR)-4-[2-((S)-4-Hydroxy-6-aza-spiro[2.5]oct-6-yl)-ethyl]-7-methyl-6-oxo-hexahydro-pyrazino[2,1-c][1,4]oxazine-8-carboxylic acid (3,4-dichloro-phenyl)-amide,
- (4S,7S,9aR)-4-[2-((S)-4-Hydroxy-6-aza-spiro[2.5]oct-6-yl)-ethyl]-7-methyl-6-oxo-hexahydro-pyrazino[2,1-c][1,4]oxazine-8-carboxylic acid (3-chloro-4-trifluoromethyl-phenyl)-amide,
- (3S,6R,8aS)-6-[2-((S)-4-Hydroxy-6-aza-spiro[2.5]oct-6-yl)-ethyl]-3-methyl-4-oxo-hexahydro-pyrrolo[1,2-a]pyrazine-2-carboxylic acid (3,4-dichloro-phenyl)-amide,
- (3S,6S,8aR)-3-[3-((S)-4-Hydroxy-6-aza-spiro[2.5]oct-6-yl)-3-oxo-propyl]-6-methyl-5-oxo-hexahydro-oxazolo[3,2-a]pyrazine-7-carboxylic acid (3,4-dichloro-phenyl)-amide,
- (3S,6R,8aS)-6-[3-((S)-4-Hydroxy-6-aza-spiro[2.5]oct-6-yl)-3-oxo-propyl]-3-methyl-4-oxo-hexahydro-pyrrolo[1,2-a]pyrazine-2-carboxylic acid (3-chloro-4-trifluoromethyl-phenyl)-amide,
- (4S,7S,9aR)-4-[3-((S)-4-Hydroxy-6-aza-spiro[2.5]oct-6-yl)-3-oxo-propyl]-7-methyl-6-oxo-hexahydro-pyrazino[2,1-c][1,4]oxazine-8-carboxylic acid (3,4-dichloro-phenyl)-amide,
- (4S,7S,9aR)—N-(3-chloro-4-(trifluoromethyl)phenyl)-4-(3-((S)-4-hydroxy-6-azaspiro[2.5]octan-6-yl)-3-oxo-propyl)-7-methyl-6-oxohexahydropyrazino[2,1-c][1,4]oxazine-8(1H)-carboxamide,
- (4S,7S,9aR)—N-(3,4-dichlorophenyl)-4-(2-(4,4-difluoro-6-azaspiro[2.5]octan-6-yl)ethyl)-7-methyl-6-oxohexahydropyrazino[2,1-c][1,4]oxazine-8(1H)-carboxamide,
- (3S,6R,9aS)-6-[3-((S)-4-Hydroxy-6-aza-spiro[2.5]oct-6-yl)-3-oxo-propyl]-3-methyl-4-oxo-octahydro-pyrido[1,2-a]pyrazine-2-carboxylic acid (3,4-dichloro-phenyl)-amide,
- (3S,6R,9aS)-6-[3-((S)-4-Hydroxy-6-aza-spiro[2.5]oct-6-yl)-3-oxo-propyl]-3-methyl-4-oxo-octahydro-pyrido[1,2-a]pyrazine-2-carboxylic acid (3-chloro-4-trifluoromethyl-phenyl)-amide,
- (3S,6R,9aS)-6-[2-((S)-4-Hydroxy-6-aza-spiro[2.5]oct-6-yl)-ethyl]-3-methyl-4-oxo-octahydro-pyrido[1,2-a]pyrazine-2-carboxylic acid (3,4-dichloro-phenyl)-amide,
- (3S,6R,9aS)-6-[2-((S)-4-Hydroxy-6-aza-spiro[2.5]oct-6-yl)-ethyl]-3-methyl-4-oxo-octahydro-pyrido[1,2-a]pyrazine-2-carboxylic acid (3-chloro-phenyl)-amide, and
- (3S,6R,9aS)-6-[2-((S)-4-Hydroxy-6-aza-spiro[2.5]oct-6-yl)-ethyl]-3-methyl-4-oxo-octahydro-pyrido[1,2-a]pyrazine-2-carboxylic acid (3-fluoro-phenyl)-amide.

19. A compound according to formula (I'),

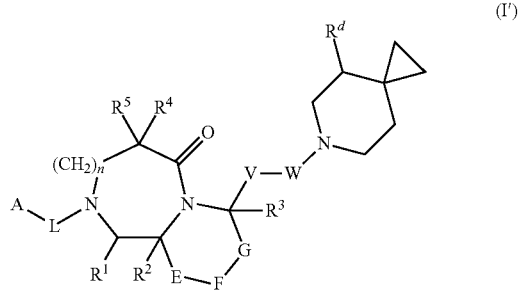

wherein
A is selected from the group consisting of: aryl, heteroaryl, arylmethyl and heteroarylmethyl, wherein the said aryl, heteroaryl and the aryl of arylmethyl are optionally substituted by one to three substituents independently selected from the group consisting halogen, aryl, heteroaryl, $C_{1-6}$ alkyl, halo$C_{1-6}$ alkyl, $C_{1-6}$ alkoxy and halo $C_{1-6}$ alkoxy;

E is CH$_2$ or O;

F is selected from the group consisting of: CH$_2$, O, N(R$^8$), S, SO and SO$_2$;

G is selected from the group consisting of: a single bond, CH$_2$, and CH$_2$CH$_2$, with the proviso that, when E is O, then F is not O, S, SO or SO$_2$;

L is selected from the group consisting of: a bond, NH—C(=O), NH—C(=S), and CH=CH—C(=O);

R$^1$, R$^2$ and R$^3$ are independently of each other selected from the group consisting of:
  hydrogen,
  C$_{1-6}$ alkyl, which is optionally substituted by one to three substituents independently selected from the group consisting of hydroxy, C$_{1-6}$ alkoxy, carboxyl, carbamoyl, mono or di-C$_{1-6}$ alkyl substituted aminocarbonyl and C$_{1-6}$ alkoxycarbonyl, aryl and heteroaryl, wherein said heteroaryl and aryl are optionally substituted by one to three substituents independently selected from the group consisting of halogen, C$_{1-6}$ alkyl, halo C$_{1-6}$ alkyl, C$_{1-6}$ alkoxy and halo C$_{1-6}$ alkoxy,
  C$_{3-7}$ cycloalkyl, and
  aryl;

R$^4$ and R$^5$ are independently of each other selected from the group consisting of:
  hydrogen,
  C$_{1-6}$ alkyl, which is optionally substituted by one to three substituents independently selected from the group consisting of amino, hydroxy, carboxyl, carbamoyl, mono or di-C$_{1-6}$ alkyl substituted aminocarbonyl and C$_{1-6}$ alkoxycarbonyl, and
  C$_{3-7}$ cycloalkyl, which is optionally substituted by one to three substituents independently selected from the group consisting of amino, hydroxy, carboxyl, carbamoyl, mono or di-C$_{1-6}$ alkyl substituted aminocarbonyl and C$_{1-6}$ alkoxycarbonyl; or R$^4$ and R$^5$, together with the carbon atom to which they are attached, form C$_{3-7}$ cycloalkyl or heterocyclyl which is optionally substituted by one to three substituents independently selected from the group consisting of C$_{1-4}$ alkyl, halo C$_{1-4}$ alkyl and halogen;

R$^8$ is selected from the group consisting of: hydrogen, C$_{1-6}$ alkyl, C(=O)R$^9$, and S(O$_2$)R$^9$;

R$^9$ is C$_{1-6}$ alkyl or C$_{3-7}$ cycloalkyl;

V is a C$_{1-4}$ alkylene, wherein each carbon atom is optionally substituted by one or two substituents independently selected from the group consisting of:
  hydroxy,
  C$_{1-6}$ alkyl,
  C$_{1-6}$ alkoxy,
  hydroxy-C$_{1-6}$ alkyl,
  C$_{1-6}$ alkoxy-C$_{1-6}$ alkyl,
  halogen, and
  halo C$_{1-6}$ alkyl;

W is selected from the group consisting of: a bond CH$_2$ and C(=O);

n is 0 or 1;

R$^d$ is selected from the group consisting of: hydroxy, cyano, NR$^a$R$^b$, halogen, C$_{1-6}$ alkyl, halo C$_{1-6}$ alkyl, hydroxy C$_{1-6}$ alkyl, C$_{1-6}$ alkoxy, C$_{1-6}$ alkoxy, C$_{1-6}$ alkyl, C$_{3-7}$ cycloalkyl, C$_{1-6}$ alkoxycarbonyl, acyl, —C(O)NR$^a$R$^b$, —NR$^a$—C(O)—R$^b$, —NR$^a$—C(O)—OR$^b$, —NR$^a$—C(O)—NR$^b$, —NR$^a$—SO$_2$—R$^b$, —NR$^a$—SO$_2$—NR$^b$R$^c$, —OC(O)NR$^a$R$^b$, —OC(O)OR$^a$, C$_{1-6}$ alkylsulfonyl, C$_{1-6}$ alkylsulfinyl, C$_{1-6}$ alkylthio, phenyl, phenyl C$_{1-3}$ alkyl, heteroaryl, heteroaryl C$_{1-3}$ alkyl and heterocyclyl, and said phenyl, the phenyl of said phenyl C$_{1-3}$ alkyl, said heteroaryl, the heteroaryl of heteroaryl C$_{1-3}$ alkyl, and said heterocyclyl are optionally substituted by one to three substituents independently selected from the group consisting of hydroxy, cyano, NR$^a$R$^b$, halogen, C$_{1-6}$ alkyl, halo C$_{1-6}$ alkyl, hydroxy C$_{1-6}$ alkyl, C$_{1-6}$ alkoxycarbonyl, acyl, C(O)NR$^a$R$^b$, —NR$^a$—C(O)—R$^b$, —NR$^a$—C(O)—OR$^b$, —NR$^a$—C(O)—NR$^b$, —NR$^a$—SO$_2$—R$^b$, —NR$^a$—SO$_2$—NR$^b$R$^c$, —OC(O)NR$^a$R$^b$, —OC(O)OR$^a$, C$_{1-6}$ alkylsulfonyl, C$_{1-6}$ alkylsulfinyl and C$_{1-6}$ alkylthio, and one or two ring carbon atoms of said heterocyclyl is optionally replaced with a carbonyl group; and R$^a$, R$^b$ and R$^c$ are independently hydrogen or C$_{1-6}$ alkyl;

or a pharmaceutically acceptable salt thereof.

20. A compound according to formula (I")

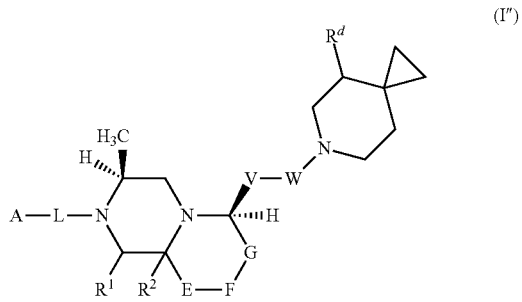

wherein
  A is selected from the group consisting of: aryl, heteroaryl, arylmethyl and heteroarylmethyl, wherein the said aryl, heteroaryl and the aryl of arylmethyl are optionally substituted by one to three substituents independently selected from the group consisting of halogen, aryl, heteroaryl, C$_{1-6}$ alkyl, haloC$_{1-6}$ alkyl, C$_{1-6}$ alkoxy and halo C$_{1-6}$ alkoxy;

E is CH$_2$ or O;

F is selected from the group consisting of: CH$_2$, O, N(R$^8$), S, SO and SO$_2$;

G is selected from the group consisting of: a single bond, CH$_2$, and CH$_2$CH$_2$, with the proviso that, when E is O, then F is not O, S, SO or SO$_2$;

L is selected from the group consisting of: a bond, NH—C(=O), NH—C(=S), and CH=CH—C(=O);

R$^1$ and R$^2$ are independently of each other selected from the group consisting of:
  hydrogen,
  C$_{1-6}$ alkyl, which is optionally substituted by one to three substituents independently selected from the group consisting of hydroxy, C$_{1-6}$ alkoxy, carboxyl, carbamoyl, mono or di-C$_{1-6}$ alkyl substituted aminocarbonyl and C$_{1-6}$ alkoxycarbonyl, aryl and heteroaryl, wherein said heteroaryl and aryl are optionally substituted by one to three substituents independently selected from the group consisting of halogen, C$_{1-6}$alkyl, halo C$_{1-6}$ alkyl, C$_{1-6}$ alkoxy and halo C$_{1-6}$ alkoxy,
  C$_{3-7}$ cycloalkyl, and
  aryl;

R$^8$ is selected from the group consisting of: hydrogen, C$_{1-6}$ alkyl, C(=O)R$^9$, and S(O$_2$)R$^9$;

R$^9$ is C$_{1-6}$ alkyl or C$_{3-7}$ cycloalkyl;

V is a C$_{1-4}$ alkylene, wherein each carbon atom is optionally substituted by one or two substituents independently selected from the group consisting of:

hydroxy,
$C_{1-6}$ alkyl,
$C_{1-6}$ alkoxy,
hydroxy-$C_{1-6}$ alkyl,
$C_{1-6}$ alkoxy-$C_{1-6}$ alkyl,
halogen, and
halo $C_{1-6}$ alkyl;

W is selected from the group consisting of: a bond, $CH_2$ and $C(=O)$;

$R^d$ is selected from the group consisting of: hydroxy, cyano, $NR^aR^b$, halogen, $C_{1-6}$ alkyl, halo $C_{1-6}$ alkyl, hydroxy $C_{1-6}$ alkyl, $C_{1-6}$ alkoxy, $C_{1-6}$ alkoxy $C_{1-6}$ alkyl, $C_{3-7}$ cycloalkyl, $C_{1-6}$ alkoxycarbonyl, acyl, —C(O)$NR^aR^b$, —$NR^a$—C(O)—$R^b$, —$NR^a$—C(O)—$OR^b$, —$NR^a$—C(O)—$NR^b$, —$NR^a$—$SO_2$—$R^b$, —$NR^a$—$SO_2$—$NR^bR^c$, —OC(O)$NR^aR^b$, —OC(O)$OR^a$, $C_{1-6}$ alkylsulfonyl, $C_{1-6}$ alkylsulfinyl, $C_{1-6}$ alkylthio, phenyl, phenyl $C_{1-3}$ alkyl, heteroaryl, heteroaryl $C_{1-3}$ alkyl and heterocyclyl, and said phenyl, the phenyl of said phenyl $C_{1-3}$ alkyl, said heteroaryl, the heteroaryl of heteroaryl $C_{1-3}$ alkyl, and said heterocyclyl are optionally substituted by one to three substituents independently selected from the group consisting of hydroxy, cyano, $NR^aR^b$, halogen, $C_{1-6}$ alkyl, halo $C_{1-6}$ alkyl, hydroxy $C_{1-6}$ alkyl, $C_{1-6}$ alkoxycarbonyl, acyl, —C(O)$NR^aR^b$, —$NR^a$—C(O)—$R^b$, —$NR^a$—C(O)—$OR^b$, —$NR^a$—C(O)—$NR^b$, —$NR^a$—$SO_2$—$R^b$, —$NR^a$—$SO_2$—$NR^bR^c$, —OC(O)$NR^aR^b$, —OC(O)$OR^a$, $C_{1-6}$ alkylsulfonyl, $C_{1-6}$ alkylsulfinyl and $C_{1-6}$ alkylthio, and one or two ring carbon atoms of said heterocyclyl is optionally replaced with a carbonyl group; and $R^a$, $R^b$ and $R^c$ are independently hydrogen or $C_{1-6}$ alkyl; or a pharmaceutically acceptable salt thereof.

* * * * *